US010722486B2

(12) United States Patent
Chow et al.

(10) Patent No.: US 10,722,486 B2
(45) Date of Patent: Jul. 28, 2020

(54) METHOD OF TREATING PATIENTS WITH A FACTOR XA INHIBITOR, ASPIRIN, AND VERAPAMIL

(71) Applicant: Morgandane Scientific, LLC, Corona Del Mar, CA (US)

(72) Inventors: Christina Chow, Newport Beach, CA (US); Sundar Srinivasan, Corona Del Mar, CA (US)

(73) Assignee: MORGANDANE SCIENTIFIC, LLC, Corona Del Mar, CA (US)

( * ) Notice: Subject to any disclaimer, the term of this patent is extended or adjusted under 35 U.S.C. 154(b) by 0 days.

(21) Appl. No.: 16/102,176

(22) Filed: Aug. 13, 2018

(65) Prior Publication Data

US 2020/0046673 A1     Feb. 13, 2020

(51) Int. Cl.
*A61K 31/277* (2006.01)
*A61K 31/616* (2006.01)
*A61K 31/5377* (2006.01)

(52) U.S. Cl.
CPC ........ *A61K 31/277* (2013.01); *A61K 31/5377* (2013.01); *A61K 31/616* (2013.01)

(58) Field of Classification Search
None
See application file for complete search history.

(56) References Cited

U.S. PATENT DOCUMENTS

| | | |
|---|---|---|
| 7,157,456 B2 | 1/2007 | Straub et al. |
| 7,585,860 B2 | 9/2009 | Straub et al. |
| 7,592,339 B2 | 9/2009 | Straub et al. |
| 2012/0022787 A1 | 1/2012 | Lebeau et al. |
| 2012/0095019 A1 | 4/2012 | Sinha et al. |
| 2014/0010876 A1 | 1/2014 | Benke et al. |
| 2017/0239260 A1 | 8/2017 | Srinivasan et al. |
| 2018/0311256 A1 | 11/2018 | Srinivasan et al. |
| 2019/0142839 A1 | 5/2019 | Srinivasan et al. |
| 2019/0167693 A1 | 6/2019 | Srinivasan et al. |

FOREIGN PATENT DOCUMENTS

| | | | |
|---|---|---|---|
| WO | WO 2017/021482 | * | 2/2017 |
| WO | WO 2017/147074 A1 | | 8/2017 |

OTHER PUBLICATIONS

Eikelboom et al. in New England Journal of Medicine 377(14):1319-1330 (2017) (Year: 2017).*
L-Lacoste et al. in Circulation 89(2), 631-635 (1994) (Year: 1994).*
Galanis et al. in Advances in Surgery 45, 361-390 (2011) (Year: 2011).*
Kubitza et al. in British Journal of Clinical Pharmacology 70(5), 703-712 (2010) (Year: 2010).*
Harris et al. in Kidney International 31, 41-46 (1987) (Year: 1987).*
Antoniou, Sotiris, "Rivaroxaban for the treament and prevention of thromboembolic disease." Journal of Pharmacy and Pharmacology (2015); 67: 1119-1131.
Extended European Search Report for European Patent Application No. 17757069.4, dated Jun. 28, 2019, 10 pages.
Galanis, et al., "Prophylaxis for Deep Vein Thrombosis and Pulmonary Embolism in the Surgical Patient". Adv Surg. (2011); 45(1): 361-390. ISSN: 0065-3411.
Ismail, et al., "Minimal Physiologically Based Pharmacokinetic and Drug-Drug-Disease Interaction Model of Rivaroxaban and Verapamil in Healthy and Renally Impaired Subjects." The Journal of Clinical Pharmacology (2017); 00(0) 1-8.
Palladino, et al., "Evaluation of the oral direct factor Xa inhibitor—betrixaban". Expert Opin Investig Drugs (Nov. 2013); 22(11): 1465-1472. Epub Aug. 22, 2013.
Tamayo, S., et al., "Characterizing Major Bleeding in Patients With Nonvalvular Atrial Fibrillation: A Pharmacovigilance Study of 27 467 Patients Taking Rivaroxaban." Database Medline [Online] U.S. National Library of Medicine (NLM), Bethesda, MD, US; Feb. 2015 (Feb. 2015), Database accession No. NLM25588595; & Clinical Cardiology (Feb. 2015); 38(2): 63-68, XP002792066, ISSN: 1932-8737.
Mueck, W., et al., "Clinical pharmacokinetic and pharmacodynamic profile of rivaroxaban." Database Medline [Online] U.S. National Library of Medicine (NLM), Bethesda, MD, US; Jan. 2014 (Jan. 2014), Database accession No. NLM23999929; & Clinical Pharmacokinetics (Jan. 2014); 53(1) 1-16, XP055298782, ISSN: 1179-1926.
Xarelto® Label Aug. 2013 (rivaroxaban), Highlights of Prescribing Information / Package Insert / Label, Janssen Pharmaceuticals, Inc. (2011), Titusville, NJ; Revised: Aug. 2013, Boxed Warning, Reference ID: 3353958, Initial U.S. Approval: 2011, 57 pages.
Xarelto® (rivaroxaban), Highlights of Prescribing Information / Package Insert / Label, Initial U.S. Approval: 2011, Revised: Sep. 2015, Tablets: 10 mg, 15 mg, and 20 mg, Reference ID: 3817480, Janssen Pharmaceuticals, Inc. 2011, Titusville, NJ; 49 pages.
(Wikipedia) Verapamil. https://en.wikipedia.org/wiki/Verapamil, 6 pages [No Date Provided]. [Author Unknown] "Bleeding with dabigatran, rivaroxaban, apixaban. No antidote, and little clinical experience"; Prescrire Int. (2013); 22(139): 155-159. (Abstract).
Anand, et al., "Rivaroxaban with or without aspirin in patients with stable peripheral or carotid artery disease: an international, randomised, double-blind, placebo-controlled trial." The Lancet (2018); 391 (10117): 219-229. Epub Nov. 10, 2017.
Bevyxxa™ (betrixaban), Highlights of Prescribing Information / Package Insert / Label, Portola Pharmaceuticals, Inc., South San Francisco, CA; Revised: Jun. 2017, Reference ID: 4115694, Initial U.S. Approval: 2017, 21 pages.
Center for Drug Research and Evaluation, Food and Drug Administration. Application 022406Orig1s000. Clinical Pharmacology and Biopharmaceutics Review(s). NDA: 22-406 (Rivaroxaban), Submission Date: Dec. 10, 2010, Brand Name: Xarelto®, Reference ID: 2955610. Accessed Oct. 9, 2017. https://www.accessdata.fda.gov/drugsatfda_docs/nda/2011/022406Orig1s000ClinPharmR.pdf. 295 pages.

(Continued)

*Primary Examiner* — Dennis Heyer
(74) *Attorney, Agent, or Firm* — Cooley LLP

(57) ABSTRACT

The present disclosure in various embodiments teaches methods of treating patients in need of treatment with a Factor Xa inhibitor, and who are also concomitantly administered aspirin and verapamil.

19 Claims, 5 Drawing Sheets

(56) References Cited

OTHER PUBLICATIONS

Center for Drug Research and Evaluation, Food and Drug Administration. Application 202439Orig1s000. Clinical Pharmacology and Biopharmaceutics Review(s). NDA: 202-439 (Rivaroxaban), Submission Date: Jan. 5, 2011, Brand Name: Xarelto®, Reference ID: 2900791. Available at: https://www.accessdata.fda.gov/drugsatfda_docs/nda/2011/202439Orig1s000ClinPharmR.pdf. 74 pages.

Center for Drug Research and Evaluation, Food and Drug Administration. Application No. 208383Orig1s000. Clinical Pharmacology and Biopharmaceutics Review(s). NDA 208383 (Betrixaban), Submission Date: Oct. 23, 2016, Brand Name: BevyxXa®, Reference ID: 4112948. Available at: https://www.accessdata.fda.gov/drugsatfda_docs/nda/2017/208383Orig1s000ClinPharmR.pdf. Accessed Oct. 25, 2017, 32 pages.

Center for Drug Research and Evaluation, Food and Drug Administration. Guidance for Industry: Drug Interaction Studies—Study Design, Data Analysis, Implications for Dosing, and Labeling Recommendations. 2012. Available at: https://www.fda.gov/downloads/drugs/guidances/ucm292362.pdf. Accessed Oct. 25, 2017, 32 pages.

Cholerton, et al. "The role of individual human cytochromes P450 in drug metabolism and clinical response." Trends Pharmacol Sci. (1992); 13(12): 434-439.

Connolly, et al., "Rivaroxaban with or without aspirin in patients with stable coronary artery disease: an international, randomised, double-blind, placebo-controlled trial." The Lancet (2018); 391 (10117): 205-218. Epub Nov. 10, 2017.

Eikelboom, et al., "Rivaroxaban with or without Aspirin in Stable Cardiovascular Disease." N Engl J Med. (2017); 377 (14): 1319-1330.

Eliquis® (apixaban), Highlights of Prescribing Information / Package Insert / Label, Bristol-Myers Squibb Company, Princeton, NJ and Pfizer, Inc., New York, NY; Revised: Jul. 2016, Reference ID: 3961165, Initial U.S. Approval: 2012, 44 pages.

Favaloro, et al., "The new oral anticoagulants and the future of haemostasis laboratory testing." Biochemia Medica (2012); 22.3: 329-341.

Fuster, Valentin, et al. "ACC/AHA/ESC 2006 Guidelines for the Management of Patients with Atrial Fibrillation: a report of the American College of Cardiology/American Heart Association Task Force on Practice Guidelines and the European Society of Cardiology Committee for Practice Guidelines (Writing Committee to Revise the 2001 Guidelines for the Management of Patients With Atrial Fibrillation): developed in collaboration with the European Heart Rhythm Association and the Heart Rhythm Society." Circulation (2006);114(7): e257-354.

Girgis, et al., "Population Pharmacokinetics and Pharmacodynamics of Rivaroxaban in Patients with Non-valvular Atrial Fibrillation: Results from ROCKET AF." The Journal of Clinical Pharmacology (2014); 54(8): 917-927.

Gnoth, et al. "In vitro and in vivo P-glycoprotein transport characteristics of Rivaroxaban." Journal of Pharmacology and Experimental Therapeutics (2011); 338.1: 372-380.

Grillo, et al., "Utility of a physiologically-based pharmacokinetic (PBPK) modeling approach to quantitatively predict a complex drug-drug-disease interaction scenario for rivaroxaban during the drug review process: implications for clinical practice." Biopharm. Drug Dispos. (2012); 33: 99-110.

Hillarp, et al., "Effects of the oral, direct factor Xa inhibitor rivaroxaban on commonly used coagulation assays." Journal of Thrombosis and Haemostasis (2011): 9.1: 133-139.

International Preliminary Report on Patentability for Application No. PCT/US2017/018727, dated Aug. 28, 2018, 9 pages.

International Search Report and Written Opinion for Application No. PCT/US2017/018727, dated May 3, 2017, 17 pages.

Johansson, et al., "Longterm oral treatment with high doses of verapamil in lone atrial fibrillation." Clinical.Cardiology (1984); 7.3: 163-170.

Ketter, et al., "The emerging role of cytochrome P450 3A in psychopharmacology." Journal of Clinical Psychopharmacology (1995); 15.6: 387-398. (Abstract).

Kubitza, D., et al., "Safety, pharmacodynamics, and pharmacokinetics of BAY 59-7939—an oral, direct Factor Xa inhibitor—after multiple dosing in healthy male subjects." Eur J Clin Pharmacol (2005); 61: 873-880.

Kubitza, et al., "Effects of renal impairment on the pharmacokinetic, pharmacodynamics and safety of rivaroxaban, an oral, direct Factor Xa inhibitor." Brit J of Clinical Pharma (2010); 70.5: 703-712.

Kubitza, et al., "Multiple Dose Escalation Study Investigating the Pharmacodynamics, Safety, and Pharmacokinetics of BAY 59-7939, an Oral, Direct Factor Xa Inhibitor in Healthy Male Subjects." Journal of the American Society of Hematology (2003), vol. 102 No. 11; Abstract # 3004, Poster Board #-Session: 224-III, American Society of Hematology, Forty-Fifth Annual Meeting Program and Abstracts, Dec. 6-9, 2003, San Diego, California, 2 pages.

Kubitza, et al., "Safety, pharmacodynamics, and pharmacokinetics of single doses of BAY 59-7939, an oral, direct factor Xa inhibitor." Clinical Pharmacology & Therapeutics (2005); 78(4): 412-421.

Kubitza, et al., "Single Dose Escalation Study Investigating the Pharmacodynamics, Safety, and Pharmacokinetics of BAY 59-7939 an Oral, Direct Factor Xa Inhibitor in Healthy Male Subjects." Journal of the American Society of Hematology (2003), vol. 102 No. 11; Abstract # 3010, Poster Board #-Session: 230-111, American Society of Hematology, Forty-Fifth Annual Meeting Program and Abstracts, Dec. 6-9, 2003, San Diego, California, 2 pages.

Lee, et al., "Identifying a Selective Substrate and Inhibitor Pair for the Evaluation of CYP2J2 Activity." Drug Metabolism and Disposition (2012); vol. 40 pp. 943-951.

McDonald, et al., "Cross-Country Comparison of Rivaroxaban Spontaneous Adverse Event Reports and Concomitant Medicine Use with the Potential to Increase the Risk of Harm." Drug Safety (2014); 37(12): 1029-1035.

Mega, et al., "Rivaroxaban in Patients with a Recent Acute Coronary Syndrome." N Engl J Med (2012); 366 (1): 9-19.

Mendell,et al., "Drug-Drug Interaction Studies of Cardiovascular Drugs Involving P-Glycoprotein, an Efflux Transporter, on the Pharmacokinetics of Edoxaban, an Oral Factor Xa Inhibitor." Am. J. Cardiovasc Drugs (2013); 13:331-342.

Moore, et al., "An Open-Label Study to Estimate the Effect of Steady-State Erythromycin on the Pharmacokinetics, Pharmacodynamics, and Safety of a Single Dose of Rivaroxaban in Subjects with Renal Impairment and Normal Renal Function." The Journal of Clinical Pharmacology (2014); 54(12): 1407-1420.

Mueck, et al. "Co-administration of rivaroxaban with drugs that share its elimination pathways: pharmacokinetic effects in healthy subjects." Br J Clin Pharmacol. (2013); 76: 455-466.

Mueck, et al., "Clinical pharmacokinetic and pharmacodynamic profile of rivaroxaban." Clinical Pharmacokinetics (2014); 53.1: 1-16.

Nielsen, et al., "Renal function and non-vitamin K oral anticoagulants in comparison with warfarin on safety and efficacy outcomes in atrial fibrillation patients: a systemic review and meta-regression analysis." Clin. Res. Cardiol. (2015); 104(5): 418-429. doi: 10.1007/s00392-014-0797-9. Epub Nov. 22, 2014.

Pauli-Magnus, et al., "Characterization of the Major Metabolites of Verapamil as Substrates and Inhibitors of P-glycoprotein." J Pharmacol Exp Ther (2000); 293:376-382.

Polli, Joseph W., et al., "Rational use of in vitro P-glycoprotein assays in drug discovery." Journal of Pharmacology and Experimental Therapeutics (2001); 299.2: 620-628.

Praxbind®, Product Insert, Initial U.S. Approval: 2015, Reference ID: 3834358, Boehringer Ingelheim International GmbH (2015), 10 pages.

Savaysa™ (edoxaban), Highlights of Prescribing Information / Package Insert / Label, Daiichi Sankyo, Inc., Parsippany, NJ; Revised: Sep. 2017, Reference ID: 4160896, Initial U.S. Approval: 2015, 35 pages.

Sridhar, et al., "Insights on cytochrome p450 enzymes and inhibitors obtained through QSAR studies." Molecules (2012); 3:17(8):9283-9305.

(56) References Cited

OTHER PUBLICATIONS

Tamayo, Sally, et al., "Characterizing major bleeding in patients with nonvalvular atrial fibrillation: a pharmacovigilance study of 27 467 patients taking rivaroxaban." Clinical Cardiology (2015); 38.2: 63-68.

Tayal, et al., "Atrial fibrillation detected by mobile cardiac outpatient telemetry in cryptogenic TIA or stroke." Neurology. (2008); 71(21):1696-1701.

US Food and Drug Administration, "Drug Development and Drug Interactions: Table of Substrates, Inhibitors, and Inducers." Available at: https://www.fda.gov/drugs/developmentapprovalprocess/developmentresources/druginteractionslabeling/ucm093664.htm#. Accessed Oct. 25, 2017, 16 pages.

Washam, J.B., et al., "S 4081 / 408—Efficacy and Safety of Rivaroxaban versus Warfarin in Patients Taking Non-dihydropyridine Calcium Channel Blockers: Results From the ROCKET AF Trial." Program Planner Presentation, Nov. 8, 2015, Scientific Session (2015), Orlando, FL, http://www.abstractsonline.com/pp8/#!/3795/presentation/37668, Abstract.

Weinz, et al., "Metabolism and excretion of rivaroxaban, an oral, direct Factor Xa inhibitor, in rats, dogs and humans." Drug Metab Dispos. (2009); 37:1056-1064.

Wessler, et al., "The P-glycoprotein transport system and cardiovascular drugs." Journal of the American College of Cardiology (2013); 61.25: 2495-2502.

Westlind, Anna, et al., "Interindividual differences in hepatic expression of CYP3A4: relationship to genetic polymorphism in the 5'-upstream regulatory region." Biochem Biophys Res Commun (1999); 259: 201-205.

Wolf, P.A., et al., "Atrial fibrillation as an independent risk factor for stroke: the Framingham Study." Stroke. (1991); 22(8):983-938.

Wolf, P.A., et al., "Atrial Fibrillation: A Major Contributor to Stroke in the Elderly. The Framingham Study." Arch Intern Med. (1987); 147(9): 1561-1564.

Xarelto® (rivaroxaban), Highlights of Prescribing Information / Package Insert / Label, Janssen Pharmaceuticals, Inc., Titusville, NJ; Revised: Mar. 2017, 070441-170404, Initial U.S. Approval: 2011, 16 pages.

Xarelto® (rivaroxaban), Highlights of Prescribing Information / Package Insert / Label, Janssen Pharmaceuticals, Inc. (2011), Titusville, NJ; Revised: May 2016, Warnings and Precautions (5.3); Revised: Aug. 2016, Warnings and Precautions (5.2, 5.4); Reference ID: 3977521, Initial U.S. Approval: 2011, 49 pages.

Zambrano and Herman, (Ed. China A. Sacks), "Rib Fracture Associated with Bordetella pertussis Infection." N Engl J Med (2018); 378: e4.

* cited by examiner

METHOD OF TREATING PATIENTS WITH A FACTOR XA INHIBITOR, ASPIRIN, AND VERAPAMIL

BACKGROUND

Cardiovascular diseases and major cardiovascular events are a leading cause of morbidity and mortality. Such disease and events are caused by abnormalities in haemostasis. Maintenance of normal haemostasis—between bleeding and thrombosis—is subject to complex regulatory mechanisms. Uncontrolled activation of the coagulant system or defective inhibition of the activation processes may cause formation of local thrombi or embolisms in vessels (arteries, veins) or in heart cavities. This may lead to serious thromboembolic disorders, such as myocardial infarct, angina pectoris (including unstable angina), reocclusions and restenoses after angioplasty or aortocoronary bypass, stroke, transitory ischaemic attacks, peripheral arterial occlusive disorders, pulmonary embolisms or deep venous thromboses.

Cardiovascular diseases and events have traditionally been managed by antiplatelet therapies or anticoagulant therapies. Aspirin is known to reduce platelet aggregation. Specifically, aspirin irreversibly blocks the formation of thromboxane A2, which reduces platelet aggregation. As such, aspirin reduces the risk of secondary ischemic events in individuals who have experienced coronary artery disease (e.g., angina, myocardial infarct, peripheral artery disease, or cerebrovascular ischemia). Aspirin also may reduce the risk of initial thrombotic events in healthy individuals who are at risk of suffering a major cardiovascular event. For this reason, many individuals take aspirin on a regular basis for the primary or secondary prevention of thromboembolic disease.

Unfortunately, aspirin only reduces platelet aggregation by blocking formation of thromboxane A2, and the coagulation cascade is a complex process that is mediated by numerous other factors. Furthermore, the use of aspirin can be accompanied by undesirable side effects including major bleeding events (e.g., gastrointestinal bleeding).

Anticoagulant drugs target various procoagulant factors in the coagulation pathway to reduce the risk of thrombotic disorders by reducing coagulation. One new class of anticoagulant drugs is Factor Xa inhibitors, which play a central role in the cascade of blood coagulation by inhibiting Factor Xa directly.

Rivaroxaban is a Factor Xa inhibitor drug used to treat disorders including deep vein thrombosis (DVT) and pulmonary embolism (PE). It is also used to help prevent strokes or serious blood clots in people who have atrial fibrillation.

The use of rivaroxaban, however, presents considerable risk to patients. Because rivaroxaban reduces blood clotting, higher than expected blood concentrations of rivaroxaban can cause serious adverse events, most notably elevated rates of internal bleeding/hemorrhage. Conversely, any under dosing of the drug leaves a patient at risk of potentially fatal clotting events.

Because both aspirin and rivaroxaban, separately, present significant bleed risks, the combined use can be dangerous.

SUMMARY OF THE DISCLOSURE

In some embodiments, the present disclosure is directed to a method of treating a patient in need of treatment with a Factor Xa (e.g., rivaroxaban) inhibitor and who is concomitantly administered aspirin and verapamil, comprising administering a dose of rivaroxaban which is a reduced dose relative to the dose recommended for an otherwise identical (or the same) patient who is not concomitantly administered aspirin and verapamil (e.g. about 99.5% to about 0% of the reference dose). In various embodiments, the patient in need of treatment with a Factor Xa inhibitor has normal renal function, and in still other embodiments, the patient has renal insufficiency (mild, moderate or severe as described herein).

In some embodiments, the present disclosure is directed to a method of treating a patient in need of treatment with rivaroxaban and who is concomitantly administered aspirin and verapamil, comprising administering a reduced dose of rivaroxaban (e.g., reduced relative to the reference dose) in an immediate release or rapid release formulation which achieves blood plasma concentrations described herein as safe (e.g., below that provided by a single 5 mg dose of rivaroxaban when administered in the absence of verapamil, or bioequivalent to that provided by a single 2.5 mg dose of rivaroxaban when administered in the absence of verapamil). In various embodiments, the patient in need of treatment with a Factor Xa inhibitor has normal renal function, and in still other embodiments, the patient has renal insufficiency (mild, moderate or severe as described herein).

In some embodiments, the present disclosure provides a method of treating a patient with rivaroxaban, comprising (a) administering about 100 to about 480 mg of verapamil daily to the patient; (b) administering about 75 mg to about 325 mg of aspirin to the patient; and (c) administering about 0.5 mg to less than about 2.5 mg of rivaroxaban to the patient. In some embodiments, the dose of verapamil administered in step (a) is 120, 240, 360, or 480 mg. In some embodiments, the dose of aspirin administered in step (b) is 100 mg. In some embodiments, the patient is administered 100 mg of aspirin once daily. In some embodiments, the dose of rivaroxaban administered in step (c) ranges from 0.5 mg to about 2.0 mg of rivaroxaban (for example about 0.5 mg, about 0.75 mg, about 1.0 mg, about 1.25 mg, about 1.5 mg, about 1.75 mg, or about 2.0 mg). In some embodiments, the dose of rivaroxaban is administered in an immediate release or rapid release formulation. In some embodiments, the dose of rivaroxaban administered in step (c) ranges from about 15% to about 95% of the dose recommended for an otherwise identical patient who is not concomitantly administered aspirin and verapamil.

In some embodiments, the present disclosure is directed to a method of treating a patient concomitantly administered rivaroxaban, aspirin, and verapamil, wherein the dose of rivaroxaban administered to the patient is 15% to about 95% (e.g., about 15%, about 20%, about 25%, about 30%, about 35%, about 40%, about 45%, about 50%, about 55%, about 60%, about 65%, about 70%, about 75%, about 80%, about 85%, about 90%, or about 95%, inclusive of all values and subranges therebetween) of the rivaroxaban dose recommended for the otherwise identical (or the same) patient who is not concomitantly administered verapamil.

In some embodiments, the patient is administered the dose rivaroxaban twice daily. In some embodiments, the total daily dose of rivaroxaban administered to the patient is less than 5 mg (e.g., the total daily dose of rivaroxaban administered to the patient is about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, or about 4.75 mg).

In some embodiments, the patient has a $C_{max}$ and AUC that is bioequivalent to a single 2.5 mg dose of rivaroxaban in an otherwise identical patient that was not coadministered verapamil. In some embodiments, the patient has a $C_{max}$ and AUC below those provided by administration of a single 5 mg dose of rivaroxaban in an otherwise identical patient that was not coadministered verapamil.

In some embodiments, the present disclosure provides a method of treating a patient with rivaroxaban, wherein after administering the dose of rivaroxaban, the patient has at least one of the following characteristics: (i) a geometric mean of an area under the plasma concentration-time curve (AUC) of rivaroxaban in the range of from about 80% of about 165.4 µg·h/L to about 125% of about 551.9 µg·h/L after a single dose of rivaroxaban; (ii) a geometric mean of a maximum blood plasma concentration ($C_{max}$) of rivaroxaban in the range of from about 80% of 28.6 µg/L to about 125% of 103.0 µg/L after a single dose of rivaroxaban; (iii) a risk of major bleeding of no more than about 4.5%; and (iv) a prothrombin time of 20-30 seconds.

In some embodiments, the present disclosure provides a method of treating a patient with rivaroxaban, wherein after administering the dose of rivaroxaban, the patient has at least one of the following characteristics: (i) a geometric mean AUC of rivaroxaban that is less than 1064.25 µg·h/L after a single dose of rivaroxaban; and (ii) a geometric mean $C_{max}$ of rivaroxaban that is less than 181.25 µg/L after a single dose of rivaroxaban; (iii) a risk of major bleeding of no more than about 4.5%; and (iv) a prothrombin time of 20-30 seconds.

In some embodiments, the present disclosure is directed to a method of treating a patient in need of treatment with a rivaroxaban and who is concomitantly administered aspirin and verapamil, comprising administering a dose of rivaroxaban in an extended or delayed release formulation which maintains blood plasma concentrations described herein as safe (e.g., blood plasma concentrations below those provided by a 5 mg dose of rivaroxaban when administered in the absence of verapamil, or bioequivalent to those provided by a 2.5 mg dose of rivaroxaban when administered in the absence of verapamil). In various embodiments, the patient in need of treatment with a Factor Xa inhibitor has normal renal function, and in still other embodiments, the patient has renal insufficiency (mild, moderate or severe as described herein).

In some embodiments, the present disclosure is directed to a method of treating a patient in need of treatment with rivaroxaban, comprising: (a) administering about 100 to about 480 mg of verapamil daily to the patient; (b) administering about 75 mg to about 325 mg of aspirin to the patient; and (c) administering less than about 5 mg of rivaroxaban (e.g., about 1.75 mg to less than 5 mg) to the patient once-daily, wherein at least a portion of the dose of rivaroxaban is administered in a delayed release or extended release component. In some embodiments, the dose of verapamil administered in step (a) is 120, 240, 360, or 480 mg. In some embodiments, the dose of aspirin administered in step (b) is 100 mg. In some embodiments, the patient is administered 100 mg of aspirin once daily.

In some embodiments, the present disclosure is directed to a method of treating patient concomitantly administered rivaroxaban, aspirin, and verapamil, wherein the dose of rivaroxaban administered to the patient is equal to the reference dose, but at least a portion of the dose of rivaroxaban is administered in a delayed or extended release formulation. In such embodiments, the patient has a $C_{max}$ and AUC below those corresponding to a 5 mg dose of rivaroxaban administered BID in an otherwise identical patient that was not coadministered verapamil. In particular embodiments, the patient has a $C_{max}$ and AUC that is bioequivalent to those provided by a 2.5 mg dose of rivaroxaban administered BID in an otherwise identical patient that was not coadministered verapamil.

In some embodiments, after administering a delayed release or extended release formulation of rivaroxaban, the patient has at least one of the following characteristics: (i) a geometric mean of an area under the plasma concentration-time curve (AUC) of rivaroxaban that is within the range of about 80%-125% of the AUC measured for an otherwise identical patient that was administered 2.5 mg of rivaroxaban, twice daily, but was not administered verapamil; (ii) a geometric mean of a maximum blood plasma concentration (Cmax) of rivaroxaban in the range of from about 80% of 28.6 µg/L to about 125% of 103.0 µg/L after a single dose of rivaroxaban; (iii) a risk of major bleeding of no more than about 4.5%; and (iv) a prothrombin time of 20-30 seconds.

In some embodiments disclosed herein, the patient who is administered rivaroxaban in an extended or delayed release formulation (concomitantly with verapamil and aspirin according to the methods described herein) has a $C_{max}$ of rivaroxaban (e.g., after a single dose) that is no more than about 181.25 ng/mL. In some embodiments disclosed herein, the $C_{max}$ of rivaroxaban (after a single dose) in said patient is in the range of from about 80% of 28.6 µg/L to about 125% of 103.0 µg/L after a single dose of rivaroxaban.

In some embodiments disclosed herein, the patient who is administered rivaroxaban in an extended or delayed release formulation (concomitantly with verapamil and aspirin according to the methods described herein) has an AUC (after a single dose) in said patient which is less than 2,128.5 µg·h/L. In some embodiments disclosed herein, the AUC (after a single dose) in said patient is in the range of about 80% of about 330.8 µg·h/L to about 125% of about 1,103.8 µg·h/L after a single dose of rivaroxaban.

In some embodiments, the present disclosure is directed to a method of treating a patient in need of treatment with a Factor Xa inhibitor, e.g., a patient with renal insufficiency (mild, moderate or severe as described herein) comprising administering a dose of rivaroxaban which is a reduced dose (e.g., about 99.5% to about 0%) relative to the dose recommended for an otherwise identical (or the same) patient who does not have renal insufficiency. In some embodiments, the patient is administered about 0.5 mg to less than 2.5 mg of rivaroxaban in an immediate release or rapid release formulation, or less than about 5 mg (e.g., about 1.25 to less than 5 mg) in an extended release or delayed release formulation.

In some embodiments, the present disclosure is directed to treatment of a patient with a medical condition requiring treatment with aspirin (in conjunction with verapamil and a Factor Xa inhibitor), where the purpose of treatment is selected from the group consisting of decreasing the risk of major cardiovascular events (death, myocardial infarction, or stroke) in patients with chronic coronary and/or peripheral artery disease, reducing the risk of acute limb ischemia in patients with peripheral artery disease, decreasing the risk of major cardiovascular events (death, myocardial infarction, or stroke) in patients with acute coronary syndrome, and prevention and treatment of venous thromboembolism in cancer patients or patients with active cancer (also referred to as cancer-associated venous thromboembolism).

In some embodiments, the patient experiences an increase in the risk of internal bleeding of no more than about 5% (e.g., about 5%, about 4.5%, about 4%, about 3.5%, about 3%, about 2.5%, about 2%, about 1.5%, and about 1%, inclusive of all values and subranges therein) compared to an otherwise identical patient that was administered aspirin alone. In some embodiments, the patient's risk of a major bleeding event is less than about 5%. In some embodiments, the efficacy in treating the condition is similar to the efficacy observed for the same condition in an otherwise identical patient that was treated with 2.5 mg of rivaroxaban but was not treated with verapamil.

In any of the various embodiments disclosed herein, the patient who is concomitantly administered rivaroxaban, aspirin, and verapamil can have normal renal function.

In any of the various embodiments disclosed herein, the patient who is concomitantly administered rivaroxaban, aspirin, and verapamil can be mildly renally impaired.

In any of the various embodiments disclosed herein, the patient who is concomitantly administered rivaroxaban, aspirin, and verapamil can have moderate renal impairment.

In any of the various embodiments disclosed herein, the patient who is concomitantly administered rivaroxaban, aspirin, and verapamil can have severe renal impairment.

In any of the various embodiments disclosed herein, the maximum prothrombin time of said patient concomitantly administered rivaroxaban, aspirin, and verapamil ranges from about 20 to about 30 seconds.

In some embodiments, the patient has a $CL_{Cr}$ of less than or equal to about 89 mL/min. In some embodiments, the patient has a $CL_{Cr}$ of less than or equal to about 79 mL/min. In some embodiments, the patient has a $CL_{Cr}$ of 60-89 mL/min. In some embodiments, the patient has a $CL_{Cr}$ of 30-59 mL/min. In some embodiments, the patient has a $CL_{Cr}$ of 15-29 mL/min.

In some embodiments disclosed herein, the patient who is concomitantly administered rivaroxaban, aspirin, and verapamil is not renally impaired. In some embodiments disclosed herein, the patient who is concomitantly administered rivaroxaban, aspirin, and verapamil is mildly renally impaired. In some embodiments disclosed herein, the patient who is concomitantly administered rivaroxaban, aspirin, and verapamil is moderately renally impaired. In some embodiments disclosed herein, the patient who is concomitantly administered rivaroxaban, aspirin, and verapamil is severely renally impaired.

In some embodiments disclosed herein, the dose of rivaroxaban administered to the patient who is concomitantly administered rivaroxaban, aspirin, and verapamil is selected to generate a prothrombin time of said patient ranging from about 20-30 seconds. In still further embodiments, the dose of rivaroxaban is less than 2.5 mg, and the rivaroxaban is administered in an immediate release or rapid release composition. In still further embodiments, the dose of rivaroxaban is about 1.25 mg, and the rivaroxaban is administered in an immediate release or rapid release composition.

In some embodiments, the dose of rivaroxaban administered in the method of the present invention is such that the AUC ($AUC_{inf}$, $AUC_{ss}$, or AUC for a single dose) and/or $C_{max}$ ($C_{max}$ for a single dose or steady state) values of rivaroxaban in the treated patient population does not exceed target values, e.g., the AUC and $C_{max}$ values measured for a patient administered a 2.5 mg dose of rivaroxaban in the presence of aspirin but not verapamil. The rivaroxaban dose is designed such that a particular statistical PK parameter characterizing the particular patient population (e.g., maximum, mean of highest 3 patients, 90% confidence interval upper boundary, median, arithmetic mean, geometric mean, 90% confidence level lower boundary, or minimum of the $AUC_{inf}$ and/or $C_{max}$) does not exceed the selected target value. So, for example, for a patient concomitantly administered rivaroxaban, aspirin, and verapamil, the dose of rivaroxaban intended to provide an AUC of less than 1064.25 μg·hr/L for the patient in a population with the highest exposure ("maximum") would be a dose of no more than 2.5 mg rivaroxaban (e.g., about 1.75 mg rivaroxaban in an immediate release formulation, or an extended release formulation having a release profile that achieves blood plasma levels approximately corresponding to a 2.5 mg dose of rivaroxaban in a patient that was not concomitantly treated with verapamil).

In some embodiments, the present disclosure is directed to treating a patient in need of treatment with rivaroxaban and aspirin, wherein the patient is not concomitantly administered verapamil (i.e., the coadministration of rivaroxaban and verapamil is contraindicated for such patients). That is, in some embodiments, present methods are directed to treating a patient in need of treatment with rivaroxaban and who is concomitantly administered aspirin and verapamil, wherein the patient ceases administration of verapamil and then is administered rivaroxaban. In alternative embodiments, the patient is currently being treated with rivaroxaban and aspirin, and is in need of treatment with verapamil. In such embodiments, the patient ceases treatment with rivaroxaban and then is administered verapamil. In various embodiments, the patient has normal renal function, or in other embodiments, the patient has renal insufficiency (mild, moderate or severe as described herein).

BRIEF DESCRIPTIONS OF THE FIGURES

Figure 3:
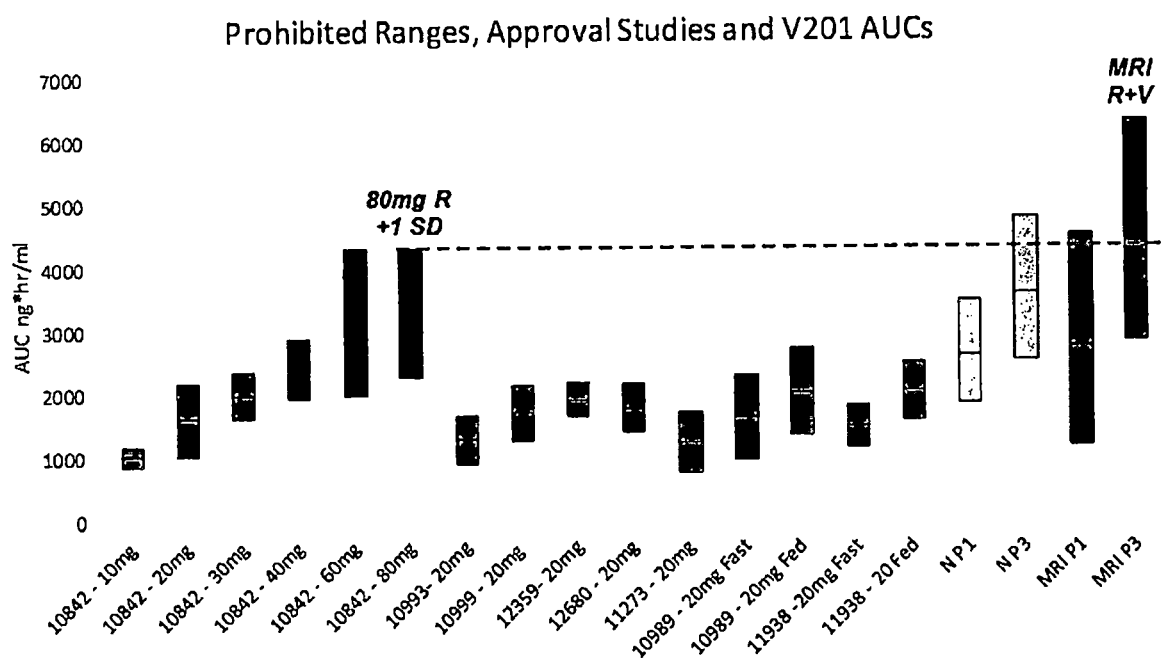

FIG. 3 shows the ranges of steady state rivaroxaban AUC values for various single dose rivaroxaban treatments (10842, 10993, 10999, 12359, 12680, 11273, 10989, 11938, studies), and single dose rivaroxaban plus verapamil treatments. Abbreviations in the figure are N: Normal renal function; MRI: mild renal impairment; P1: 20 mg rivaroxaban only; P3: 20 mg rivaroxaban and 360 mg verapamil. The lines represent the geometric mean and for the numbered studies the top and bottom represent +/−1 standard deviation. For the Normal and MRI groups by study period, the lines represent the geometric mean and the top and bottom represent the sample maximum and minimum.

Figure 4:
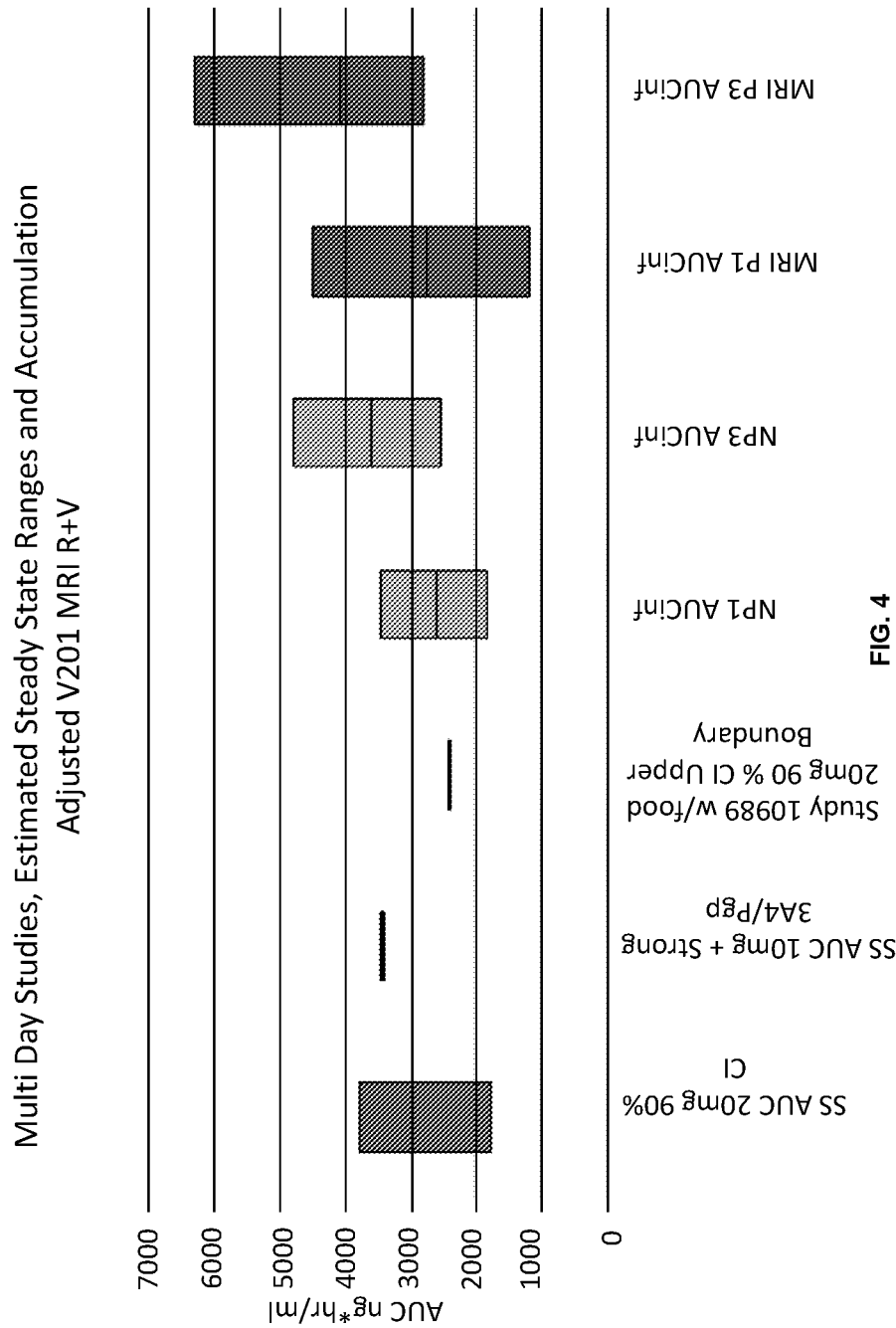

FIG. 4 shows the 90% confidence level rivaroxaban AUC value (single 20 mg dose) (Label "A"), steady state rivaroxaban AUC value as described in the Clinical Pharmacology approval documents for rivaroxaban and separately the 10 mg steady state dose in the presence of a strong CYP3A4/Pgp inhibitor (Label "B") from the same report. The third item, (Label "C") shows the upper 90% confidence interval value for rivaroxaban administered under fed conditions as determined in clinical study 10989. These values are compared to the ranges of AUC measured by the present inventors under various conditions. Abbreviations in the figure are SS: steady state; CI: confidence interval; AUC inf: area under the curve extrapolated to infinity; N: Normal renal function; MRI: mild renal impairment; P1: a single 20 mg rivaroxaban only; P3: a single 20 mg rivaroxaban plus 360 mg verapamil.

Figure 5:
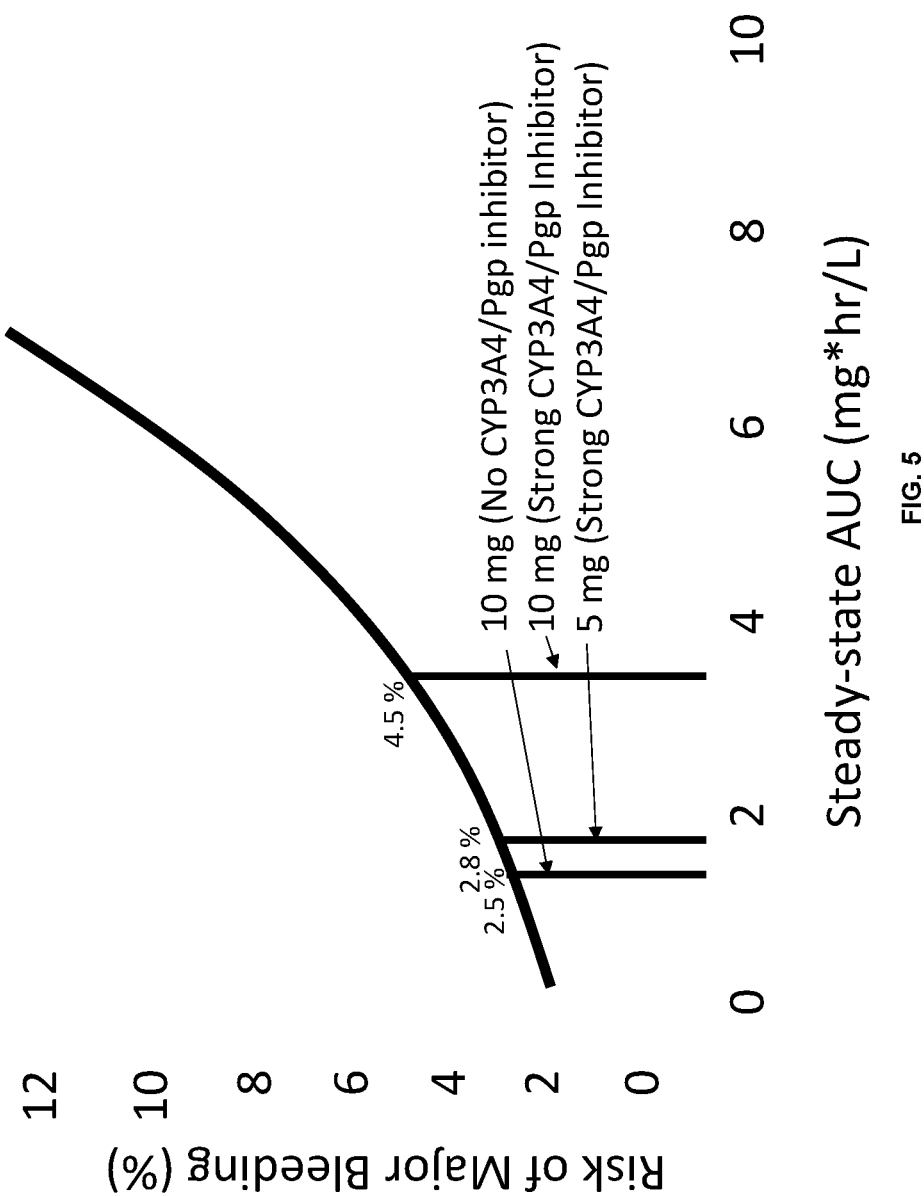

FIG. 5 shows the relationship between the steady state AUC values and the risk of major bleeding. See Center for Drug Evaluation and Research, Application No. 022406Orig1s000, Clinical Pharmacology and Biopharmaceutics Review(s), at page 36, which is hereby incorporated by reference in its entirety.

DETAILED DESCRIPTION

While the following terms are believed to be well understood by one of ordinary skill in the art, the following definitions are set forth to facilitate explanation of the presently disclosed subject matter.

Throughout the disclosure, singular forms such as "a," "an," and "the" are often used for convenience. However, it should be understood that the singular forms are intended to include the plural, except when context or an explicit statement indicates that the singular alone is intended.

Throughout this application, the term "about" is used to indicate that a value includes the inherent variation of error for the device or the method being employed to determine the value, or the variation that exists among the samples being measured. In some embodiments, the term "about" means within 5% of the reported numerical value. When used in conjunction with a range or series of values, the term "about" applies to the endpoints of the range or each of the values enumerated in the series, unless otherwise indicated.

As used herein, the term "concomitant" refers to the co-administration of two or more drugs. In some embodiments, concomitant administration includes the administration of two or more drugs at substantially the same time, either as a mixture (e.g., in a coformulation), or as separate doses. In some embodiments, concomitant administration also includes the sequential administration of two or more drugs, wherein both drugs are simultaneously present at clinically relevant levels in a patient's plasma.

As used herein, the term "pharmacokinetics" refers to a drug's movement into, through, and out of the body, including: the drug's absorption, bioavailability, tissue distribution, metabolism, and excretion.

As used herein, $C_{max}$ refers to peak plasma concentration of a therapeutic agent as it relates to a particular drug dose (e.g. rivaroxaban dose).

As used herein, $T_{max}$ refers to the time required to reach peak concentration.

As used herein, $C_{ave}$ refers to average plasma concentration of a therapeutic agent under a particular drug dosing schedule (e.g. rivaroxaban dosing schedule).

As used herein, $C_{min}$ refers to the minimum plasma concentration of a therapeutic agent under a particular drug dosing schedule (e.g. rivaroxaban dosing schedule).

In some embodiments, the present disclosure teaches that the pharmacokinetic effects of a drug can be compared based on area under the curve (AUC) values. The pharmacokinetic AUC of a drug is calculated by taking the integral (area under the curve) of the concentration of a drug against time.

As used herein, "treating" in the context of treating a condition refers to reducing or eliminating the symptoms of a condition, reducing the risk of, or preventing the patient from experiencing the symptoms of a condition. For example, treatment of a condition with rivaroxaban can reduce the risk of stroke or systemic embolism in patients, reducing the risk of recurrence of deep vein thrombosis and pulmonary embolism, the prophylaxis of deep vein thrombosis, etc.

As used herein, $AUC_{0-\infty}$ or $AUC_{inf}$ refers to the area under the curve extrapolated to infinity, after administration of a single dose of drug. $AUC_{ss}$ refers to the AUC under steady state conditions, and approximates $AUC_{inf}$.

As used herein, the term "pharmacodynamics" refers to a drug's effect(s) on the body, including: receptor binding, postreceptor effects, and chemical interactions. In some embodiments, a drug's pharmacodynamics determines the onset, duration, and intensity of that drug's effect.

As used herein, the term "major bleeding" or "major bleeding event" refers to a fatal bleeding event or an overt internal bleeding event with a corresponding drop in hemoglobin levels. The internal bleeding typically occurs at a critical site, including gastrointestinal, intracranial, intraocular, intraspinal, intra-articular, intramuscular with compartment syndrome, and pericardial, retroperitoneal. The decrease in hemoglobin may be at least about 1 g/dl, at least about 1.5 g/dl, at least about 2 g/dl, at least about 2.5 g/dl, at least about 3 g/dl, at least about 3.5 g/dl, at least about 4 g/dl, at least about 4.5 g/dl, at least about 5 g/dl, at least about 5.5 g/dl, at least about 6 g/dl, at least about 6.5 g/dl, or more. In some embodiments, major bleeding is defined by the International Society on Thrombosis and Haemostasis (ISTH) criteria of overt bleeding accompanied by a decrease in the hemoglobin level of at least 2 g/dl or transfusion of at least 2 units of packed red cells, occurring at a critical site (intracranial, intraocular, intraspinal, intra-articular, intramuscular with compartment syndrome, pericardial, retroperitoneal), or resulting in death. In some embodiments, major bleeding is defined by the Thrombolysis in Myocardial Infarction (TIMI) criteria, which defines major bleeding as an intracranial haemorrhage, a decrease in hematocrit of 15%, or a 5 g/dl decrease in the haemoglobin concentration.

As used herein, the term "prothrombin time" (PT) refers to a blood test that measures how long it takes blood to clot. In some embodiments, a prothrombin time test can be used to measure of a patient's haemostasis. In some embodiments, PT can be used to measure the effectiveness or exposure to a blood clotting drug. Persons having skill in the art sometimes interchangeably refer to a PT test as an INR. However, since the INR is calibrated specifically for warfarin, PT measurements suitable for rivaroxaban would not be comparable to the INR standards for warfarin. Additionally, PT measurements are subject to variability based on the test reagent and laboratory test ranges determined by each institution.

As used herein, the term "immediate release" refers to oral formulations, such as tablets and capsules, which are formulated to release rivaroxaban immediately after oral administration. In such formulations, no deliberate effort is made to modify the rate of drug release. Immediate release and instant release may be used interchangeably herein.

As used herein, the term "rapid release" has the same definition as used in U.S. Pat. No. 9,539,218, and refers to a composition (e.g., tablet) which has a Q value (30 minutes) of 75% according to USP release method using apparatus 2 (paddle).

As used herein, "BID" refers to twice-daily administration.

As used herein, "extended release" refers to a pharmaceutical formulation which releases the active agent (e.g., rivaroxaban) over an extended period of time. An extended period of time is longer than that of the immediate release component as described herein, such that the total amount of active agent in an extended release component is released over a period of about 1 to 24 hours, e.g., over about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours, inclusive of all ranges between any of these values. In some embodiments, an extended release formulation may also include an immediate release component.

As used herein, "delayed release" refers to a pharmaceutical formulation which substantially prevents the release (meaning releasing no more than about 5-10%) of rivaroxaban contained in the delayed release component for a defined period of time after oral administration. In some embodiments, delayed release substantially prevents release of the active for at least 30 minutes after oral administration, e.g., 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, about 3 hours, about 4 hours, about 5 hours, about 6 hours, about 7 hours, about 8 hours, or more. In some embodiments, delayed release also encompasses formulations in which a portion of the active (e.g., rivaroxaban) is not released from the formulation for a particular period of time. That is, a delayed release formulation may also include an immediate release component. For example, in some embodiments, the delayed release component can substantially prevent release of at least about 40% (e.g., about 40% to about 60%) of the total amount of rivaroxaban in the pharmaceutical formulation for at least about 30 minutes after oral administration, e.g., 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, about 3 hours, about 4 hours, about 5 hours, about 6 hours, about 7 hours, about 8 hours, or more.

Rivaroxaban was developed with the premise that it would not require the type of monitoring required for conventional anticoagulant drugs such as warfarin (Coumadin). PT/INR tests are conventionally used specifically for monitoring vitamin K antagonists such as warfarin. Alternative tests, such as the activated partial thromboplastin time (APTT) are conventionally used to monitor the use of unfractionated heparin. However, as discussed in Favaloro et al., Biochemia Medica 2012; 22(3): 329-41, the PT/INR and APTT tests are not suitable for monitoring patients treated with rivaroxaban because inconsistent results are obtained for rivaroxaban depending on factors such as the reagents used, and the tests are either too sensitive or insensitive to be useful. In addition, such tests are not calibrated for rivaroxaban, and therefore there is no standardized measure for the activity of rivaroxaban in such patients. While the literature suggests that suitable tests could be developed, presently there are no validated or generally recognized methods suitable for monitoring the use of rivaroxaban in hospital laboratories or available to healthcare providers. See also, Xarelto® Package Insert (Revised August/2016, section 5.7). Consequently, there are no current methods available for monitoring the dose titration of rivaroxaban. Indeed, the sponsor of the rivaroxaban NDA maintains that dose titration is not appropriate in most patient populations (Application Number: 022406Orig1s000 Clinical Pharmacology and Biopharmaceutics Review(s), Addendum to Apr. 6, 2009 Review). See Hillarp et al., Journal of Thrombosis and Haemostasis, 9: 133-139; Favarolo et al., Biochemia Medica 2012; 22(3): 329-41; Nielsen et al., Clin. Res. Cardiol. 22 Nov. 2014 (published online); and Mueck et al., Clin. Pharmacokinet (2014) 53:1-16.

As used herein, $E_{max}$ refers to peak effect of a therapeutic agent related to a particular drug dose (e.g. rivaroxaban dose).

As used herein, the term "AUEC" refers to area under the effect curve. In some embodiments, the pharmacodynamic AUEC of an effect for a particular drug is calculated by taking the integral (area under the curve) of the drug's measured effect against time.

In some embodiments, the AUEC of rivaroxaban is calculated based on the integral of the prothrombin time effect a rivaroxaban dose has on a patient over time.

As used herein, "renal impairment" means the individual has a clinically relevant level of renal function which is less than levels of renal function generally considered to be normal. Levels of renal function, renal sufficiency or renal impairment can be determined using any of the methods known in the art or described herein. Currently, one common method for determining the level of renal sufficiency in an individual is determining creatinine clearance ($CL_{Cr}$) in the individual using the Cockcroft-Gault equation. In some embodiments, the present disclosure teaches alternative methods of measuring renal impairment, for example those described in U.S. Published App. 2012/022787.

As disclosed herein, the individual's actual body weight, ideal body weight, or otherwise adjusted body weight can be used in the equation. In some embodiments, the following are criteria for determining the level of renal sufficiency using creatinine clearance ($CL_{Cr}$) and the Cockcroft-Gault equation:

Normal renal function > or =80 mL/min
Mild renal impairment=50-79 mL/min
Moderate renal impairment=30-49 mL/min
Severe renal impairment<30 mL/min Newer criteria for determining the level of renal sufficiency using $CL_{Cr}$ define the cut-offs between normal, and mild-severe renal impairment using slightly different $CL_{Cr}$ ranges:

Normal renal function > or =90 mL/min
Mild renal impairment=60-89 mL/min
Moderate renal impairment=30-59 mL/min
Severe renal impairment=15-29 mL/min
Kidney failure<15 mL/min A "patient" is a living organism, typically a human.

For nearly all FDA approved drugs, the "recommended" dose or "reference" dose (or doses) of the drug are determined based on the plasma level (or range of plasma levels) of the drug required to provide the desired clinical effect(s) and/or avoid undesirable side effects. The recommended dose(s) of a particular drug are those recognized in the art as suitable for treating a patient with particular physical characteristics (or within a range of particular characteristics), and are thus the dose(s) provided in the package insert for the drug. Thus, in various embodiments, the methods of the present disclosure are directed to adjustments or changes in the dosing of rivaroxaban relative to the FDA "recommended" dose, e.g., in the package insert for rivaroxaban, as suitable for treating a patient with particular physical characteristics. Thus, as used herein, the "recommended dose" for rivaroxaban is distinct from doses which may be disclosed by particular physicians for particular patients. Depending on the specific pharmacokinetics and pharmacodynamics of the drug, the recommended dose may vary depending on one or more physical characteristics of the patient, for example age, gender, weight, body mass index, liver metabolic enzyme status (e.g., poor or extensive metabolizer status), disease state, etc. Xarelto® (rivaroxaban) is currently sold in three FDA-approved doses: 10 mg (e.g., NDC 50458-580-30), 15 mg (e.g., NDC-50458-578-30), and 20 mg (e.g., NDC 50458-579-30). As discussed in more detail herein, a twice daily dose of a 2.5 mg dose of rivaroxaban is currently being recommended in combination with aspirin.

The present disclosure provides for methods of treating patients with aspirin, rivaroxaban, and verapamil, and requires an adjustment of the rivaroxaban dose relative to the recommended dose in that patient if the patient was not concomitantly administered verapamil. A low dose of aspirin in combination with a low dose of rivaroxaban has been discovered to reduce the risks of major cardiovascular events in patients with clotting disorders or patients that are at risk of developing clotting disorders. For patients concomitantly administered rivaroxaban and verapamil, a common drug used to treat atrial fibrillation—a disease common to patients with clotting disorders and are thus on antiplatelet and/or anticoagulant therapies—the inventors surprisingly discovered that verapamil increases exposure to rivaroxaban to dangerous levels and may cause a significant risk of internal bleeding. As such, the inventors discovered that the dose of rivaroxaban must be reduced to minimize the risk of internal bleeding.

More specifically, studies investigating the effects of aspirin and rivaroxaban in patients with cardiovascular disease (e.g., coronary artery disease, carotid artery disease, and acute coronary syndrome) found that low doses of rivaroxaban (2.5 mg BID) and aspirin reduce several clinical outcomes, including stroke, myocardial infarction, and cardiovascular death, compared to aspirin alone and a higher dose of rivaroxaban (5 mg BID) alone. In addition, a 5 mg dose of rivaroxaban alone was also observed to increase the risk of major bleeding events compared to aspirin alone. While the combination of 2.5 mg rivaroxaban (BID) and aspirin was also observed to increase the risk of major bleeding events compared to aspirin alone, the additional clinical benefits of this combination therapy outweigh the risks. Thus, in order to achieve the clinical benefit without causing a dangerous increase in the internal bleed risk, it is essential to avoid raising the blood plasma concentration of rivaroxaban to unsafe levels, such as those achieved with a 5 mg dose of rivaroxaban alone.

The clinical studies with rivaroxaban and aspirin did not account for drug-drug interactions with rivaroxaban and moderate CYP3A4 and P-gp inhibitors. This is because the interaction between rivaroxaban and such moderate CYP3A4 and P-gp inhibitors was considered to be safe. However, the inventors have surprisingly discovered a previously unknown, and clinically significant drug-drug interaction with the calcium channel blocker, verapamil, a moderate CYP3A4 and P-gp inhibitor.

Verapamil is commonly administered to patients treated with rivaroxaban to treat atrial fibrillation and hypertension. While the prevailing knowledge in the art was that the concomitant administering of rivaroxaban and verapamil was safe at the recommended dose of rivaroxaban (i.e., a dose adjustment of rivaroxaban was not required), the inventors unexpectedly discovered that verapamil significantly increases the blood plasma levels of rivaroxaban. More specifically, the inventors discovered that concomitant administration of verapamil approximately doubles the blood plasma concentration of rivaroxaban, such that, e.g., a 20 mg dose of rivaroxaban in the presence of verapamil becomes a 40 mg dose of rivaroxaban (FIG. 3).

Accordingly, when patients are treated with aspirin, 2.5 mg of rivaroxaban, and verapamil, the 2.5 mg dose of rivaroxaban will effectively become a higher dose, for example 5 mg or more. Because a 5 mg dose of rivaroxaban (in combination with aspirin) presents an unacceptable bleed risk to a patient, the 2.5 mg dose of rivaroxaban (to patients concomitantly treated with aspirin, rivaroxaban, and verapamil) must be reduced as described herein (e.g., by about 15-95%, inclusive of all values and ranges in between) in order to safely treat the patient.

Thus, as discussed herein, the methods of the present disclosure are directed to treating patients with aspirin, rivaroxaban, and verapamil, and require an adjustment of the rivaroxaban dose relative to the recommended dose in that patient if the patient was not concomitantly administered verapamil. Alternatively as discussed herein, the methods of the present disclosure provide for an adjustment of the rivaroxaban dose relative to the recommended dose for an otherwise identical patient treated with aspirin but not concomitantly administered verapamil. As used herein, the term an "otherwise identical patient who is not concomitantly administered verapamil" refers to a patient whose physical characteristics relevant to dosing a combination of drugs (e.g., rivaroxaban and aspirin) are expected to be substantially the same as that of the patient being treated with a reduced rivaroxaban dose according to the presently disclosed methods—except for the concomitant administration of verapamil. In some embodiments, the otherwise identical patient will be of substantially the same age, sex, and body weight. In some embodiments, the substantially identical patient will also have substantially identical renal function and drug metabolism. In some embodiments, the recommended dose of the otherwise identical patient who is not concomitantly administered verapamil is the dose that would have been recommended to that same patient, had that patient not been concomitantly administered verapamil. In particular embodiments, the "recommended dose" of rivaroxaban of the otherwise identical patient who is not concomitantly administered verapamil (but who is treated with aspirin) is 2.5 mg of rivaroxaban. In further particular embodiments, the otherwise identical patient who is not concomitantly administered verapamil (but who is treated with aspirin) is administered 2.5 mg or rivaroxaban BID.

In some embodiments, the present disclosure is directed to treatment of a patient with a medical condition requiring treatment with aspirin (in conjunction with verapamil and a Factor Xa inhibitor), where the purpose of treatment is selected from the group consisting of decreasing the risk of major cardiovascular events (death, myocardial infarction, or stroke) in patients with chronic coronary and/or peripheral artery disease, reducing the risk of acute limb ischemia in patients with peripheral artery disease, decreasing the risk of major cardiovascular events (death, myocardial infarction, or stroke) in patients with acute coronary syndrome, prevention and treatment of venous thromboembolism (also referred to as cancer-associated venous thromboembolism) in cancer patients or patients with active cancer. Patients treated in this manner can have normal renal function, or can be mildly, moderately, or severely renally impaired.

In some embodiments, the present disclosure is directed to methods of treating a patient in need of antiplatelet and anticoagulant therapies with aspirin concomitantly with rivaroxaban and verapamil. Daily aspirin therapy is used to reduce platelet aggregation in patients with cardiovascular diseases or at risk of developing cardiovascular diseases, such as atherosclerosis, patients that have experienced a heart attack or stroke, or have a high risk of a heart attack or stroke, patients with a stent placed in a coronary artery, patients who have had coronary bypass surgery, or have chest pain due to coronary artery disease (e.g., angina), and patients (males over 50 and females older than 60) with diabetes and at least one other heart disease risk factor, such as smoking or high blood pressure.

Atrial fibrillation (AF) is a common cardiac disorder that is characterized by a disruption of the normal electrical impulses generated by the sinoatrial (SA) node. The resulting disorganized electrical impulses lead to an irregular heartbeat and abnormal blood flow.

AF is also a significant stroke risk factor. The characteristic lack of coordinated atrial contraction in AF can result in clot formation in the atrium, and particularly the left atrial appendage of the heart. The increased stasis of blood in the atrium due to loss of mechanical function (i.e. contraction), combined with poorly understood changes in the thrombogenicity of the atrial endocardial surface in AF is thought to be the primary basis for clot formation in the left atrium and left atrial appendage in AF.

If the blood clot leaves the atria and becomes lodged in an artery in the brain, a stroke results. Diagnosed AF is associated with a four- to five-fold increase in stroke risk. Approximately 15% of strokes in the U.S. occur in individuals previously diagnosed with AF. It is believed that even more strokes are associated with undiagnosed AF.

Hypertension is another common cardiac disorder. Hypertension is a condition in which there is an increase in resistance to blood flow through the vascular system. This resistance leads to increases in systolic and/or diastolic blood pressures. Hypertension places increased tension to the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Patients diagnosed with AF and/or hypertension often receive dual treatment of calcium channel blockers (e.g., for their heart arrhythmia and/or to lower blood pressure) and anticoagulants to reduce the risk of stroke.

Rivaroxaban (Formula I), which is commercially available under the trade name Xarelto®, is disclosed in U.S. Pat. No. 7,157,456 (B2), U.S. Pat. No. 7,585,860 (B2), and U.S. Pat. No. 7,592,339 (B2), each of which is hereby incorporated in their entireties for all purposes.

Rivaroxaban is a Factor Xa inhibitor drug used to treat thrombosis-related disorders, among other conditions as disclosed herein. Rivaroxaban activity is mediated though its inhibition of Factor Xa, which in turn reduces the conversion of prothrombin to thrombin. It is also used to help prevent strokes or serious blood clots in people who have atrial fibrillation.

Formula I

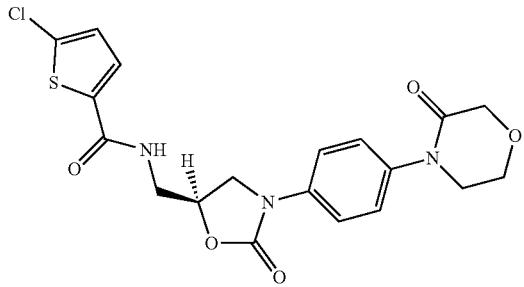

In some embodiments, the present disclosure is directed to methods of treating a patient in need of treatment with a Factor Xa inhibitor such as rivaroxaban, concomitantly with aspirin and verapamil. In some embodiments, a non-limiting list of the medical conditions which require treatment with a Factor Xa inhibitor (e.g., rivaroxaban) include: atrial fibrillation; deep vein thrombosis; patients undergoing major orthopedic surgery; deep vein thrombosis prophylaxis, deep vein thrombosis prophylaxis after abdominal surgery; deep vein thrombosis prophylaxis after hip replacement surgery; deep vein thrombosis prophylaxis after knee replacement surgery; deep vein thrombosis recurring event; heart attack; prevention of thromboembolism in atrial fibrillation; pulmonary embolism; pulmonary embolism recurring event; thromboembolic stroke prophylaxis; venous thromboembolism; prevention of ischemic stroke; recurring myocardial infarction; antiphospholipid antibody syndrome; sickle cell disease; prevention and treatment of venous thromboembolism in cancer patients; cancer associated thrombosis; cancer patients with central line associated clots in the upper extremity; reducing post-discharge venous thromboembolism risk in medically ill patients; treating young children with venous thrombosis (6 months-5 years); treatment of arterial or venous thrombosis in children from birth to less than 6 months; thromboprophylaxis in pediatric patients 2 to 8 years of age after the fontan procedure; valvular heart disease and atrial fibrillation; patients with atrial fibrillation with bioprosthetic mitral valves; treatment of symptomatic isolated distal deep vein thrombosis; superficial vein thrombosis; prevention of thrombosis after replacement of the aortic valve with a biological valve prosthesis; prevention of recurrence of stent thrombosis and cardiovascular events in patients with atrial fibrillation complicated with stable coronary artery disease; treatment of splanchnic vein thrombosis; prevention of recurrent thrombosis in patients with chronic portal vein thrombosis; prevention of recurrent symptomatic venous thromboembolism in patients with symptomatic deep vein thrombosis or pulmonary embolism; acute ischemic stroke with atrial fibrillation; venous thromboembolism prophylaxis in patients undergoing non-major orthopedic surgery; reducing the risk of major thrombotic vascular events in subjects with peripheral artery disease undergoing peripheral revascularization procedures of the lower extremities; prevention of cardiovascular events in patients with nonvalvular atrial fibrillation scheduled for cardioversion; reducing the risk of death, myocardial infarction, or stroke in participants with heart failure and coronary artery disease following an episode of decompensated heart failure; preventing major cardiovascular events in coronary or peripheral artery disease; reducing the risk of cardiovascular death, myocardial infarction, or stroke in patients with recent acute coronary syndrome; prevention of the composite of stroke or systemic embolism in patients with rheumatic valvular heart disease (RVHD) with atrial fibrillation or flutter who are unsuitable for vitamin K antagonist therapy, or in patients with RVHD without AF or Flutter with at least one of the following: Left atrial enlargement ≥5.5 cm, Left atrial spontaneous echo contrast, left atrial thrombus, frequent ectopic atrial activity (>1000/24 hours) on Holter ECG; prevention of restenosis after infrainguinal percutaneous transluminal angioplasty for critical limb ischemia; and decreasing the risk of cardiovascular disease, myocardial infarction, revascularization, ischemic stroke, and systemic embolism, treatment of arterial or venous thrombosis in neonates, treatment of venous thrombosis in young children, aged 6 months to 5 years, prevention of symptomatic venous thromboembolism (VTE) events and VTE-related death post-hospital discharge in high-risk, medically ill patients, reducing the risk of symptomatic lower extremity proximal deep vein thrombosis (DVT), asymptomatic lower extremity proximal DVT, symptomatic upper extremity DVT, symptomatic non-fatal pulmonary embolism (PE), incidental PE, and venous thromboembolism (VTE)-related death in ambulatory adult participants with various cancer types receiving systemic cancer therapy who are at high risk of developing a VTE, treatment of left atrial/left atrial appendage thrombus in subjects with nonvalvular atrial fibrillation or atrial flutter, thromboprophylaxis in pediatric participants 2 to 8 years of age after the Fontan Procedure, reducing the risk of major thrombotic vascular events in subjects with symptomatic peripheral artery disease undergoing peripheral revascularization procedures of the lower extremities, reducing the risk of death or thromboembolic events after transcatheter aortic valve replacement, prevention of stroke and noncentral nervous system systemic embolism in treatment-naïve Asian patients with non-valvular atrial fibrillation, secondary prevention of stroke and prevention of systemic embolism in patients with a recent embolic stroke of undetermined source, treatment of symptomatic leg superficial vein thrombosis, prophylaxis of VTE in non-major orthopedic surgery, prevention of leaflet thickening and reduced leaflet motion as evaluated by four-dimensional, volume-rendered computed tomography (4DCT), and prevention of ischemic stroke and neurocognitive impairment in AF reduction in the incidence of clinically significant hematoma after continued or interrupted novel oral anti-coagulant at the time of device surgery in patients with moderate to high risk of arterial thromboembolic events. In still other embodiments, the present invention is directed to treating a condition for which a factor Xa inhibitor is indicated, including reducing the risk of stroke and systemic embolism in patients with non valvular atrial fibrillation, treating deep vein thrombosis (DVT), treating pulmonary embolism (PE), reducing the risk of DVT, and reducing the risk of PE, the prophylaxis of DVT which leads to PE in patients undergoing knee or hip replacement therapy.

Use of rivaroxaban however, presents risks related to improper dosing. The FDA Draft Guidance on Rivaroxaban (Recommended September 2015) states that rivaroxaban demonstrates a "steep exposure-response relationship for both efficacy and safety" and therefore should "refer to the guidance on warfarin sodium." In other words, rivaroxaban is recognized as a drug having a narrow therapeutic index (e.g., meeting nearly all if not all the proposed FDA definitional terms of a Narrow Therapeutic Index drug; [Quality and Bioequivalence Standards for Narrow Therapeutic Index Drugs, Lawrence X Yu, Office of Generic Drugs, GPhA 2011 Fall Technical Workshop]), such that higher than expected plasma concentrations of rivaroxaban can cause serious adverse events, including internal bleeding/hemorrhage, and underdosing leaves a patient at risk of potentially fatal clotting events. Careful monitoring of patients treated with rivaroxaban is made even more difficult by the current lack of commercially available, specific antidotes against rivaroxaban overdosing, the lack of specific treatments with proven efficacy for severe bleeding linked with the use of rivaroxaban, and the lack of a routine coagulation test suitable for monitoring patients treated with rivaroxaban (as discussed herein). Conventional methods for reducing plasma levels which are useful for other anticoagulants such as dabigatran (e.g. haemodialysis and FDA-approved specific antidote idarucizumab) are not effective for rivaroxaban, because rivaroxaban cannot be eliminated from the body through dialysis and idarucizumab does not work against rivaroxaban.

The risks associated with incorrectly dosing rivaroxaban have caused the drug to be placed on the Institute for Safe Medication Practices (ISMP) list of high-alert medications as a drug with "heightened risk of causing significant potential harm." (Institute for Safe Medication Practices (ISMP) "ISMP List of High-Alert Medications in Acute Care Settings" https://www.ismp.org/tools/highalertmedications.pdf (Accessed October 2015)).

As provided in the rivaroxaban package insert (as revised October/2017 for NDA 022406 and 6/27/18 for NDA 202439), the 15 mg and 20 mg tablets should be taken with food, and the 10 mg tablets taken with or without food. For patients with nonvalvular atrial fibrillation, with $CL_{Cr}$>50 mL/min (normal to mild renal impairment), the 20 mg dose with the evening meal is recommended. For such patients with $CL_{Cr}$ 15-50 mL/min (severe to moderate renal impairment), the 15 mg dose with the evening meal is recommended. For patients with DVT, PE it is recommended that patients be administered 15 mg twice daily with food for the first 21 days, then 20 mg once daily with food for the remaining treatment. For the prophylaxis of DVT following hip or knee replacement surgery, 10 mg once daily is recommended with or without food. To reduce the risk of recurrence of DVT and/or PE in patients at continued risk for DVT and/or PE, it is recommended that patients be administered 10 mg once daily with or without food, after at least 6 months of standard anticoagulant treatment.

With respect to drug-drug interactions, the rivaroxaban package insert recommends avoiding concomitant use of rivaroxaban with combined P-gp and strong CYP3A4 inhibitors and inducers—that is, rivaroxaban and the combined P-gp and strong CYP3A4 inhibitors or inducers should not be coadministered; rather, one or the other drug should be discontinued. Although concomitant administration of rivaroxaban with drugs such as erythromycin, which is considered in the Xarelto® package insert to be a combined P-gp and moderate CYP3A4 inhibitor, has been observed to increase exposure to rivaroxaban, the package insert indicates that no precautions are necessary in such coadministration if the change in exposure is not expected to affect bleeding risk (see section 7.1 of the package insert), but that otherwise rivaroxaban should not be used unless the potential benefit justifies potential risk (see section 7.5 of the package insert). However, various studies discussed herein have shown that there are as yet no suitable assays for monitoring rivaroxaban dosing or assessing potential risk. (see e.g., Favarolo et al., Biochemia Medica 2012; 22(3):329-41; Xarelto® Package Insert).

Thus, although drug-drug interactions with rivaroxaban are known (e.g., elevated exposure to rivaroxaban in the presence of combined P-gp and CYP3A4 inhibitors), only in the case of coadministration of rivaroxaban and combined P-gp and strong CYP3A4 inhibitors is it necessary to change the dosing, e.g., by eliminating (i.e., avoiding) the use of rivaroxaban. Indeed, until the inventors' discovery, those of skill in the art have not identified clinically relevant interactions between rivaroxaban and commonly prescribed medications by virtue of rivaroxaban's multiple elimination pathways. (See W. Mueck et al., Clin Pharmacokinet (2014) 53:1-16). Thus, to-date, studies of drug-drug interactions with rivaroxaban have only identified that the coadministration of rivaroxaban with combined P-gp and strong CYP3A4 inhibitors (or strong inducers) is clinically relevant and thus requiring any modification of rivaroxaban dosing.

In such instances it is recommended that the rivaroxaban (or alternatively the strong inhibitor/inducer) be eliminated entirely from the treatment. Prior to the inventors' discovery, a dose reduction of rivaroxaban has not been recommended to address a clinically relevant drug-drug interaction.

In some embodiments, rivaroxaban dosing is compared in terms of its pharmacokinetic responses in different patients or patient populations, and in response to different situations. For example, in some embodiments, the present disclosure teaches methods of adjusting rivaroxaban dosing in patients concomitantly administered rivaroxaban, aspirin, and verapamil, relative to otherwise identical (or the same) patients not concomitantly administered aspirin and verapamil, in order to provide a particular rivaroxaban $AUC_{inf}$, $AUC_{ss}$, $C_{max}$, $C_{max\ ss}$ or $C_{ave}$ (or a range of values of such parameters) in said patient or patient population.

In other embodiments, rivaroxaban dosing is compared in terms of its pharmacokinetic and pharmacodynamics effects. For example, in some embodiments, the present disclosure teaches methods of adjusting rivaroxaban dosing in patients concomitantly administered rivaroxaban, aspirin, and verapamil, relative to otherwise identical (or the same) patients not concomitantly administered verapamil, in order to provide a particular prothrombin time or decrease the incidence rate of adverse events (or range of values of such parameters) in said patient or patient population.

Rivaroxaban pharmacokinetics and pharmacodynamics are at least partially a consequence of the drug's excretion/secretion and metabolism, particularly when coadministered with verapamil. Approximately one-third (36%) of each rivaroxaban dose is eliminated in the patient's urine as unprocessed active drug. Of this 36% elimination, 30% is eliminated through active renal secretion, while the remaining 6% is eliminated though glomerular filtration.

Renal impairment can also have effects on the pharmacodynamics of rivaroxaban. Even moderate changes in rivaroxaban AUC and half-life (tin) can lead to significant changes in haemostasis. In subjects with mild, moderate, and severe renal impairment administered a 10 mg dose of rivaroxaban, the AUEC for Factor Xa inhibition was 1.5-fold, 1.86-fold, and 2.0-fold higher than in healthy subjects, respectively. (Kubitza et al. Effects of renal impairment on the pharmacokinetic, pharmacodynamics and safety of rivaroxaban, an oral, direct Factor Xa inhibitor. Brit J of Clinical Pharma 70:5 703-712). In this work Kubitza et al. did not evaluate patients administered 2.5 or 5 mg doses, or evaluate drug-drug interactions. However, even in such studies, Kubitza et al. found that such increases in rivaroxaban exposure were unlikely to be clinically relevant, and that safety profiles were similar in patients with differing levels of renal impairment. Thus, Kubitza et al. did not recognize any need to adjust rivaroxaban doses in such patients.

However, the inventors have found that the recommended rivaroxaban dose should be adjusted in patients who are coadministered aspirin and verapamil. Thus in some embodiments, the present disclosure is directed to methods of treating patients comprising adjusting rivaroxaban dosing in response to changes in a patient's renal function.

Renal secretion of rivaroxaban is partially regulated by the Permeability glycoprotein (P-gp) pathway. P-gp transporters are found in the luminal membrane of several tissues, including the blood-brain barrier, the small intestine excretory cells, hepatocytes, and kidney proximal tubule epithelia. P-gp expression on intestinal epithelial cells regulates cellular uptake and absorption of drugs into enterocytes, whereas expression of P-gp transporters on the surface of hepatocytes and renal tubular cells regulates the elimination of drugs into the bile and urine.

In some embodiments, the present disclosure teaches that P-gp induction or inhibition can result in different pharmacokinetic and pharmacodynamic responses to fixed rivaroxaban doses. For example, in some embodiments, the present disclosure teaches that P-gp inhibition can lead to rivaroxaban overdosing due to decreased renal excretion of the drug.

P-gp inhibition is thought to involve modulation by 1 of 4 pathways: direct inhibition of binding sites that block the transport of substrates, ATP binding inhibition, ATP hydrolysis, or coupling of ATP hydrolysis to the translocation of the substrate.

Unfortunately, molecules that are modulators of P-gp substrates do not share any obvious structural characteristics, and it is thus difficult to predict the effect of concomitant administration of a drug on P-gp function.

Moreover, different drugs may interact differentially with P-gp, which results in a distinct mechanism of modulation of P-gp activity. As shown by Polli et al., Journal of Pharmacology and Experimental Therapeutics, vol. 299(2), 620-628 (2001), various assays of P-gp inhibition can give widely varying results. Polli et al. describe three different P-gp assays: the monolayer efflux assay (using Caco-2 cells), the ATPase and calcein-AM assays. Of the three, the monolayer efflux assay is considered the most reliable because it is a direct measurement of efflux. Polli et al. demonstrated that verapamil does not show efflux (i.e., is not a P-gp substrate) in the monolayer efflux assay, but provides positive results in the ATPase and calcein-AM assays.

Gnoth et al., Journal of Pharmacology and Experimental Therapeutics, vol. 338(1), 372-380 (2011) evaluated the P-gp transport characteristics of rivaroxaban, and rivaroxaban in the presence of potential P-gp inhibitors such as clarithromycin and erythromycin. The authors observed that erythromycin did not inhibit P-gp-mediated efflux of rivaroxaban across cell monolayers in vitro—in fact, erythromycin increased the efflux of rivaroxaban in a statistically significant manner. Thus, erythromycin and verapamil utilize distinct mechanisms in their interaction with and regulation of P-gp activity, which could lead to differing inhibitory effects. Gnoth et al. concluded that the impact of P-gp inhibition, alone, had only a marginal effect on the pharmacokinetics of rivaroxaban, and that only strong P-gp inhibitors at high doses might result in drug-drug interactions.

Approximately two-thirds of each rivaroxaban dose is subject to metabolic degradation via the liver's oxidative and hydrolytic pathways.

At least three functional CYP3A proteins exist in humans. The CYP3A4 monooxygenase is the predominant cytochrome P450 in human liver and small bowel. The protein displays a broad substrate specificity and it metabolizes more than 60% of all drugs that are currently in use, including contraceptive steroids, antidepressants, benzodiazepines, immunosuppressive agents, imidazole antimicotics, and macrolide antibiotics.

Rivaroxaban metabolic clearance is catalyzed by CYP3A4/5, CYP2J2, and CYP-independent mechanisms. The CYP3A4 isozyme in particular, accounts for approximately 18% of the rivaroxaban clearance.

In some embodiments, the present disclosure teaches that variations in CYP3A4 activity can result in different pharmacokinetic and pharmacodynamic responses to fixed rivaroxaban doses. A considerable variation in the CYP3A4 content and catalytic activity has been described in the general population. For example, studies have shown that the metabolic clearance of the CYP3A4 substrates exhibit a unimodal distribution with up to 20-fold variability between individual patients. This result is also born out in direct activity studies which demonstrated that the activities of the CYP3A4 protein in liver biopsies vary up to 30-fold between individuals.

In order to assess the effects of combined P-gp and CYP3A4 inhibitors on the metabolism of rivaroxaban, a study was conducted to examine the effects of co-administration of rivaroxaban with erythromycin, a combined moderate CYP3A4 inhibitor and P-gp inhibitor. Erythromycin is known to be eliminated mainly in the bile, and 2-15% renally (unchanged). However, based on this study, no dose adjustment for rivaroxaban in the presence of such a combined inhibitor was found to be necessary. Similar results were obtained for clarithromycin and fluconazole, suggesting significant interactions with other drugs in this category are unlikely. (Mueck et al. Co-administration of rivaroxaban with drugs that share its elimination pathways: pharmacokinetic effects in healthy subjects. British J. of Clinical Pharma 76:3 455-466).

On the contrary, the FDA-approved rivaroxaban label states that rivaroxaban use should be avoided (i.e., should not be administered at all) in patients receiving "concomitant combined P-gp and moderate CYP3A4 inhibitors" unless "the potential benefit justifies the potential risk." However, since, as discussed herein there is no clinically standardized test methodology for evaluating the pharmacodynamics of rivaroxaban as there are for other, conventional anticoagulants such as warfarin and heparin (i.e., PT/INR or APTT tests), there is no clinically acceptable or useful methodology for evaluating the potential risk.

In some embodiments, the present disclosure is directed to methods of adjusting rivaroxaban doses in response to CYP3A4 induction or inhibition. In some embodiments, the present invention thus teaches that the concomitant administration of other drugs can alter CYP3A4 expression levels (via induction or repression). For example, some known inducers of CYP3A4 expression include drugs such as the glucocorticoid dexamethasone, the antibiotic rifampicin, and the antimycotic clotrimazole. Like the regulation of P-gp secretion however, the effect of any drug on CYP3A4 activity is difficult to predict.

In addition to metabolism by CYP3A4, 14% of rivaroxaban is metabolized by CYP2J2. It has been shown that verapamil can inhibit greater than 95% of metabolism by CYP2J2 in vitro, while erythromycin did not demonstrate significant inhibition of CYP2J2 activity. The clinical implications of the potential inhibition of CYP2J2-mediated metabolism of rivaroxaban by verapamil are as yet unknown.

Thus in some embodiments, the present disclosure is directed to methods of treating patients in need of Factor Xa inhibitor treatment, said method comprising adjusting rivaroxaban dosing (as described herein) in response to changes in a patient's altered liver drug metabolism.

Verapamil is a calcium channel blocker used in the treatment of angina, arrhythmia, and essential hypertension among other uses, for example as disclosed herein. Verapamil is extensively metabolized to a number of metabolites, at least one of which (norverapamil) retains significant activity and is itself a P-gp inhibitor. Approximately 70% is excreted in the urine (mainly as metabolites, but about 4% unchanged), and approximately 16% in the feces.

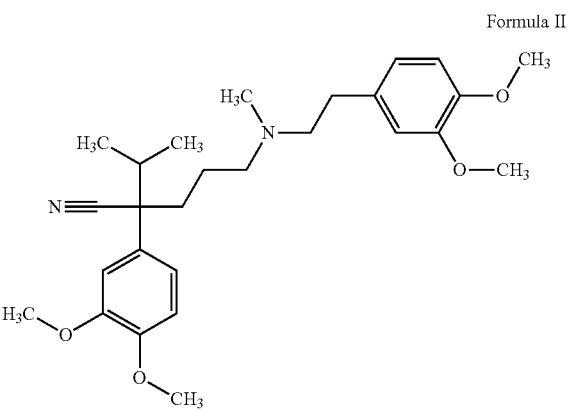

Formula II

Verapamil is a popular drug, used daily by millions of older patients with heart issues. The prevalent use of the drug has caused it to be listed in the World Health Organizations (WHO) list of essential medicines (found at http://www.who.int/medicines/publications/essentialmedicines/en/).

In some embodiments, the present disclosure is directed to treatment of a patient with a medical condition requiring treatment with a calcium channel blocker such as verapamil (in conjunction with a Factor Xa inhibitor), including management of essential hypertension, treatment of hypertension, treatment of pulmonary hypertension, prevention and treatment of recurrent and paroxysmal supraventricular tachycardia, management of supraventricular tachycardia, treatment of atrial tachycardia and junctional tachycardia, treatment of cerebral vasospasm, treatment of hypertrophic cardiomyopathy, treatment of chronic stable angina pectoris, treatment of unstable angina pectoris, management of Prinzmetal variant angina, ventricular rate control in atrial fibrillation/flutter, prevention of cluster headache, prevention of migraine, prevention of myocardial infarction in patients with preserved left ventricular function, management of manic manifestations of bipolar disorder, treatment of Raynaud's disease, treatment of coronary artery disease, treatment of subarachnoid hemorrhage, treatment of Dravet Syndrome, beta cell survival therapy in Type I diabetes, treatment of vestibular migraine, treatment of chronic subjective dizziness, treatment of erectile dysfunction, prevention of keloid recurrence, treatment of refractory epilepsy, treatment of refractory meningioma, treatment of chronic heart failure secondary to non-ischemic cardiomyopathy, treatment of relapsed or refractory Hodgkin lymphoma, treatment of Marfan Syndrome, treatment of treatment-resistant mania, prevention of kidney disease in diabetic patients, treatment of Metabolic Syndrome, and treatment of hypoglycemia following gastric bypass.

In particular, verapamil has become an effective treatment for atrial fibrillation and hypertension. Verapamil has been shown to prolong the effective refractory period within the atrioventricular (AV) node to slow AV conduction in a dose-dependent manner. This property accounts for the ability of verapamil to slow the ventricular rate in patients with chronic atrial flutter or atrial fibrillation, reducing the subjective sensation of palpitations. Verapamil has also been shown to relax the tone of the smooth muscle lining blood vessels and dilate the blood vessels. This property, among others, attributes to verapamil's utility as an antihypertensive agent. Typical daily doses of verapamil for such patients range from about 40 mg to about 480 mg, often divided in 3 to 4 equal doses during the day. Alternatively, extended release verapamil formulations can be administered once a day, in daily doses of 100 mg to 400 mg, (including 40 mg, 100 mg, 200 mg, 300 mg, and 400 mg). Verapamil is available in various dosage forms including without limitation extended-release capsules (100, 120, 180, 200, 240, 300, and 360 mg), extended-release tablets (120, 180, and 240 mg), immediate release tablets (40, 80, and 120 mg doses), IV solutions (5 mg/2 mL and 10 mg/4 mL), and as combination formulations (e.g., extended release trandolapril/verapamil HCl tablets, 1 mg/240 mg, 2 mg/180 mg, 2 mg/240 mg, 4 mg/240 mg). In some embodiments, when verapamil is administered as an extended-release capsule or an extended-release tablet, it is administered 1 or 2 times daily. In some embodiments, when verapamil is administered as an immediate-release tablet, it is administered 3 or 4 times daily.

Thus patients with atrial fibrillation are often prescribed verapamil to treat heart palpitations, and rivaroxaban to reduce the risk of stroke.

The present disclosure is at least partially based on the inventors' discovery that the concomitant administration of verapamil and rivaroxaban leads to an unexpectedly increased risk of rivaroxaban overdosing and adverse drug effects. Consequently, as a result of the increased rivaroxaban levels, patients concomitantly administered rivaroxaban, aspirin, and verapamil are at a significantly greater risk for major bleeding events. Without wishing to be bound by any one theory, the present inventors believe that administration of verapamil and rivaroxaban leads to an unexpected clinically significant drug-drug interaction that negatively impacts the metabolic and excretion clearance of rivaroxaban and can lead to increased adverse events, such as a major bleeding event. Because such patients are also being treated with aspirin, and the concomitant administration with rivaroxaban already presents a bleed risk to the patients, the dosing regimen must be appropriately adjusted for patients on verapamil. Thus, in at least some embodiments, the present invention is a method of reducing the side effects (increased bleeding, such as gastrointestinal or gastrointestinal bleeding) when verapamil and aspirin are coadministered with rivaroxaban, by adjusting the rivaroxaban dose to less than the currently recommended dose as described herein. In alternative embodiments, the present invention is a method of reducing the side effects (increased bleeding, such as gastrointestinal or intracranial bleeding) when verapamil and aspirin are coadministered with rivaroxaban, by administering a formulation which releases rivaroxaban such that the pharmacokinetic profile of rivaroxaban is similar (e.g., bioequivalent) to that of an identical patient not treated with verapamil and who is administered 2.5 mg rivaroxaban BID. In some embodiments, the rivaroxaban formulation can be an extended release formulation, an immediate release formulation, or a formulation comprising an instant release component and a delayed or extended release component.

For example, in certain embodiments, the rivaroxaban dose for a patient concomitantly administered rivaroxaban, aspirin, and verapamil is in the range of about 0.5 mg to less than about 2.5 mg, e.g., about 0.5 mg, about 0.75 mg, about 1.0 mg, about 1.25 mg, about 1.5 mg, about 1.75 mg, about 2.0 mg, and about 2.25 mg, inclusive of all values and subranges therebetween. In some such embodiments, the recommended rivaroxaban dose for a patient concomitantly administered rivaroxaban, aspirin, and verapamil is about 1.75 mg. In some other particular embodiments, such as when at least a portion of the dose of rivaroxaban is administered in a delayed release or extended release formulation, the rivaroxaban dose for a patient concomitantly administered rivaroxaban, aspirin, and verapamil is in the range of from about 0.5 mg to less than about 5 mg, e.g., about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, and about 4.75 mg, inclusive of all values and subranges therebetween.

Likewise, for any of the adjusted rivaroxaban doses enumerated above, the daily aspirin dose ranges from about 25 mg to about 400 mg, or about 75 mg to about 400 mg. In some embodiments, the aspirin is administered in multiple doses (e.g., from 2-12 daily doses). In some embodiments, the aspirin is administered once daily (e.g., a single 100 mg dose). For example the daily aspirin dose may be about 25, about 30, about 35, about 40, about 45, about 50, about 60, about 70, about 75, about 80, about 90, about 100, about 125, about 150, about 175, about 200, about 225, about 250, about 275, about 300, about 325, about 350, about 375, about 400 mg, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1550, about 1600, about 1650, about 1700, about 1750, about 1800, about 1850, about 1900, about 1950, about 2000, about 2050, about 2100, about 2150, about 2200, about 2250, about 2300, about 2350, about 2400, about 2450, about 2500, about 2550, about 2600, about 2650, about 2700, about 2750, about 2800, about 2850, about 2900, about 2950, about 3000, about 3050, about 3100, about 3150, about 3200, about 3250, about 3300, about 350, about 3400, about 3450, about 3500, about 3550, about 3600, about 3650, about 3700, about 3750, about 3800, about 3850, about 3900, about 3950, and about 4000 mg.

Likewise, for any of the adjusted rivaroxaban doses enumerated above, the daily verapamil dose ranges from about 100 mg to about 480 mg per day (e.g., about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg or about 480 mg), whether administered as a divided dose (e.g., 2-4 times daily) or a single extended release dose.

Verapamil is classified as an inhibitor of cytochrome P450 CYP3A4 and also as an inhibitor of the transporter permeability-glycoprotein (P-gp). Verapamil has been classified by the FDA as a moderate inhibitor of CYP3A4, but has less of an inhibitory effect on excretion of edoxaban, a similar Factor Xa inhibitor, than erythromycin, which is also viewed by the FDA as a moderate CYP3A4 inhibitor. Furthermore, erythromycin and verapamil are metabolized (cleared) from the body of a patient in substantially different ways. Erythromycin is mainly metabolized by demethylation in the liver by the CYP3A4 enzyme, and is eliminated primarily in the bile, with little renal excretion (2-15% unchanged drug). In contrast, as discussed above, verapamil undergoes extensive hepatic metabolism, and its metabolites are excreted primarily in the urine. Additionally, some metabolites (i.e., norverapamil and metabolite D-703) also have inhibitory potential toward P-gp (Pauli-Magnus C et al. "Characterization of the Major Metabolites of Verapamil as Substrates and Inhibitors of P-glycoprotein." *J Pharmacol Exp Ther* 2000;

293:376-382). The clinical relevance of inhibition of P-gp by the metabolites of verapamil is as yet unknown. Thus, verapamil and erythromycin are quite different in their respective metabolic characteristics, particularly renal clearance and the mechanisms by which they interact with P-gp, and thus studies of rivaroxaban/erythromycin co-administration would not be expected to provide clinical insights directly relevant to any drug-drug interactions between rivaroxaban and verapamil.

In some embodiments, the present disclosure teaches that the concomitant administration of verapamil leads to a reduction in the body's clearance (metabolism and excretion) of rivaroxaban. Moreover, atrial fibrillation is a disease associated with older patients, with a median age of about 70 years old, who may have age-related renal impairment. Thus in some embodiments, the present disclosure teaches that reduced rivaroxaban clearance due to concomitant administration of verapamil is also likely exacerbated by age-related impairment and/or renal impairment of patients receiving the drug.

Because of the drug-drug interaction between verapamil and rivaroxaban, the present disclosure teaches, in some embodiments, that the concomitant administration of verapamil with aspirin and rivaroxaban is associated with higher proportion of adverse events (such as major bleeding events), for example compared to otherwise identical (or the same) patient populations in which verapamil is not administered.

In some embodiments, the present disclosure teaches that rivaroxaban pharmacokinetics are at least partially affected by changes in a patient's CYP3A4 metabolism and P-gp secretion. The present disclosure demonstrates however, that general knowledge about the secretion and metabolism pathways of rivaroxaban are not sufficiently clear to predict whether any particular drug would have undesirable drug interaction(s) with rivaroxaban, or that such undesirable interaction(s) could be addressed effectively by the specific dose adjustments of rivaroxaban provided herein, rather than, e.g., eliminating one or both drugs from the patient's treatment. Indeed, the general knowledge in the art indicates that, except for strong combined CYP3A4/P-gp inhibitors, any noted change in rivaroxaban exposure is not clinically relevant, and coadministration of rivaroxaban and strong combined CYP3A4/P-gp inhibitors is to be avoided entirely.

This document has already described that P-gp inhibitors do not share any obvious structural characteristics that could be used to predict a drug's effect on P-gp secretion. Similarly (despite many structural modeling efforts), the molecular structure of a drug is not dispositive of a drug's effect on CYP3A4 inhibition. It would therefore be difficult, if not impossible, for a person having ordinary skill in the art to predict a drug's effect on liver metabolism or renal secretion solely based on its structure.

Moreover, as discussed below, in some embodiments, the present invention also teaches that even empirical evidence of a drug's inhibition of CYP3A4 metabolism and/or P-gp secretion, is still not predictive of whether the drug will have a clinically relevant effect on rivaroxaban exposure.

Previous studies have demonstrated that concomitant administration of other CYP3A4 and P-gp inhibitors did not produce clinically relevant effects on rivaroxaban exposure or the prevalence of adverse events. For example, other studies have shown that concomitant administration of rivaroxaban and erythromycin (a moderate CYP3A4 and strong P-gp inhibitor) produced a 34% rivaroxaban exposure increase. Similarly, concomitant administration of rivaroxaban with clarithromycin (another strong CYP3A4 inhibitor and moderate P-gp inhibitor) produced a 54% rivaroxaban exposure increase. The concomitant administration of rivaroxaban and fluconazole (a moderate CYP3A4 inhibitor) produced a 42% rivaroxaban exposure increase. Thus the present disclosure teaches that not all CYP3A4 and P-gp inhibitors exhibit clinically relevant drug-drug interactions with rivaroxaban.

Verapamil and erythromycin are also dosed quite differently. Erythromycin is an antibiotic useful for the treatment of various bacterial infections, and is usually administered for relatively short periods of time, e.g. 1-2 weeks. In contrast, verapamil is typically administered to treat chronic conditions such as hypertension, angina pectoris, cardiac arrhythmias, etc. and is administered over much longer periods of time. These conditions for which verapamil is administered are common comorbidities and indications that would also require treatment with rivaroxaban.

The present inventors observed that patients concomitantly administered verapamil and rivaroxaban represented 30% of the reported rivaroxaban serious bleeding adverse events, despite accounting for only 22% of the total population receiving rivaroxaban. This was unexpected in view of the teachings of the prior art which suggested no clinically relevant drug-drug interactions existed between verapamil and rivaroxaban. For example, Xarelto's® (rivaroxaban) own product insert concludes that concomitant use of rivaroxaban with verapamil did not result in increased patient bleeding (see ROCKET AF trial in section 7.5 of Xarelto® product insert (revised August/2016). Additionally, a poster presented on Nov. 8, 2015 at the American Heart Association 2015 Scientific Sessions concluded that use of non-dihydropyridine calcium channel blockers such as verapamil with rivaroxaban was not associated with an increased risk of non-major clinically relevant or major bleeding compared to subjects on non-dihydropyridine calcium channel blockers and warfarin (see Poster S4081—Efficacy and Safety of Rivaroxaban versus Warfarin in Patients Taking Non-dihydropyridine Calcium Channel Blockers: Results from the ROCKET-AF Trial, presented Nov. 8, 2015, American Heart Association, Scientific Sessions 2015, and published at http://www.abstractsonline.com/pp8/#!/3795/presentation/37668).

Moreover, the present disclosure also teaches that the increased incidence of adverse events was not common to all CYPA34 and P-gp inhibitors, but was rather unexpectedly specific to verapamil. For example, in some embodiments, the present disclosure teaches that concomitant administration of rivaroxaban and erythromycin (another moderate CYP3A4 inhibitor and strong P-gp inhibitor) is not associated with increased serious bleeding adverse events.

The present invention's discovery of the need to adjust the dose of rivaroxaban when coadministered with aspirin and verapamil was also unexpected based on, among other factors, the lack of any perceived clinically relevant drug-drug interactions between rivaroxaban and substrates of CYP enzymes (e.g., Mueck et al.), the expected weaker P-gp inhibition of verapamil compared to erythromycin, verapamil's previous history of safe concomitant administration with other anticoagulants, including other direct Factor Xa inhibitors. For example, previous studies reviewing the interaction between edoxaban (an oral direct Factor Xa inhibitor) and verapamil, concluded that their co-administration did not lead to any increased bleeding or other adverse events (Mendell et al., Drug-drug interaction studies of cardiovascular drugs involving p-glycoprotein, an efflux transporter, on the pharmacokinetics of edoxaban, an oral Factor Xa inhibitor. Am. J. Cardiovasc Drugs (2013)

13:331-342). Accordingly, the label for SAVAYSA™ (edoxaban) does not suggest reduced dosing for patients concomitantly administered with verapamil (SAVAYSA™ product insert, Highlights of prescribing information (revised September/2016), found at http://dsi.com/prescribing-information-portlet/getPIContent?productName=Savaysa). Moreover, the SAVAYSA™ product insert shows that concomitant administration of edoxaban and verapamil has a smaller impact on edoxaban exposure compared to concomitant administration edoxaban with erythromycin, as shown by the lower GMR values for the $C_{max}$ and AUC parameters of verapamil compared to erythromycin (e.g., FIG. 12.1 of the SAVAYSA™ product insert). Thus, to the extent edoxaban/verapamil coadministration may be predictive of the drug-drug interactions expected for coadministered rivaroxaban/verapamil, the effects of verapamil coadministration would be expected to be appreciably less than for erythromycin coadministration. However, the SAVAYSA™ product insert does not recommend dose adjustment of edoxaban when coadministered with either erythromycin or verapamil.

Similarly, the only clinically significant drug-drug interactions identified in the ELIQUIS® (apixaban) package insert (revised September/2015) are with strong dual CYP3A4 and P-gp inhibitors such as ketoconazole, itraconazole, and, and clarithromycin.

In addition, the dabigatran (PRADAXA®) label, another anticoagulant, states that interaction of dabigatran with various P-gp inhibitors (e.g., verapamil, amiodarone, quinidine, clarithromycin and ticagrelor) does not require a dose adjustment of PRADAXA®, and that this conclusion should not be extrapolated to other P-gp inhibitors, further indicating that P-gp inhibition is unpredictable and one of skill in the art would not use the study of a particular drug to directly inform dosing instructions for another drug. For this reason, studies of interactions between, for example, rivaroxaban and erythromycin is not a good predictor for interactions between e.g. rivaroxaban and verapamil.

Lastly, the betrixaban (BEVYXXA®) label, a recently approved anticoagulant, states that concomitant use of P-gp inhibitors, such as verapamil, results in increased exposure to betrixaban, and patients should reduce the dose of betrixaban (Section 7.1; revised June/2017). However, the respective labels indicate that rivaroxaban and betrixaban are treated quite differently clinically in the context of drug-drug interactions. More specifically, the betrixaban label recommends that patients concomitantly treated with ketoconazole should reduce the dose of betrixaban by 50%, whereas the rivaroxaban label contraindicates coadministration with ketoconazole. For patients concomitantly treated with clarithromycin, the betrixaban label recommends reducing the dose of betrixaban by 50%, whereas there is no clinically relevant drug-drug interaction reported for rivaroxaban and thus the full dose of rivaroxaban is administered. For patients concomitantly treated with carbamazepine, the betrixaban label does not report a clinically relevant drug-drug interaction and the full dose of betrixaban can be administered, whereas the rivaroxaban label contraindicates coadministration. Thus, the drug-drug interactions expected for coadministered rivaroxaban/verapamil would be expected to be entirely different than for betrixaban/verapamil.

In addition, to the extent that the Xarelto® (rivaroxaban) Package Insert indicates that concomitant use of combined P-gp and CYP3A4 inhibitors is contraindicated or should be avoided (due to reduced elimination of rivaroxaban), there are a number of known alternative anticoagulants, such as apixaban, edoxaban, or dabigatran, better safety and/or efficacy profiles in patients with reduced clearance. See for example Nielsen et al., Clin. Res. Cardiol. 22 Nov. 2014 (published online) which refers to apixaban as a first line choice for patients with impaired renal elimination due to its comparable efficacy and favorable safety profile.

The current FDA approved dosing scheme for rivaroxaban includes a once-daily 10-20 mg dose. Specifically, patients with nonvalvular atrial fibrillation, deep vein thrombosis, or pulmonary embolism, are recommended to take a once-daily 20 mg oral dose with the evening meal, while patients with deep vein thrombosis following hip or knee replacement surgery are recommended to take a once-daily 10 mg dose with or without food. Xarelto's® (rivaroxaban) product insert does not currently recommend a dose reduction with verapamil (https://www.xareltohcp.com/shared/product/xarelto/prescribing-information.pdf). In addition, clinical trials are investigating a dosing scheme of 2.5 mg of rivaroxaban in combination with a low dose aspirin to reduce the risk of cardiovascular events. Notably, however, these clinical trials have not investigated the impact of moderate CYP3A4 and P-gp inhibitors on the risk of major bleeding events because, prior to the Applicant's discovery, rivaroxaban was considered to have no clinically relevant drug-drug interaction with such moderate CYP3A4 and P-gp inhibitors.

In some embodiments, the present disclosure provides a method of treating a patient with rivaroxaban, comprising (a) administering about 100 to about 480 mg of verapamil daily to the patient; (b) administering about 75 mg to about 325 mg of aspirin to the patient; and (c) administering about 0.5 mg to about 2.5 mg of rivaroxaban to the patient. As described herein, the claimed range of rivaroxaban is critical to safely and effectively treat a disorder (e.g., a clotting disorder) while minimizing the patient's risk of a major bleeding event.

In some embodiments, the dose of verapamil administered in step (a) is 120, 240, 360, or 480 mg. For example, in some embodiments, the dose of verapamil administered in step (a) is 120 mg. In some embodiments, the dose of verapamil administered in step (a) is 240 mg. In some embodiments, the dose of verapamil administered in step (a) is 360 mg. In some embodiments, the dose of verapamil administered in step (a) is 480 mg.

In some embodiments, the dose of aspirin administered in step (b) is 75, 81, 100, 125, 150, 175, 200, 225, 250, 275, 300, or 325 mg. For example, in some embodiments, the dose of aspirin administered in step (b) is 100 mg.

In some embodiments, the dose of rivaroxaban administered in step (c) is about 0.5 mg to less than 2.5 mg of rivaroxaban. In some embodiments, the dose of rivaroxaban is administered in an immediate release or rapid release formulation. In some embodiments, the dose of rivaroxaban administered in step (c) ranges from about 0% to about 95% of the dose recommended for an otherwise identical patient who is not concomitantly administered and verapamil. In some embodiments, the dose of rivaroxaban administered in step (c) ranges from about 0.5 mg to about 2.0 mg (for example about 0.5 mg, about 0.75 mg, about 1.0 mg, about 1.25 mg, about 1.5 mg, about 1.75 mg, and about 2.0 mg).

In some embodiments, the patient is administered the dose of rivaroxaban twice daily (BID). In some embodiments, the total daily dose of rivaroxaban administered to the patient is less than 5 mg (e.g., the total daily dose of rivaroxaban administered to the patient is about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, or about 4.75 mg).

Thus in some embodiments, the present disclosure is directed to the administration of a reduced rivaroxaban dose, in which the reduced rivaroxaban dose is between about 0%-99.5% of the recommended dose for an otherwise identical (or the same) patient who is not concomitantly administered aspirin and verapamil, e.g., 0%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, 99%, or 99.5%, including all ranges therebetween.

In some embodiments, the patient is administered from about 0.5 mg to less than about 5 mg of rivaroxaban once daily, wherein at least a portion of the dose of rivaroxaban is administered in a delayed release or extended release component. In some embodiments, rivaroxaban is released at a rate such that the pharmacokinetic profile of rivaroxaban is similar (e.g., bioequivalent) to that of an identical patient not treated with verapamil who is administered 2.5 mg rivaroxaban BID. In some embodiments, the extended release or delayed release formulation comprises an immediate release component which has about 2.0 mg or less of rivaroxaban (e.g., from 0.5-2.0 mg, including 1.75 mg) and provides blood plasma levels of rivaroxaban that are similar (e.g., bioequivalent) to an otherwise identical patient treated with a single dose of 2.5 mg of rivaroxaban but who is not concomitantly administered verapamil. In some embodiments, after the blood plasma levels of rivaroxaban decrease, the extended release or delayed release component provides blood plasma levels of rivaroxaban that are similar (e.g., bioequivalent) to an otherwise identical patient treated with 2.5 mg of rivaroxaban BID but who is not concomitantly administered verapamil. The extended release or delayed release component can be appropriately formulated to account for residual blood plasma concentrations of rivaroxaban from the immediate release component so as to achieve safe blood plasma levels of rivaroxaban (e.g., less than those corresponding to 5 mg of rivaroxaban in an otherwise identical patient treated who is not concomitantly administered verapamil). In other embodiments, the extended release formulation releases rivaroxaban at a rate such that the pharmacokinetic profile of rivaroxaban is similar (e.g., bioequivalent) to that of an identical patient not treated with verapamil who is administered 2.5 mg rivaroxaban BID.

In some embodiments, the present disclosure is directed to a method of treating a patient in need of a Factor Xa inhibitor, said method comprising the step of administering one or more reduced rivaroxaban dose(s) (relative to the recommended dose for an otherwise identical (or the same) patient treated with aspirin but not concomitantly administered verapamil as described herein) of about 10 µg/Kg, 20 µg/Kg, 30 µg/Kg, 40 µg/Kg, 50 µg/Kg, 60 µg/Kg, 70 µg/Kg, 80 µg/Kg, 90 µg/Kg, 100 µs/Kg, 110 µg/Kg, 120 µg/Kg, 130 µg/Kg, 140 µg/Kg, 150 µg/Kg, 160 µg/Kg, 170 µg/Kg, 180 µg/Kg, 190 µg/Kg, 200 µg/Kg, 210 µg/Kg, 220 µg/Kg, 230 µg/Kg, 240 µg/Kg, 250 µg/Kg, 260 µg/Kg, 270 µg/Kg, 280 µg/Kg, 290 µg/Kg, 300 µg/Kg, 310 µg/Kg, 320 µg/Kg, 330 µg/Kg, 340 µg/Kg, 350 µg/Kg, 360 µg/Kg, 370 µg/Kg, 380 µg/Kg, 390 µg/Kg, 400 µg of rivaroxaban per Kilogram of body weight.

Thus in some embodiments, the present disclosure is directed to the administration of a reduced rivaroxaban dose, in which the reduced rivaroxaban dose (relative to the recommended dose for an otherwise identical (or the same) patient treated with aspirin but not concomitantly administered verapamil as described herein) is between about 10 µg/kg-300 µg/kg of body weight, inclusive of all ranges and subranges therebetween. For example, in some embodiments, the present disclosure is directed to the administration of a reduced rivaroxaban dose (relative to the recommended dose for an otherwise identical (or the same) treated with aspirin but not concomitantly administered verapamil as described herein), in which the reduced rivaroxaban dose is reduced to between about 100 µg/kg-150 µg/kg of body weight.

In various embodiments, the present disclosure is directed to a method of treating a patient with a reduced dose of rivaroxaban relative to the recommended dose of rivaroxaban for an otherwise identical (or the same) patient treated with aspirin but not concomitantly administered verapamil. Persons having skill in the art will readily recognize that that a clinically effective dose of rivaroxaban for a patient may be dependent on various factors including patient age, sex, body weight, disease progression, overall heath, pathological state, tolerance to the drug, dosing frequency, route of administration, etc. However, the "recommended dose" is the dose recommended in the art as suitable for a particular patient or patient population based on recognized, clinically relevant physical criteria as established during e.g. clinical trials upon which FDA approval is based. Thus in some embodiments, the present disclosure teaches that an "otherwise identical" patient who is not concomitantly administered verapamil is a patient that has substantially identical physical and biophysical characteristics as the treated patient, other than the administration of verapamil. Thus in some embodiments, an identical patient could be an experimental control patient in studies evaluating the reduced rivaroxaban dosing treatments of the present disclosure. In some embodiments, the recommended dose is 2.5 mg of rivaroxaban administered twice daily (BID).

In the methods of the present disclosure, the rivaroxaban can be administered by any suitable method or mode. For example the compound of the formula (I) can be administered in various forms as described herein, e.g., capsules, tablets, oral solutions or suspensions, dry powders, or parenteral dosage forms such as injectable or IV solutions or suspensions.

Dosing Regimens

In some embodiments, the present disclosure is directed to methods of treating a patient in need of treatment with a Factor Xa inhibitor and who is concomitantly administered aspirin and verapamil, wherein said method comprises administering more than one dose of rivaroxaban per day. Thus in some embodiments the present disclosure is directed to methods of administering, 1, 2, or 3 doses of rivaroxaban per day. In some embodiments, the present disclosure is directed to administering 2 daily doses of rivaroxaban with food. In various of these embodiments, said multiple doses are reduced doses according to the present disclosure. In some embodiments, the patient is administered the dose of rivaroxaban twice daily. In some embodiments, the total daily dose of rivaroxaban administered to the patient is less than 5 mg. In some embodiments, the total daily dose of rivaroxaban administered to the patient is about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, or about 4.75 mg.

The present disclosure contemplates a variety of dosing regimens. For example, the present disclosure encompasses all combinations of dosing rivaroxaban (e.g., 1 or 2 or more times daily), verapamil (i.e., 1, 2, 3, or 4 or more times daily), and aspirin (i.e., 1, 2, 3, 4, 5, 6, 7, 8, 9, or 10 or more times daily). Typical daily doses of verapamil for such patients range from about 40 mg to about 480 mg, often divided in 3 to 4 equal doses during the day. Alternatively, extended release verapamil formulations can be administered once a day, in daily doses of 100 mg to 400 mg, (including 40 mg, 100 mg, 200 mg, 300 mg, and 400 mg). Verapamil is available in various dosage forms including without limitation extended-release capsules (100, 120, 180, 200, 240, 300, and 360 mg), extended-release tablets (120, 180, and 240 mg), immediate release tablets (40, 80, and 120 mg doses), IV solutions (5 mg/2 mL and 10 mg/4 mL), and as combination formulations (e.g., extended release trandolapril/verapamil HCl tablets, 1 mg/240 mg, 2 mg/180 mg, 2 mg/240 mg, 4 mg/240 mg).

Thus, in some embodiments, verapamil is administered to a patient once daily at any dose (e.g., 100, 120, 180, 200, 240, 300, or 360 mg). Accordingly, in some embodiments, when verapamil is administered to a patient once daily, rivaroxaban may be administered once daily and aspirin may be administered once daily. In some embodiments, when verapamil is administered to a patient once daily, rivaroxaban may be administered twice daily and aspirin may be administered once daily.

In some embodiments, verapamil is administered to a patient twice daily at any dose (e.g., 100, 120, 180, 200, or 240 mg in an extended release formulation). Accordingly, in some embodiments, when verapamil is administered to a patient twice daily, rivaroxaban may be administered once daily and aspirin may be administered once daily. In some embodiments, when verapamil is administered to a patient twice daily, rivaroxaban may be administered twice daily and aspirin may be administered once daily.

In some embodiments, verapamil is administered to a patient three times daily (e.g., 100 or 120 mg in an extended release formulation). Accordingly, in some embodiments, when verapamil is administered to a patient three times daily, rivaroxaban may be administered once daily and aspirin may be administered once daily. In some embodiments, when verapamil is administered to a patient three times daily, rivaroxaban may be administered twice daily and aspirin may be administered once daily.

In some embodiments, verapamil is administered to a patient four times daily (e.g., 100 or 120 mg in an extended release formulation). Accordingly, in some embodiments, when verapamil is administered to a patient four times daily, rivaroxaban may be administered once daily and aspirin may be administered once daily. In some embodiments, when verapamil is administered to a patient four times daily, rivaroxaban may be administered twice daily and aspirin may be administered once daily.

In some embodiments, the present disclosure is directed to treating a patient in need of treatment with rivaroxaban and aspirin, wherein the patient is not concomitantly administered verapamil (i.e., the coadministration of rivaroxaban and verapamil is contraindicated for such patients). That is, in some embodiments disclosed herein, the patient administered rivaroxaban in combination with aspirin, or verapamil in combination with aspirin, but not both rivaroxaban and verapamil. In some embodiments, the present methods are directed to treating a patient in need of treatment with rivaroxaban and who is concomitantly administered aspirin and verapamil, wherein the patient ceases verapamil and then is administered rivaroxaban. In alternative embodiments, the patient is currently being treated with rivaroxaban and aspirin but is need of treatment with verapamil; the patient ceases treatment with rivaroxaban and then is administered verapamil. In various embodiments, the patient has normal renal function, or in other embodiments, the patient has renal insufficiency (mild, moderate or severe as described herein)

Thus, in some embodiments, the patient is administered rivaroxaban in combination with aspirin, but not verapamil. In other embodiments, the patient is administered verapamil in combination with aspirin, but not rivaroxaban. In accordance with these embodiments, in order to transition a patient treated with verapamil to rivaroxaban, a patient a delay period of about 1-21 days between ceasing administration of verapamil and starting administration of the rivaroxaban is required in order to avoid or reduce the incidence of side effects resulting from administration of the verapamil. For example, the delay period may be about 1, 2, 3, 4, 5, 6, 7, 8, 9, 10, 11, 12, 13, 14, 15, 16, 17, 18, 19, 20, or 21 days. After the delay period, rivaroxaban may be administered as described herein or at the reference dose. In some embodiments, the patient is mildly renally impaired. In some embodiments, the patient is moderately renally impaired. In some embodiments, the patient is severely renally impaired. In accordance with any of these embodiments, after the washout period, the patient may take a reduced dose of verapamil. After the delay period, rivaroxaban is administered as described herein or at the reference dose. In accordance with any of these embodiments, after the delay period, the patient may take a reduced dose of rivaroxaban. For example, the reduced rivaroxaban dose is about 0%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, 99%, or 99.5% of the rivaroxaban dose recommended for an otherwise identical (or the same)

patient who is not concomitantly administered aspirin and verapamil, including all ranges therebetween.

Pharmacokinetic and Pharmacodynamic Characteristics

As discussed above, in various embodiments, the disclosure provides for methods of treating a patient with an immediate or rapid release formulation comprising from about 0.5 mg to less than about 2.5 mg of rivaroxaban. In some embodiments, the present disclosure provides a method of treating a patient with rivaroxaban, wherein after administering the dose of rivaroxaban, the patient has at least one of the following characteristics: (i) a geometric mean of an area under the plasma concentration-time curve (AUC) of rivaroxaban in the range of from about 80% of about 165.4 µg·h/L to about 125% of about 551.9 µg·h/L after a single dose of rivaroxaban in the range of from about 0.5 mg to less than about 2.5 mg; (ii) a geometric mean of a maximum blood plasma concentration (Cmax) of rivaroxaban in the range of from about 80% of 28.6 µg/L to about 125% of 103.0 µg/L after a single dose of rivaroxaban in the range of from about 0.5 mg to less than about 2.5 mg; (iii) a risk of major bleeding of no more than about 4.5%; or (iv) a prothrombin time of 20-30 seconds. For example, in some embodiments, after administering the dose of rivaroxaban, the patient has one of the aforementioned characteristics. In some embodiments, after administering the dose of rivaroxaban, the patient has two of the aforementioned characteristics. In some embodiments, after administering the dose of rivaroxaban, the patient has three of the aforementioned characteristics. In some embodiments, after administering the dose of rivaroxaban, the patient has four of the aforementioned characteristics.

In some embodiments, the present disclosure provides a method of treating a patient with an immediate or rapid release formulation comprising from about 0.5 mg to less than about 2.5 mg of rivaroxaban, wherein after administering the dose of rivaroxaban, the patient has at least one of the following characteristics: (i) a geometric mean AUC of rivaroxaban that is less than 1064.25 µg·h/L after a single dose of rivaroxaban in the range of from about 0.5 mg to less than about 2.5 mg; and (ii) a geometric mean Cmax of rivaroxaban that is less than 181.25 µg/L after a single dose of rivaroxaban in the range of from about 0.5 mg to less than about 2.5 mg; (iii) a risk of major bleeding of no more than about 4.5%; or (iv) a prothrombin time of 20-30 seconds. For example, in some embodiments, after administering the dose of rivaroxaban, the patient has one of the aforementioned characteristics. In some embodiments, after administering the dose of rivaroxaban, the patient has two of the aforementioned characteristics. In some embodiments, after administering the dose of rivaroxaban, the patient has three of the aforementioned characteristics. In some embodiments, after administering the dose of rivaroxaban, the patient has four of the aforementioned characteristics.

In some embodiments, the patient who is administered a reduced amount of the recommended dose of rivaroxaban, as described herein, experiences the same or lower $C_{max}$ of rivaroxaban compared to the otherwise identical (or the same) patient who is administered the recommended dose of rivaroxaban and aspirin but is not concomitantly administered verapamil. Thus, in some embodiments, the present disclosure is directed to administering a reduced rivaroxaban dose (relative to the recommended dose for an otherwise identical (or the same) patient treated with aspirin but not concomitantly administered verapamil as described herein), wherein the rivaroxaban $C_{max}$ (including the $C_{max}$ measured after a single dose and steady state $C_{max}$, $C_{max\ ss}$) of said patient for the inventive dosing regimen is less than about 200 µg/L, about 195 µg/L, about 190 µg/L, about 185 µg/L, about 180 µg/L, about 175 µg/L, about 170 µg/L, about 165 µg/L, about 160 µg/L, about 158 µg/L, about 155 µg/L, about 150 µg/L, about 145 µg/L, about 140 µg/L, about 135 µg/L, about 130 µg/L, about 125 µg/L, about 120 µg/L, about 115 µg/L, about 110 µg/L, about 105 µg/L, about 100 µg/L, about 95 µg/L, about 90 µg/L, about 85 µg/L, about 80 µg/L, about 75 µg/L, about 70 µg/L, about 65 µg/L, about 60 µg/L, about 55 µg/L, about 50 µg/L, about 45 µg/L, about 40 µg/L, about 35 µg/L, about 30 µg/L, about 25 µg/L, and about 20 µg/L, inclusive of all ranges and subranges therebetween.

In some embodiments, the present disclosure is directed to the administration of a reduced rivaroxaban dose (relative to the recommended dose for an otherwise identical (or the same) patient treated with aspirin but not concomitantly administered verapamil as described herein), in which the reduced rivaroxaban dose produces a rivaroxaban $C_{max}$ (including $C_{max}$ measured after a single dose and steady state $C_{max}$, $C_{max\ ss}$) between about from about 80% of 28.6 µg/L to about 125% of 103.0 µg/L, e.g., about 20 µg/L, about 25 µg/L, about 30 µg/L, about 35 µg/L, about 40 µg/L, about 45 µg/L, about 50 µg/L, about 55 µg/L, about 60 µg/L, about 65 µg/L, about 70 µg/L, about 75 µg/L, about 80 µg/L, about 85 µg/L, about 90 µg/L, about 95 µg/L, about 100 µg/L, about 105 µg/L, about 110 µg/L, about 115 µg/L, about 120 µg/L, about 125 µg/L, and about 130 µg/L, inclusive of all values and subranges therebetween.

In some embodiments, the reduced rivaroxaban dose provides the same or lower AUC of rivaroxaban compared to an otherwise identical (or the same) patient who is receiving the recommended rivaroxaban dose and aspirin but is not concomitantly administered verapamil. Thus, in some embodiments, the present disclosure is directed to the administration of a reduced rivaroxaban dose (relative to the recommended dose for an otherwise identical (or the same) patient not concomitantly administered verapamil as described herein), wherein the rivaroxaban AUC (include AUC measured after a single dose, and $AUC_{inf}$ or $AUC_{ss}$) of said patient is lower than about 150 (µg/L)·h, about 175 (µg/L)·h, about 200 (µg/L)·h, about 225 (µg/L)·h, about 250 (µg/L)·h, about 275 (µg/L)·h, about 300 (µg/L)·h, about 325 (µg/L)·h, about 350 (µg/L)·h, about 375 (µg/L)·h, about 400 (µg/L)·h, about 425 (µg/L)·h, about 450 (µg/L)·h, about 475 (µg/L)·h, about 500 (µg/L)·h, about 525 (µg/L)·h, about 550 (µg/L)·h, about 575 (µg/L)·h, about 600 (µg/L)·h, about 625 (µg/L)·h, 650 (µg/L)·h, about 675 (µg/L)·h, about 700 (µg/L)·h, about 725 (µg/L)·h, about 750 (µg/L)·h, about 775 (µg/L)·h, about 800 (µg/L)·h, about 825 (µg/L)·h, about 850 (µg/L)·h, about 875 (µg/L)·h, about 900 (µg/L)·h, about 925 (µg/L)·h, about 950 (µg/L)·h, about 975 (µg/L)·h, about 1000 (µg/L)·h, about 1025 (µg/L)·h, about 1050 (µg/L)·h, or about 1064.25 (µg/L)·h, inclusive of all ranges and subranges therebetween.

Thus in some embodiments, the present disclosure is directed to the administration of a reduced rivaroxaban dose (relative to the recommended dose for an otherwise identical (or the same) patient treated with aspirin but not concomitantly administered verapamil as described herein), in which the reduced rivaroxaban dose provides an AUC between about 80% of about 165.4 µg·h/L to about 125% of about 551.9 µg·h/L after a single dose of rivaroxaban, e.g., 150 (µg/L)·h, about 175 (µg/L)·h, about 200 (µg/L)·h, about 225 (µg/L)·h, about 250 (µg/L)·h, about 275 (µg/L)·h, about 300 (µg/L)·h, about 325 (µg/L)·h, about 350 (µg/L)·h, about 375 (µg/L)·h, about 400 (µg/L)·h, about 425 (µg/L)·h, about 450 (µg/L)·h, about 475 (µg/L)·h, about 500 (µg/L)·h, about 525 (µg/L)·h, about 550 (µg/L)·h, about 575 (µg/L)·h, about 600

(μg/L)·h, about 625 (μg/L)·h, about 650 (μg/L)·h, about 675 (μg/L)·h, and about 700 (μg/L)·h, inclusive of all ranges and subranges therebetween.

In some embodiments, the present disclosure is directed to methods of reducing the rivaroxaban dose of patients who are concomitantly administered aspirin and verapamil (relative to the recommended dose for an otherwise identical (or the same) patient treated with aspirin but not concomitantly administered verapamil as described herein), wherein the reduced dose causes the patient to maintain the approximately the same maximum prothrombin time compared to an otherwise identical (or the same) patient who is not concomitantly administered verapamil and is receiving the recommended dose of rivaroxaban. Thus in some embodiments, the present disclosure is directed to a reduced rivaroxaban dose (relative to the recommended dose for an otherwise identical (or the same) patient treated with aspirin but not concomitantly administered verapamil as described herein), wherein the patient's maximum prothrombin time is lower than about 20 s, 21 s, 22 s, 23 s, 24 s, 25 s, 26 s, 27 s, 28 s, 29 s, or about 30 s.

In some embodiments, the present disclosure is directed to methods of reducing the rivaroxaban dose of patients who are concomitantly administered aspirin and verapamil (relative to the recommended dose for an otherwise identical (or the same) patient treated with aspirin but not concomitantly administered verapamil as described herein), wherein the reduced dose of rivaroxaban provides a % risk of major bleeding, for example using the relation shown in FIG. 5, which is less than about 12%, less than about 11%, less than about 10%, less than about 9%, less than about 8%, less than about 7%, less than about 6%, less than about 5%, less than about 4.5%, less than about 4%, less than about 3.5%, less than about 3%, less than about 2.5%, less than about 2%, less than about 1.5%, or less than about 1%. In some embodiments, the patient's risk of a major bleeding event is less than about 5%. In still other embodiments, said patients hereinabove may have normal renal function, or mild, moderate, or severe renal impairment.

In some embodiments, the present disclosure is directed to methods of reducing the rivaroxaban dose of patients with mild renal impairment relative to the recommended dose for an otherwise identical patient having normal renal function, wherein the reduced dose of rivaroxaban provides a % risk of major bleeding, for example using the relation shown in FIG. 5, which is less than about 12%, less than about 11%, less than about 10%, less than about 9%, less than about 8%, less than about 7%, less than about 6%, less than about 5%, less than about 4.5%, less than about 4%, less than about 3.5%, less than about 3%, less than about 2.5%, less than about 2%, less than about 1.5%, or less than about 1%. In some embodiments, the patient's risk of a major bleeding event is less than about 5%.

As discussed above, in various embodiments, the disclosure provides for methods of treating a patient, once daily, with a delayed or extended release component comprising from about 1.75 mg to less than about 5.0 mg of rivaroxaban. In some such embodiments, the present disclosure provides a method of treating a patient with rivaroxaban, wherein after administering the dose of rivaroxaban, the patient has at least one of the following characteristics: (i) a geometric mean of an area under the plasma concentration-time curve (AUC) of rivaroxaban that is within the range of about 80%-125% of the AUC measured for an otherwise identical patient that was administered 2.5 mg of rivaroxaban, BID, but was not administered verapamil; (ii) a geometric mean of a maximum blood plasma concentration (Cmax) of rivaroxaban in the range of from about 80% of 28.6 μg/L to about 125% of 103.0 μg/L; (iii) a risk of major bleeding of no more than about 4.5%; or (iv) a prothrombin time of 20-30 seconds. For example, in some embodiments, after administering the dose of rivaroxaban, the patient has one of the aforementioned characteristics. In some embodiments, after administering the dose of rivaroxaban, the patient has two of the aforementioned characteristics. In some embodiments, after administering the dose of rivaroxaban, the patient has three of the aforementioned characteristics. In some embodiments, after administering the dose of rivaroxaban, the patient has four of the aforementioned characteristics.

In some embodiments, the present disclosure provides a method of treating a patient, once daily, with a delayed or extended release formulation comprising from about 2.5 mg to less than about 5.0 mg of rivaroxaban, wherein after administering the dose of rivaroxaban, the patient has at least one of the following characteristics: (i) a geometric mean of an area under the plasma concentration-time curve (AUC) of rivaroxaban that is less than the AUC measured for an otherwise identical patient that was administered 5.0 mg of rivaroxaban, twice daily, but was not administered verapamil; and (ii) a geometric mean Cmax of rivaroxaban that is less than 181.25 μg/L; (iii) a risk of major bleeding of no more than about 4.5%; or (iv) a prothrombin time of 20-30 seconds. For example, in some embodiments, after administering the dose of rivaroxaban, the patient has one of the aforementioned characteristics. In some embodiments, after administering the dose of rivaroxaban, the patient has two of the aforementioned characteristics. In some embodiments, after administering the dose of rivaroxaban, the patient has three of the aforementioned characteristics. In some embodiments, after administering the dose of rivaroxaban, the patient has four of the aforementioned characteristics.

In some embodiments, the patient experiences a $C_{max}$ of rivaroxaban that is the same or lower than the $C_{max}$ of an otherwise identical (or the same) patient who is administered the recommended dose of rivaroxaban and aspirin but is not concomitantly administered verapamil. Thus, in some embodiments, the rivaroxaban $C_{max}$ (including the $C_{max}$ measured after a single dose and steady state $C_{max}$, $C_{max\ ss}$) of said patient is less than about 200 μg/L, about 195 μg/L, about 190 μg/L, about 185 μg/L, about 180 μg/L, about 175 μg/L, about 170 μg/L, about 165 μg/L, about 160 μg/L, about 158 μg/L, about 155 μg/L, about 150 μg/L, about 145 μg/L, about 140 μg/L, about 135 μg/L, about 130 μg/L, about 125 μg/L, about 120 μg/L, about 115 μg/L, about 110 μg/L, about 105 μg/L, about 100 μg/L, about 95 μg/L, about 90 μg/L, about 85 μg/L, about 80 μg/L, about 75 μg/L, about 70 μg/L, about 65 μg/L, about 60 μg/L, about 55 μg/L, about 50 μg/L, about 45 μg/L, about 40 μg/L, about 35 μg/L, about 30 μg/L, about 25 μg/L, and about 20 μg/L, inclusive of all ranges and subranges therebetween.

In some embodiments, the $C_{max}$ (including $C_{max}$ measured after a single dose and steady state $C_{max}$, $C_{max\ ss}$) is between about from about 80% of 28.6 μg/L to about 125% of 103.0 μg/L, e.g., about 20 μg/L, about 25 μg/L, about 30 μg/L, about 35 μg/L, about 40 μg/L, about 45 μg/L, about 50 μg/L, about 55 μg/L, about 60 μg/L, about 65 μg/L, about 70 μg/L, about 75 μg/L, about 80 μg/L, about 85 μg/L, about 90 μg/L, about 95 μg/L, about 100 μg/L, about 105 μg/L, about 110 μg/L, about 115 μg/L, about 120 μg/L, about 125 μg/L, and about 130 μg/L, inclusive of all values and subranges therebetween.

In some embodiments, the dose of rivaroxaban in the extended or delayed release formulation provides the same or lower AUC of rivaroxaban compared to an otherwise identical (or the same) patient who is receiving the recommended rivaroxaban dose and aspirin but is not concomitantly administered verapamil. Thus, in some embodiments, a patient treated according to the present methods will have a geometric mean of an area under the plasma concentration-time curve (AUC) of rivaroxaban that is within the range of about 80%-125% of the AUC measured for an otherwise identical patient that was administered 2.5 mg of rivaroxaban, BID, but was not administered verapamil—i.e., within the range of 80% of 330.8 to 125% of 1103.8. In some embodiments, the rivaroxaban AUC (include AUC measured after a single dose, and $AUC_{inf}$ or $AUC_{ss}$) of said patient is lower than about 150 (μg/L)·h, about 175 (μg/L)·h, about 200 (μg/L)·h, about 225 (μg/L)·h, about 250 (μg/L)·h, about 264.64 (μg/L)·h, about 275 (μg/L)·h, about 300 (μg/L)·h, about 325 (μg/L)·h, about 350 (μg/L)·h, about 375 (μg/L)·h, about 400 (μg/L)·h, about 425 (μg/L)·h, about 450 (μg/L)·h, about 475 (μg/L)·h, about 500 (μg/L)·h, about 525 (μg/L)·h, about 550 (μg/L)·h, about 575 (μg/L)·h, about 600 (μg/L)·h, about 625 (μg/L)·h, 650 (μg/L)·h, about 675 (μg/L)·h, about 700 (μg/L)·h, about 725 (μg/L)·h, about 750 (μg/L)·h, about 775 (μg/L)·h, about 800 (μg/L)·h, about 825 (μg/L)·h, about 850 (μg/L)·h, about 875 (μg/L)·h, about 900 (μg/L)·h, about 925 (μg/L)·h, about 950 (μg/L)·h, about 975 (μg/L)·h, about 1000 (μg/L)·h, about 1025 (μg/L)·h, about 1050 (μg/L)·h, about 1064.25 (μg/L)·h, about 1075 (μg/L)·h, about 1100 (μg/L)·h, about 1125 (μg/L)·h, about 1150 (μg/L)·h, about 1175 (μg/L)·h, about 1200 (μg/L)·h, about 1225 (μg/L)·h, about 1250 (μg/L)·h, about 1275 (μg/L)·h, about 1300 (μg/L)·h, about (μg/L)·h, about 1325 (μg/L)·h, about 1350 (μg/L)·h, about 1375 (μg/L)·h, or about 1379.75 (μg/L)·h, inclusive of all ranges and subranges there between.

In some embodiments, the patient has an AUC that is less than the AUC measured for an otherwise identical patient that was administered 5.0 mg of rivaroxaban, twice daily, but was not administered verapamil, e.g., less than about 2,759.5 (μg/L)·h, less than about 2,750 (μg/L)·h, less than about 2,725 (μg/L)·h, less than about 2,700 (μg/L)·h, less than about 2,675 (μg/L)·h, less than about 2,650 (μg/L)·h, less than about 2,625 (μg/L)·h, less than about 2,600 (μg/L)·h, less than about 2,575 (μg/L)·h, less than about 2,550 (μg/L)·h, less than about 2,525 (μg/L)·h, less than about 2,500 (μg/L)·h, less than about 2,475 (μg/L)·h, less than about 2,450 (μg/L)·h, less than about 2,425 (μg/L)·h, less than about 2,400 (μg/L)·h, less than about 2,375 (μg/L)·h, less than about 2,350 (μg/L)·h, less than about 2,325 (μg/L)·h, less than about 2,300 (μg/L)·h, less than about 2,275 (μg/L)·h, less than about 2,250 (μg/L)·h, less than about 2,225 (μg/L)·h, less than about 2,200 (μg/L)·h, less than about 2,175 (μg/L)·h, less than about 2,150 (μg/L)·h, less than about 2,125 (μg/L)·h, less than about 2,100 (μg/L)·h, less than about 2,075 (μg/L)·h, less than about 2,050 (μg/L)·h, less than about 2,025 (μg/L)·h, less than about 2,000 (μg/L)·h, less than about 1,975 (μg/L)·h, less than about 1,950 (μg/L)·h, less than about 1,925 (μg/L)·h, less than about 1,900 (μg/L)·h, less than about 1,875 (μg/L)·h, less than about 1,850 (μg/L)·h, less than about 1,825 (μg/L)·h, less than about 1,800 (μg/L)·h, less than about 1,775 (μg/L)·h, less than about 1,750 (μg/L)·h, less than about 1,725 (μg/L)·h, less than about 1,700 (μg/L)·h, less than about 1,675 (μg/L)·h, less than about 1,650 (μg/L)·h, less than about 1,625 (μg/L)·h, less than about 1,600 (μg/L)·h, less than about 1,575 (μg/L)·h, less than about 1,550 (μg/L)·h, less than about 1,525 (μg/L)·h, less than about 1,500 (μg/L)·h, less than about 1,475 (μg/L)·h, less than about 1,450 (μg/L)·h, less than about 1,425 (μg/L)·h, less than about 1,400 (μg/L)·h, less than about 1,375 (μg/L)·h, less than about 1,350 (μg/L)·h, less than about 1,325 (μg/L)·h, less than about 1,300 (μg/L)·h, less than about 1,275 (μg/L)·h, less than about 1,250 (μg/L)·h, less than about 1,225 (μg/L)·h, less than about 1,200 (μg/L)·h, less than about 1,175 (μg/L)·h, less than about 1,150 (μg/L)·h, less than about 1,125 (μg/L)·h, less than about 1,100 (μg/L)·h, less than about 1,075 (μg/L)·h, less than about 1,050 (μg/L)·h, less than about 1,025 (μg/L)·h, less than about 1,000 (μg/L)·h, less than about 975 (μg/L)·h, less than about 950 (μg/L)·h, less than about 925 (μg/L)·h, less than about 900 (μg/L)·h, less than about 875 (μg/L)·h, less than about 850 (μg/L)·h, less than about 825 (μg/L)·h, less than about 800 (μg/L)·h, less than about 775 (μg/L)·h, less than about 750 (μg/L)·h, less than about 725 (μg/L)·h, less than about 700 (μg/L)·h, less than about 675 (μg/L)·h, less than about 650 (μg/L)·h, less than about 625 (μg/L)·h, less than about 600 (μg/L)·h, less than about 575 (μg/L)·h, less than about 550 (μg/L)·h, less than about 525 (μg/L)·h, less than about 500 (μg/L)·h, less than about 475 (μg/L)·h, less than about 450 (μg/L)·h, less than about 425 (μs/L)·h, or less than about 400 (μg/L)·h.

In some embodiments, the present disclosure is directed to methods of reducing the rivaroxaban dose of patients who are concomitantly administered aspirin and verapamil (relative to the recommended dose for an otherwise identical (or the same) patient treated with aspirin but not concomitantly administered verapamil as described herein), wherein the reduced dose causes the patient to maintain the approximately the same maximum prothrombin time compared to an otherwise identical (or the same) patient who is not concomitantly administered verapamil and is receiving the recommended dose of rivaroxaban. Thus in some embodiments, the present disclosure is directed to a reduced rivaroxaban dose (relative to the recommended dose for an otherwise identical (or the same) patient treated with aspirin but not concomitantly administered verapamil as described herein), wherein the patient's maximum prothrombin time is lower than about 20 s, 21 s, 22 s, 23 s, 24 s, 25 s, 26 s, 27 s, 28 s, 29 s, or about 30 s.

In some embodiments, the present disclosure is directed to methods of reducing the rivaroxaban dose of patients who are concomitantly administered aspirin and verapamil (relative to the recommended dose for an otherwise identical (or the same) patient treated with aspirin but not concomitantly administered verapamil as described herein), wherein the reduced dose of rivaroxaban provides a % risk of major bleeding, for example using the relation shown in FIG. 5, which is less than about 12%, less than about 11%, less than about 10%, less than about 9%, less than about 8%, less than about 7%, less than about 6%, less than about 5%, less than about 4.5%, less than about 4%, less than about 3.5%, less than about 3%, less than about 2.5%, less than about 2%, less than about 1.5%, or less than about 1%. In some embodiments, the patient's risk of a major bleeding event is less than about 5%. In still other embodiments, said patients hereinabove may have normal renal function, or mild, moderate, or severe renal impairment.

In some embodiments, the present disclosure is directed to methods of reducing the rivaroxaban dose of patients with mild renal impairment relative to the recommended dose for an otherwise identical patient having normal renal function, wherein the reduced dose of rivaroxaban provides a % risk of major bleeding, for example using the relation shown in FIG. 5, which is less than about 12%, less than about 11%, less than about 10%, less than about 9%, less than about 8%, less than about 7%, less than about 6%, less than about 5%, less than about 4.5%, less than about 4%, less than about 3.5%, less than about 3%, less than about 2.5%, less than about 2%, less than about 1.5%, or less than about 1%. In some embodiments, the patient's risk of a major bleeding event is less than about 5%.

Thus in some embodiments, the present disclosure is directed to the administration of a reduced rivaroxaban dose (relative to the recommended dose for an otherwise identical (or the same) patient treated with aspirin but not concomitantly administered verapamil as described herein), in which the reduced rivaroxaban dose causes said patient to exhibit a maximum a prothrombin time between about 20 s-30 s, inclusive of all ranges and subranges therebetween. For example, in some embodiments, the present disclosure is directed to the administration of a reduced rivaroxaban dose (relative to the recommended dose for an otherwise identical (or the same) patient treated with aspirin but not concomitantly administered verapamil as described herein), in which the reduced rivaroxaban dose produces a maximum prothrombin time between about 20 s-30 s.

Indications

The present disclosure is also directed to a method of treating a patient in need of treatment with a Factor Xa inhibitor, an NSAID (such as aspirin), and a calcium channel blocker (such as verapamil), wherein the treatment is to decrease the risk of major cardiovascular events (death, myocardial infarction, or stroke) in patients with chronic coronary and/or peripheral artery disease; reduce the risk of acute limb ischemia in patients with peripheral artery disease; decrease the risk of major cardiovascular events (death, myocardial infarction, or stroke) in patients with acute coronary syndrome; and prevention and treatment of venous thromboembolism (also referred to as cancer-associated venous thromboembolism) in cancer patients or patients with active cancer. In some embodiments, the method can include administering a daily dose of about 100, 120, 180, 240 300, 360, or about 480 mg verapamil, a dose of aspirin (e.g., about 75 mg to about 325 mg), and a reduced dose of rivaroxaban (as described herein). In some embodiments, the patient has mild, moderate, or severe renal impairment.

The present disclosure is also directed to a method of treating a person in need of a calcium channel blocker comprising administering a dose of aspirin (e.g., about 75 mg to about 325 mg, e.g., about 100 mg), a dose of verapamil (100, 120, 180, 240 300, 360, or about 480 mg), and a dose of rivaroxaban which is less than the dose recommended for an otherwise identical (or the same) patient who is not concomitantly administered verapamil. In some embodiments, the calcium channel blocker indicated for the treatment of essential hypertension or atrial fibrillation. In some embodiments, the method can include administering a daily dose of about 100, 120, 180, 240, about 360, or about 480 mg of verapamil, including all ranges and subranges therebetween to the patient, administering a dose of aspirin (e.g., about 75 mg to about 325 mg) and administering a dose of rivaroxaban as described herein. In some embodiments, the patient can have mild, moderate, or severe renal impairment and is in need of anticoagulant therapy.

In some embodiments, the methods described herein can prevent major adverse cardiac events. In some embodiments, the adverse cardiac events can include, but are not limited to cardiovascular death, myocardial infarction and stroke. In some embodiments, the methods can be used to prevent stroke and systemic embolism in adult patients. In some embodiments, the patients have non-valvular atrial fibrillation (AF) with one or more risk factors. In some embodiments, the methods can be used to prevent or treat pulmonary embolism (PE) in adults. In some embodiments, the methods can be used to prevent or treat deep vein thrombosis (DVT) in adults. In some embodiments, the methods can be used to concurrently prevent or treat recurrent deep vein thrombosis (DVT) and pulmonary embolism (PE) in adults. In some embodiments, the methods can be used to prevent or treat venous thromboembolism (VTE) in adult patients. In other embodiments, the adult patients undergo elective hip replacement surgery.

In some embodiments, the methods can be used to prevent or treat venous thromboembolism (VTE) in adult patients. In other embodiments, the adult patients undergo elective knee replacement surgery. In some embodiments, the methods can be used to prevent or treat atherothrombotic events. In some embodiments, the atherothrombotic events can include but are not limited to cardiovascular death, myocardial infarction or stroke. In some embodiments, the prevention or treatment can be after an Acute Coronary Syndrome in adult patients. In some embodiments, the adult patients have elevated cardiac biomarkers. In other embodiments, the adult patients have no prior stroke or transient ischaemic attack (TIA) when co-administered with acetylsalicylic acid (ASA) alone (ASA is also known as aspirin). In some embodiments, the adult patients have no prior stroke or transient ischaemic attack (TIA) when co-administered with acetylsalicylic acid (ASA) plus clopidogrel. In some embodiments, the adult patients have no prior stroke or transient ischaemic attack (TIA) when co-administered with acetylsalicylic acid (ASA) plus ticlopidine.

Renal Status

In any of the various embodiments disclosed herein, the patient who is concomitantly administered rivaroxaban, aspirin, and verapamil can have normal renal function.

In any of the various embodiments disclosed herein, the patient who is concomitantly administered rivaroxaban, aspirin, and verapamil can be mildly renally impaired.

In any of the various embodiments disclosed herein, the patient who is concomitantly administered rivaroxaban, aspirin, and verapamil can have moderate renal impairment.

In any of the various embodiments disclosed herein, the patient who is concomitantly administered rivaroxaban, aspirin, and verapamil can have severe renal impairment.

In some embodiments, the patient has a $CL_{Cr}$ of less than or equal to about 89 mL/min. In some embodiments, the patient has a $CL_{Cr}$ of less than or equal to about 79 mL/min. In some embodiments, the patient has a $CL_{Cr}$ of 60-89 mL/min. In some embodiments, the patient has a $CL_{Cr}$ of 30-59 mL/min. In some embodiments, the patient has a $CL_{Cr}$ of 15-29 mL/min.

EMBODIMENTS

1. A method of treating a patient in need of treatment with rivaroxaban, comprising:
(a) administering about 100 to about 480 mg of verapamil daily to the patient;
(b) administering about 75 mg to about 325 mg of aspirin to the patient; and
(c) administering about 0 mg to less than about 5 mg of rivaroxaban to the patient.

2. The method of embodiment 1, wherein the dose of verapamil administered in step (a) is 120, 240, 360, or 480 mg.

3. The method of embodiment 1, wherein the dose of aspirin administered in step (b) is 100 mg.

4. The method of embodiment 3, wherein the patient is administered 100 mg of aspirin once daily.

5. The method of embodiment 1, wherein the patient is administered 2.5 mg of rivaroxaban once daily, wherein at least a portion of the 2.5 mg dose of rivaroxaban is administered in a delayed release or extended release formulation.

6. The method of embodiment 1, wherein the dose of rivaroxaban administered in step (c) is about 0.5 mg to less than 2.5 mg of rivaroxaban.

7. The method of embodiment 6, wherein the dose of rivaroxaban is administered in an immediate release or rapid release formulation.

8. The method of embodiment 1, wherein the dose of rivaroxaban administered in step (c) ranges from about 15% to about 95% of the dose recommended for an otherwise identical patient who is not concomitantly administered verapamil.

9. The method of embodiments 1, 6, 7, or 8, wherein the dose of rivaroxaban administered in step (c) ranges from about 0.5 mg to about 2.0 mg.

10. The method of any of embodiments 1 or 6-9, wherein the dose of rivaroxaban administered in step (c) is selected from the group consisting of about 0.5 mg, about 0.75 mg, about 1.0 mg, about 1.25 mg, about 1.5 mg, about 1.75 mg, and about 2.0 mg.

11. The method of any of embodiments 1 or 6-10, wherein the patient is administered the dose rivaroxaban twice daily.

12. The method of any of embodiments 1-11, wherein the total daily dose of rivaroxaban administered to the patient is less than 5 mg.

13. The method of embodiment 12, wherein the total daily dose of rivaroxaban administered to the patient is about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, or about 4.75 mg.

14. The method of embodiment 1, wherein the dose of rivaroxaban administered in step (c) is 0 mg.

15. The method of embodiment 1, wherein after administering the dose of rivaroxaban, the patient has at least one of the following characteristics:
   (i) a geometric mean of an area under the plasma concentration-time curve (AUC) of rivaroxaban in the range of from about 80% of about 165.4 µg·h/L to about 125% of about 551.9 µg·h/L after a single dose of rivaroxaban;
   (ii) a geometric mean of a maximum blood plasma concentration (Cmax) of rivaroxaban in the range of from about 80% of 28.6 µg/L to about 125% of 103.0 µg/L after a single dose of rivaroxaban;
   (iii) a risk of major bleeding of no more than about 4.5%; or
   (iv) a prothrombin time of 20-30 seconds.

16. The method of embodiment 1, wherein after administering the dose of rivaroxaban, the patient has at least one of the following characteristics:
   (i) a geometric mean AUC of rivaroxaban that is less than 1064.25 µg·h/L after a single dose of rivaroxaban; and
   (ii) a geometric mean Cmax of rivaroxaban that is less than 181.25 µg/L after a single dose of rivaroxaban;
   (iii) a risk of major bleeding of no more than about 4.5%; or
   (iv) a prothrombin time of 20-30 seconds.

17. The method of embodiment 1, wherein the patient is treated for a disease or condition selected from the group consisting of: decreasing the risk of major cardiovascular events (death, myocardial infarction, or stroke) in patients with chronic coronary and/or peripheral artery disease, reducing the risk of acute limb ischemia in patients with peripheral artery disease, decreasing the risk of major cardiovascular events (death, myocardial infarction, or stroke) in patients with acute coronary syndrome, and preventing and treating venous thromboembolism in cancer patients or patients with active cancer (also referred to as cancer-associated venous thromboembolism).

18. The method of any of embodiments 1-13 and 15-17, wherein the patient experiences an increase in the risk of internal bleeding of no more than about 5% compared to an otherwise identical patient that was administered aspirin alone.

19. The method of any of embodiments 1-13 and 15-18, wherein the patient's risk of a major bleeding event is less than about 5%.

20. The method of any of embodiments 1-13 and 15-19, and the efficacy in treating the condition is similar to the efficacy observed for the same condition in an otherwise identical patient that was treated with 2.5 mg of rivaroxaban but was not treated with verapamil.

21. The method of embodiment 1, wherein the patient is not renally impaired.

22. The method of embodiment 1, wherein the patient is mildly to severely renally impaired.

23. The method of embodiment 22, wherein the patient is mildly renally impaired.

24. The method of embodiment 22, wherein the patient is moderately renally impaired.

25. The method of embodiment 22, wherein the patient is severely renally impaired.

26. The method of embodiment 1, wherein the patient has a $CL_{Cr}$ of less than or equal to about 89 mL/min.

27. The method of embodiment 1, wherein the patient has a $CL_{Cr}$ of less than or equal to about 79 mL/min.

28. The method of embodiment 1, wherein the patient has a $CL_{Cr}$ of 60-89 mL/min.

29. The method of embodiment 1, wherein the patient has a $CL_{Cr}$ of 30-59 mL/min.

30. The method of embodiment 1, wherein the patient has a $CL_{Cr}$ of 15-29 mL/min.

EXAMPLES

Example 1. Oral Verapamil and Rivaroxaban Drug-Drug Interaction

This example illustrates the drug-drug interaction that occurs when a patient is concomitantly administered verapamil and rivaroxaban, which approximately doubles the patient's exposure to rivaroxaban. That is, this study shows that the pharmacokinetic parameters of a patient administered 20 mg of rivaroxaban in combination with verapamil are approximately equal those of a patient that was administered 40 mg of rivaroxaban in the absence of verapamil. Therefore, a patient that is co-administered 2.5 mg of rivaroxaban with verapamil would actually have the pharmacokinetic profile of a 5 mg dose of rivaroxaban.

A volunteer patient trial using both healthy and mildly renally impaired subjects is conducted in order to assess the pharmacokinetic and pharmacodynamic consequences of rivaroxaban and verapamil concomitant administration. This initial study is a non-randomized, open label controlled study of the rivaroxaban-verapamil drug-drug interaction.

During the initial portion of the study, patients are administered a single 20 mg dose of rivaroxaban with their breakfast without co-administration of verapamil. These patients are subjected to various one-time and longitudinal pharmacokinetic (PK) and pharmacodynamic (PD) analyses. Patient plasma levels of rivaroxaban are tracked for at least 72 hours after receiving a rivaroxaban dose. $C_{max}$ and AUC values for each dose are calculated. Patients also undergo a general physical exam to determine overall health and well-being.

Additional pharmacodynamic metrics are also gathered for each patient, including, but not limited to: prothrombin time (using the STA® Neoplastin® method) and Factor Xa activity. Protocols for each of these analyses have been described in Nielsen et al 2015. Renal Function and non-vitamin K oral anticoagulants in comparison with warfarin on safety and efficacy outcomes in atrial fibrillation patients: a systemic review and meta-regression analysis. Clin Res Cardiol May 104(5): 418-429).

During the second portion of the study, patients are administered a verapamil dose of 180 mg on Day 8, 240 mg on Day 9, and 360 mg on Days 10-15 to achieve steady state plasma concentrations of verapamil. On Day 15, patients will receive 360 mg verapamil together with the 20 mg rivaroxaban doses described for the initial portion of the study. All the pharmacokinetic and pharmacodynamics analyses are repeated on patients receiving this treatment.

PK and PD results for the rivaroxaban single treatment and rivaroxaban-verapamil concomitant treatment are compared to determine the safety profile of the resulting rivaroxaban doses.

The results show that concomitant administration of verapamil with rivaroxaban produces higher rivaroxaban plasma concentrations, prolonged PT, and increased Factor Xa inhibition.

Example 2. Pharmacokinetics and Plasma Rivaroxaban Concentrations in Subjects with Mild Renal Impairment and Normal Renal Function To estimate the effect of steady-state verapamil on the pharmacokinetics, pharmacodynamics, and safety of rivaroxaban, a study was conducted on subjects with either mild renal impairment or normal renal function. Subjects with either mild renal impairment or with normal renal function were enrolled. Subjects received a single 20 mg dose of rivaroxaban ("Period I") on the first day of the study, and after a washout period, a single 20 mg dose of rivaroxaban and a 360 mg dose of verapamil at steady state ("Period III").

Renal function of the subjects was determined by measuring creatinine clearance ($CL_{Cr}$) rates. Subjects who had $CL_{Cr} \geq 90$ mL/min were categorized as having normal renal function whereas subjects who had $CL_{Cr}$ 50-79 mL/min were categorized as mildly renally impaired. Blood samples were collected and processed according to the standard protocols. Plasma rivaroxaban concentrations were measured on Day 1 of the study at 0.5, 1, 2, 3, 4, 6, 8, and 12 hours, Day 2 at 24 and 36 hours, Day 3 at 48 hours, and Day 4 at 72 hours and are shown in Tables 1A-8 below.

TABLE 1A

Plasma Rivaroxaban Concentration-Time Data and Summary Statistics for Treatment Period I Separated by Renal Function Group (PK Analysis Set) Group 1: Mild Renal Impairment, (N = 14)

| | Time Point | | | | | | |
|---|---|---|---|---|---|---|---|
| Subject | Day 1, 0 hr | Day 1, 0.5 hr | Day 1, 1 hr | Day 1, 2 hr | Day 1, 3 hr | Day 1, 4 hr | Day 1, 6 hr |
| 1101 | 0 | 83.8 | 151 | 251 | 241 | 218 | 114 |
| 1102 | 0 | 207 | 278 | 207 | 197 | 204 | 161 |
| 1103 | 0 | 170 | 187 | 185 | 196 | 181 | 126 |
| 1104 | 0 | 235 | 218 | 184 | 199 | 182 | 119 |
| 1106 | 0 | 24.0 | 153 | 232 | 238 | 172 | 172 |
| 1108 | 0 | 174 | 168 | 170 | 297 | 344 | 274 |
| 1110 | 0 | 201 | 306 | 248 | 206 | 219 | 157 |
| 1111 | 0 | 245 | 247 | 211 | 268 | 247 | 164 |
| 1114 | 0 | 215 | 308 | 232 | 184 | 192 | 103 |
| 1115 | 0 | 170 | 133 | 187 | 215 | 190 | 133 |
| 1116 | 0 | 130 | 132 | 120 | 97.9 | 90.6 | 55.7 |
| 1118 | 0 | 326 | 448 | 333 | 315 | 316 | 128 |
| 2101 | 0 | 208 | 217 | 208 | 176 | 165 | 114 |
| 2104 | 0 | 23.4 | 25.7 | 40.6 | 55.8 | 79.6 | 232 |
| n | 14 | 14 | 14 | 14 | 14 | 14 | 14 |
| n < LLOQ | 14 | 0 | 0 | 0 | 0 | 0 | 0 |
| CV % | NC | 48.8 | 48.3 | 33.4 | 33.6 | 35.7 | 37.3 |
| AM | 0 | 172 | 212 | 201 | 206 | 200 | 147 |
| SD | 0 | 84.0 | 102 | 66.9 | 69.2 | 71.5 | 54.6 |
| Median | 0 | 188 | 202 | 208 | 202 | 191 | 130 |
| Minimum | 0 | 23.4 | 25.7 | 40.6 | 55.8 | 79.6 | 55.7 |
| Maximum | 0 | 326 | 448 | 333 | 315 | 344 | 274 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
BLQ values are treated as zero.
NC = Not calculated
Values expressed in µg/L
CV % = (SD/Mean) × 100, where SD and mean are standard deviation and arithmetic mean of untransformed data.
Summary statistics for Day 1, 0 hr are based on greater than 30% imputed values.
n < LLOQ = Number of BLQs imputed as zero.

TABLE 1B

Plasma Rivaroxaban Concentration-Time Data and Summary Statistics for Treatment Period I Separated by Renal Function Group (PK Analysis Set) Group 1: Mild Renal Impairment, (N = 14)

| | Time Point | | | | | |
|---|---|---|---|---|---|---|
| Subject | Day 1, 8 hr | Day 1, 12 hr | Day 2, 24 hr | Day 2, 36 hr | Day 3, 48 hr | Day 4, 72 hr |
| 1101 | 76.8 | 52.9 | 36.5 | 14.9 | 8.49 | 0 |
| 1102 | 131 | 84.9 | 53.7 | 10.0 | 9.67 | 0 |
| 1103 | 124 | 61.5 | 52.9 | 8.92 | 0 | 0 |
| 1104 | 89.5 | 38.8 | 41.9 | 10.8 | 6.49 | 0 |
| 1106 | 157 | 92.7 | 19.9 | 12.1 | 6.13 | 0 |
| 1108 | 221 | 132 | 50.3 | 17.9 | 11.4 | 0 |
| 1110 | 143 | 89.1 | 52.5 | 21.7 | 17.0 | 0 |
| 1111 | 125 | 72.7 | 38.6 | 18.5 | 15.5 | 0 |
| 1114 | 66.4 | 66.8 | 39.1 | 14.8 | 6.71 | 0 |
| 1115 | 122 | 103 | 33.9 | 11.2 | 0 | 0 |
| 1116 | 47.6 | 29.4 | 10.1 | 0 | 0 | 0 |
| 1118 | 102 | 49.9 | 42.2 | 21.5 | 21.4 | 12.2 |
| 2101 | 90.2 | 51.9 | 21.1 | 7.44 | 7.10 | 0 |
| 2104 | 223 | 97.7 | 18.0 | 0 | 0 | 0 |
| n | 14 | 14 | 14 | 14 | 14 | 14 |
| n < LLOQ | 0 | 0 | 0 | 2 | 4 | 13 |
| CV % | 42.2 | 38.7 | 39.1 | 56.1 | 86.2 | 374 |
| AM | 123 | 73.1 | 36.5 | 12.1 | 7.85 | 0.871 |
| SD | 51.8 | 28.3 | 14.3 | 6.80 | 6.77 | 3.26 |
| Median | 123 | 69.8 | 38.8 | 11.6 | 6.90 | 0 |

TABLE 1B-continued

Plasma Rivaroxaban Concentration-Time Data and Summary Statistics for Treatment Period I Separated by Renal Function Group (PK Analysis Set)
Group 1: Mild Renal Impairment, (N = 14)

| Subject | Day 1, 8 hr | Day 1, 12 hr | Day 2, 24 hr | Day 2, 36 hr | Day 3, 48 hr | Day 4, 72 hr |
|---|---|---|---|---|---|---|
| Minimum | 47.6 | 29.4 | 10.1 | 0 | 0 | 0 |
| Maximum | 223 | 132 | 53.7 | 21.7 | 21.4 | 12.2 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
BLQ values are treated as zero.
Values expressed in µg/L
CV % = (SD/Mean) × 100, where SD and mean are standard deviation and arithmetic mean of untransformed data.
Summary statistics for Day 4, 72 hr are based on greater than 30% imputed values.
n < LLOQ = Number of BLQs imputed as zero.

TABLE 2A

Plasma Rivaroxaban Concentration-Time Data and Summary Statistics for Treatment Period I Separated by Renal Function Group Excluding Outlier Sample (PK Analysis Set)
Group 2: Normal Renal Function, (N = 13)

| Subject | Day 1, 0 hr | Day 1, 0.5 hr | Day 1, 1 hr | Day 1, 2 hr | Day 1, 3 hr | Day 1, 4 hr | Day 1, 6 hr |
|---|---|---|---|---|---|---|---|
| 01105 | 0 | 107 | 160 | 187 | 290 | 336 | 230 |
| 01107 | 0 | 194 | 252 | 229 | 242 | 297 | 172 |
| 01109 | 0 | 117 | 249 | 204 | 307 | 276 | 162 |
| 01112 | 0 | 71.8 | 175 | 195 | 183 | 169 | 119 |
| 01113 | 0 | 169 | 178 | 163 | 183 | 148 | 91.9 |
| 01117 | 0 | 429 | 297 | 195 | 164 | 155 | 116 |
| 01119 | 0 | 197 | 175 | 208 | 263 | 352 | 180 |
| 01120 | 0 | 60.3 | 214 | 196 | 211 | 187 | 131 |
| 01121 | 0 | 218 | 195 | 151 | 133 | 115 | 67.5 |
| 02102 | 0 | 67.1 | 142 | 212 | 202 | 171 | 142 |
| 02103 | 0 | 129 | 214 | 201 | 230 | 183 | 133 |
| 02105 | 0 | 43.4 | 104 | 188 | 245 | 292 | 256 |
| 02106 | 0 | 26.2 | 80.5 | 141 | 215 | 266 | 218 |
| n | 13 | 13 | 13 | 13 | 13 | 13 | 13 |
| n < LLOQ | 13 | 0 | 0 | 0 | 0 | 0 | 0 |
| CV % | NC | 75.9 | 32.0 | 13.1 | 22.4 | 34.8 | 35.5 |
| AM | 0 | 141 | 187 | 190 | 221 | 227 | 155 |
| SD | 0 | 107 | 59.9 | 24.8 | 49.5 | 78.8 | 55.1 |
| Median | 0 | 117 | 178 | 195 | 215 | 187 | 142 |
| Minimum | 0 | 26.2 | 80.5 | 141 | 133 | 115 | 67.5 |
| Maximum | 0 | 429 | 297 | 229 | 307 | 352 | 256 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
% CVb = 100 * SQRT [ex[(S^2) − 1]], where S is the standard deviation of the data on a log scale.
BLQ values are treated as zero.
NC = Not calculated
Values expressed in µg/L
Summary statistics for Day 1, 0 hr are based on greater than 30% imputed values.
n < LLOQ = Number of BLQs imputed as zero.

TABLE 2B

Plasma Rivaroxaban Concentration-Time Data and Summary Statistics for Treatment Period I Separated by Renal Function Group Excluding Outlier Sample (PK Analysis Set)
Group 2: Normal Renal Function, (N = 13)

| Subject | Day 1, 8 hr | Day 1, 12 hr | Day 2, 24 hr | Day 2, 36 hr | Day 3, 48 hr | Day 4, 72 hr |
|---|---|---|---|---|---|---|
| 01105 | 202 | 94.7 | 27.1 | 9.61 | 0 | 0 |
| 01107 | 114 | 72.3 | 25.1 | 5.30 | 0 | 0 |
| 01109 | 138 | 110 | 23.8 | 0 | 0 | 0 |
| 01112 | 88.9 | 53.9 | 20.0 | 6.02 | 0 | 0 |
| 01113 | 71.5 | 26.5 | 21.3 | 7.48 | 0 | 0 |
| 01117 | 104 | 47.3 | 32.0 | 20.6 | 14.3 | 0 |
| 01119 | 138 | 77.3 | 24.3 | 7.19 | 93.1† | 0 |
| 01120 | 114 | 50.7 | 17.3 | 5.98 | 0 | 0 |
| 01121 | 52.7 | 38.0 | 19.4 | 9.86 | 7.00 | 0 |
| 02102 | 109 | 66.6 | 22.6 | 5.26 | 0 | 0 |
| 02103 | 134 | 42.6 | 16.6 | 8.97 | 5.53 | 0 |
| 02105 | 183 | 91.9 | 25.2 | 8.16 | 5.53 | 0 |
| 02106 | 150 | 86.9 | 35.4 | 12.4 | 8.51 | 0 |
| n | 13 | 13 | 13 | 13 | 12 | 13 |
| n < LLOQ | 0 | 0 | 0 | 1 | 7 | 13 |
| CV % | 33.7 | 38.2 | 22.7 | 58.0 | 139 | NC |
| AM | 123 | 66.1 | 23.9 | 8.22 | 3.41 | 0 |
| SD | 41.4 | 25.3 | 5.42 | 4.76 | 4.75 | 0 |
| Median | 114 | 66.6 | 23.8 | 7.48 | 0 | 0 |
| Minimum | 52.7 | 26.5 | 16.6 | 0 | 0 | 0 |
| Maximum | 202 | 110 | 35.4 | 20.6 | 14.3 | 0 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
% CVb = 100 * SQRT [ex[(S^2) − 1]], where S is the standard deviation of the data on a log scale.
BLQ values are treated as zero.
NS = No sample; NC = Not calculated
Values expressed in µg/L
†Outlier sample excluded from summary statitics
Summary statistics for Day 3, 48 hr, Day 4, 72 hr are based on greater than 30% imputed values.
n < LLOQ = Number of BLQs imputed as zero.

TABLE 3A

Plasma Rivaroxaban Concentration-Time Data and Summary Statistics for Treatment Period III Separated by Renal Function Group (PK Analysis Set)
Group 1: Mild Renal Impairment, (N = 11)

| Subject | Day 1, 0 hr | Day 1, 0.5 hr | Day 1, 1 hr | Day 1, 2 hr | Day 1, 3 hr | Day 1, 4 hr | Day 1, 6 hr |
|---|---|---|---|---|---|---|---|
| 1101 | 0 | 154 | 211 | 196 | 238 | 247 | 154 |
| 1103 | 0 | 203 | 293 | 300 | 285 | 257 | 188 |
| 1104 | 0 | 278 | 260 | 268 | 276 | 214 | 164 |
| 1106 | 0 | 10.2 | 42.6 | 109 | 213 | 280 | 233 |
| 1108 | 0 | 158 | 192 | 263 | 303 | 303 | 269 |
| 1111 | 0 | 242 | 272 | 278 | 280 | 327 | 285 |
| 1114 | 0 | 249 | 218 | 279 | 250 | 226 | 170 |
| 1116 | 0 | 185 | 192 | 191 | 203 | 242 | 124 |
| 1118 | 0 | 349 | 387 | 429 | 429 | 458 | 209 |
| 2101 | 0 | 202 | 190 | 149 | 134 | 160 | 99.7 |
| 2104 | 0 | 136 | 113 | 132 | 117 | 126 | 135 |
| n | 11 | 11 | 11 | 11 | 11 | 11 | 11 |
| n < LLOQ | 11 | 0 | 0 | 0 | 0 | 0 | 0 |
| CV % | NC | 44.4 | 42.2 | 39.1 | 34.3 | 34.1 | 32.1 |
| AM | 0 | 197 | 216 | 236 | 248 | 258 | 185 |
| SD | 0 | 87.5 | 91.0 | 92.1 | 85.1 | 88.1 | 59.2 |
| Median | 0 | 202 | 211 | 263 | 250 | 247 | 170 |

TABLE 3A-continued

Plasma Rivaroxaban Concentration-Time Data and Summary Statistics for Treatment Period III Separated by Renal Function Group (PK Analysis Set)
Group 1: Mild Renal Impairment, (N = 11)

| | Time Point | | | | | | |
|---|---|---|---|---|---|---|---|
| Subject | Day 1, 0 hr | Day 1, 0.5 hr | Day 1, 1 hr | Day 1, 2 hr | Day 1, 3 hr | Day 1, 4 hr | Day 1, 6 hr |
| Minimum | 0 | 10.2 | 42.6 | 109 | 117 | 126 | 99.7 |
| Maximum | 0 | 349 | 387 | 429 | 429 | 458 | 285 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
BLQ values are treated as zero.
NC = Not calculated
Values expressed in µg/L
CV % = (SD/Mean) × 100, where SD and mean are standard deviation and arithmetic mean of untransformed data.
Summary statistics for Day 1, 0 hr are based on greater than 30% imputed values.
n < LLOQ = Number of BLQs imputed as zero.

TABLE 3B

Plasma Rivaroxaban Concentration-Time Data and Summary Statistics for Treatment Period III Separated by Renal Function Group (PK Analysis Set)
Group 1: Mild Renal Impairment, (N = 11)

| | Time Point | | | | | |
|---|---|---|---|---|---|---|
| Subject | Day 1, 8 hr | Day 1, 12 hr | Day 2, 24 hr | Day 2, 36 hr | Day 3, 48 hr | Day 4, 72 hr |
| 1101 | 125 | 77.7 | 36.0 | 11.1 | 8.48 | 0 |
| 1103 | 148 | 96.0 | 61.9 | 20.2 | 11.1 | 0 |
| 1104 | 194 | 88.6 | 45.5 | 25.0 | 12.9 | 8.27 |
| 1106 | 251 | 145 | 34.8 | 21.6 | 8.48 | 0 |
| 1108 | 222 | 154 | 78.5 | 33.0 | 27.4 | 10.6 |
| 1111 | 268 | 159 | 76.8 | 29.1 | 23.0 | 9.37 |
| 1114 | 126 | 55.4 | 27.6 | 14.2 | 17.0 | 8.69 |
| 1116 | 106 | 67.7 | 30.0 | 13.9 | 8.27 | 0 |
| 1118 | 179 | 134 | 68.5 | 34.9 | 31.2 | 13.1 |
| 2101 | 78.5 | 75.8 | 62.2 | 31.1 | 14.7 | 0 |
| 2104 | 118 | 95.0 | 46.6 | 27.0 | 19.1 | 7.48 |
| n | 11 | 11 | 11 | 11 | 11 | 11 |
| n < LLOQ | 0 | 0 | 0 | 0 | 0 | 5 |
| CV % | 37.8 | 35.4 | 36.2 | 34.5 | 47.9 | 99.6 |
| AM | 165 | 104 | 51.7 | 23.7 | 16.5 | 5.23 |
| SD | 62.3 | 37.0 | 18.7 | 8.19 | 7.91 | 5.21 |
| Median | 148 | 95.0 | 46.6 | 25.0 | 14.7 | 7.48 |
| Minimum | 78.5 | 55.4 | 27.6 | 11.1 | 8.27 | 0 |
| Maximum | 268 | 159 | 78.5 | 34.9 | 31.2 | 13.1 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
BLQ values are treated as zero.
Values expressed in µg/L
CV % = (SD/Mean) × 100, where SD and mean are standard deviation and arithmetic mean of untransformed data.
Summary statistics for Day 4, 72 hr are based on greater than 30% imputed values.
n < LLOQ = Number of BLQs imputed as zero.

TABLE 4A

Plasma Rivaroxaban Concentration-Time Data and Summary Statistics for Treatment Period III Separated by Renal Function Group (PK Analysis Set)
Group 2: Normal Renal Function, (N = 10)

| | Time Point | | | | | | |
|---|---|---|---|---|---|---|---|
| Subject | Day 1, 0 hr | Day 1, 0.5 hr | Day 1, 1 hr | Day 1, 2 hr | Day 1, 3 hr | Day 1, 4 hr | Day 1, 6 hr |
| 1105 | 0 | 179 | 185 | 208 | 267 | 383 | 268 |
| 1107 | 0 | 179 | 159 | 220 | 331 | 296 | 303 |
| 1109 | 0 | 198 | 236 | 302 | 264 | 292 | 205 |
| 1112 | 0 | 151 | 163 | 160 | 163 | 143 | 116 |
| 1119 | 0 | 148 | 206 | 314 | 314 | 348 | 287 |
| 1120 | 0 | 131 | 137 | 236 | 260 | 257 | 202 |
| 1121 | 0 | 178 | 201 | 208 | 178 | 154 | 103 |
| 2102 | 0 | 125 | 141 | 225 | 220 | 224 | 193 |
| 2103 | 0 | 214 | 269 | 232 | 225 | 201 | 177 |
| 2106 | 0 | 50.9 | 122 | 284 | 310 | 394 | 227 |
| n | 10 | 10 | 10 | 10 | 10 | 10 | 10 |
| n < LLOQ | 10 | 0 | 0 | 0 | 0 | 0 | 0 |
| CV % | NC | 29.9 | 25.7 | 19.9 | 22.4 | 33.2 | 32.0 |
| AM | 0 | 155 | 182 | 239 | 253 | 269 | 208 |
| SD | 0 | 46.4 | 46.7 | 47.6 | 56.8 | 89.5 | 66.6 |
| Median | 0 | 164 | 174 | 228 | 262 | 274 | 204 |
| Minimum | 0 | 50.9 | 122 | 160 | 163 | 143 | 103 |
| Maximum | 0 | 214 | 269 | 314 | 331 | 394 | 303 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
BLQ values are treated as zero.
NC = Not calculated
Values expressed in µg/L
CV % = (SD/Mean) × 100, where SD and mean are standard deviation and arithmetic mean of untransformed data.
Summary statistics for Day 1, 0 hr are based on greater than 30% imputed values.
n < LLOQ = Number of BLQs imputed as zero.

TABLE 4B

Plasma Rivaroxaban Concentration-Time Data and Summary Statistics for Treatment Period III Separated by Renal Function Group (PK Analysis Set)
Group 2: Normal Renal Function, (N = 10)

| | Time Point | | | | | |
|---|---|---|---|---|---|---|
| Subject | Day 1, 8 hr | Day 1, 12 hr | Day 2, 24 hr | Day 2, 36 hr | Day 3, 48 hr | Day 4, 72 hr |
| 1105 | 197 | 85.9 | 42.3 | 13.3 | 5.04 | 0 |
| 1107 | 182 | 121 | 41.3 | 11.7 | 6.36 | 0 |
| 1109 | 143 | 110 | 42.5 | 17.4 | 10.8 | 0 |
| 1112 | 94.9 | 78.7 | 50.9 | 12.3 | 8.87 | 0 |
| 1119 | 262 | 145 | 27.3 | 8.79 | 0 | 0 |
| 1120 | 119 | 62.8 | 27.4 | 8.99 | 0 | 0 |
| 1121 | 73.9 | 50.8 | 27.1 | 14.8 | 12.2 | 0 |
| 2102 | 160 | 102 | 48.4 | 19.5 | 10.7 | 0 |
| 2103 | 248 | 98.4 | 40.6 | 12.1 | 6.73 | 6.42 |
| 2106 | 173 | 125 | 60.2 | 22.8 | 13.0 | 9.22 |
| n | 10 | 10 | 10 | 10 | 10 | 10 |
| n < LLOQ | 0 | 0 | 0 | 0 | 2 | 8 |
| CV % | 36.9 | 29.7 | 27.0 | 31.9 | 63.3 | 215 |
| AM | 165 | 98.0 | 40.8 | 14.2 | 7.37 | 1.56 |
| SD | 61.0 | 29.1 | 11.0 | 4.52 | 4.66 | 3.36 |
| Median | 166 | 100 | 41.8 | 12.8 | 7.80 | 0 |
| Minimum | 73.9 | 50.8 | 27.1 | 8.79 | 0 | 0 |
| Maximum | 262 | 145 | 60.2 | 22.8 | 13.0 | 9.22 |

Lower limit of quantitation (LLOQ) = 5 (µg/L).
N: Number of subjects, n: Number of non-missing observations, hr: Hour, BLQ: Below the limit of quantitation, AM: Arithmetic mean, SD: Standard deviation.
BLQ values are treated as zero.
Values expressed in µg/L
CV % = (SD/Mean) × 100, where SD and mean are standard deviation and arithmetic mean of untransformed data.
Summary statistics for Day 4, 72 hr are based on greater than 30% imputed values.
n < LLOQ = Number of BLQs imputed as zero.

Plasma rivaroxaban pharmacokinetic data for both normal renal function groups and mild renal impairment groups who received both rivaroxaban alone (Period I) and rivaroxaban and verapamil (Period III) are presented in the Tables below:

TABLE 5

Plasma Rivaroxaban Noncompartmental Pharmacokinetic Parameters and Summary Statistics for Treatment Period I Separated by Renal Function Group (PK Analysis Set)
Group 1: Mild Renal Impairment, (N = 14)

| Subject | $C_{max}$ (ng/mL) | $t_{max}$ (hr) | $AUC_{0-t}$ (hr*ng/mL) | $AUC_{0-inf}$ (hr*ng/mL) | $K_{el}$ (1/hr) | $t_{1/2}$ (hr) | CL/F (L/hr) | CL/F/kg ((L/hr)/kg) | $V_z/F$ (L) |
|---|---|---|---|---|---|---|---|---|---|
| 01101 | 251 | 2.00 | 2530 | 2680 | 0.0542 | 12.8 | 7.45 | 0.113 | 138 |
| 01102 | 278 | 1.00 | 3240 | 3370 | 0.0734 | 9.44 | 5.93 | 0.0803 | 80.8 |
| 01103 | 196 | 3.00 | 2690 | 2800 | 0.0825 | 8.40 | 7.14 | 0.114 | 86.5 |
| 01104 | 235 | 0.50 | 2430 | 2510 | 0.0752 | 9.21 | 7.96 | 0.156 | 106 |
| 01106 | 238 | 3.00 | 2830 | 2960 | 0.0491 | 14.1 | 6.76 | 0.0845 | 138 |
| 01108 | 344 | 4.00 | 4350 | 4500 | 0.0778 | 8.91 | 4.45 | 0.0496 | 57.2 |
| 01110 | 306 | 1.00 | 3560 | 3840 | 0.0601 | 11.5 | 5.20 | 0.0670 | 86.5 |
| 01111 | 268 | 3.00 | 3250 | 3600 | 0.0447 | 15.5 | 5.55 | 0.0841 | 124 |
| 01114 | 308 | 1.00 | 2670 | 2760 | 0.0734 | 9.44 | 7.24 | 0.137 | 98.7 |
| 01115 | 215 | 3.00 | 2800 | 2920 | 0.0925 | 7.50 | 6.84 | 0.0946 | 74.0 |
| 01116 | 132 | 1.00 | 1070 | 1170 | 0.0954 | 7.26 | 17.0 | 0.253 | 179 |
| 01118 | 448 | 1.00 | 3880 | 4390 | 0.0240 | 28.9 | 4.56 | 0.0828 | 190 |
| 02101 | 217 | 1.00 | 2200 | 2290 | 0.0786 | 8.82 | 8.74 | NR | 111 |
| 02104 | 232 | 6.00 | 2290 | 2400 | 0.155 | 4.47 | 8.32 | NR | 53.7 |
| n | 14 | 14 | 14 | 14 | 14 | 14 | 14 | 12 | 14 |
| GM* | 252 | NC | 2720 | 2880 | 0.0683 | 10.2 | 6.95 | 0.100 | 102 |
| CVb % | 28.7 | NC | 28.3 | 29.1 | 41.1 | 52.5 | 41.9 | 49.2 | 38.0 |
| AM | 262 | NC | 2840 | 3010 | 0.0740 | 11.2 | 7.37 | 0.110 | 109 |
| SD | 75.2 | NC | 804 | 878 | 0.0304 | 5.87 | 3.09 | 0.0540 | 41.3 |
| Median | 244 | 1.50 | 2750 | 2860 | 0.0743 | 9.32 | 6.99 | 0.0896 | 102 |
| Minimum | 132 | 0.50 | 1070 | 1170 | 0.0240 | 4.47 | 4.45 | 0.0496 | 53.7 |
| Maximum | 448 | 6.00 | 4350 | 4500 | 0.155 | 28.9 | 17.0 | 0.253 | 190 |

*Calculated using log transformed data.
N: Number of subjects,
n: Number of non-missing observations,
GM: Geometric mean,
AM: Arithmetic mean,
SD: Standard deviation,
NR = Not reported;
NC = Not calculated
% CVb = 100 * SQRT [ex[(S^2) − 1]], where S is the standard deviation of the data on a log scale.

TABLE 6

Plasma Rivaroxaban Noncompartmental Pharmacokinetic Parameters and Summary Statistics for Treatment Period I Separated by Renal Function Group Excluding Outlier Sample (PK Analysis Set)
Group 2: Normal Renal Function, (N = 13)

| Subject | $C_{max}$ (ng/mL) | $t_{max}$ (hr) | $AUC_{0-t}$ (hr*ng/mL) | $AUC_{0-inf}$ (hr*ng/mL) | $K_{el}$ (1/hr) | $t_{1/2}$ (hr) | CL/F (L/hr) | CL/F/kg ((L/hr)/kg) | $V_z/F$ (L) |
|---|---|---|---|---|---|---|---|---|---|
| 01105 | 336 | 4.08 | 3370 | 3470 | 0.0955 | 7.26 | 5.76 | 0.0696 | 60.4 |
| 01107 | 297 | 4.00 | 2800 | 2850 | 0.110 | 6.29 | 7.02 | 0.0817 | 63.7 |
| 01109 | 307 | 3.00 | 2930 | 3150 | 0.108 | 6.39 | 6.35 | 0.0829 | 58.6 |
| 01112 | 195 | 2.00 | 2010 | 2070 | 0.0938 | 7.39 | 9.64 | 0.0960 | 103 |
| 01113 | 183 | 3.00 | 1700 | 1790 | 0.0839 | 8.26 | 11.2 | 0.197 | 133 |
| 01117 | 429 | 0.50 | 2670 | 3090 | 0.0336 | 20.6 | 6.46 | 0.0998 | 193 |
| 01119 | 352 | 4.10 | 3560 | 4440 | 0.106 | 6.56 | 4.50 | 0.0579 | 42.6 |
| 01120 | 214 | 1.00 | 2130 | 2200 | 0.0891 | 7.78 | 9.10 | 0.107 | 102 |
| 01121 | 218 | 0.50 | 1700 | 1840 | 0.0511 | 13.6 | 10.9 | 0.177 | 213 |
| 02102 | 212 | 2.00 | 2260 | 2310 | 0.108 | 6.44 | 8.68 | NR | 80.5 |
| 02103 | 230 | 3.00 | 2280 | 2400 | 0.0458 | 15.1 | 8.33 | NR | 182 |
| 02105 | 292 | 4.00 | 3200 | 3260 | 0.0939 | 7.38 | 6.14 | NR | 65.4 |
| 02106 | 266 | 4.00 | 3040 | 3150 | 0.0726 | 9.55 | 6.34 | NR | 87.4 |
| n | 13 | 13 | 13 | 13 | 13 | 13 | 13 | 9 | 13 |
| GM* | 263 | NC | 2520 | 2680 | 0.0793 | 8.74 | 7.47 | 0.0997 | 94.2 |
| CVb % | 26.7 | NC | 24.0 | 27.4 | 30.5 | 46.3 | 26.8 | 44.3 | 53.0 |
| AM | 272 | NC | 2590 | 2770 | 0.0839 | 9.43 | 7.72 | 0.108 | 106 |
| SD | 72.4 | NC | 621 | 760 | 0.0256 | 4.37 | 2.07 | 0.0476 | 56.4 |
| Median | 266 | 3.00 | 2670 | 2850 | 0.0938 | 7.39 | 7.02 | 0.0960 | 87.4 |

TABLE 6-continued

Plasma Rivaroxaban Noncompartmental Pharmacokinetic Parameters
and Summary Statistics for Treatment Period I Separated by
Renal Function Group Excluding Outlier Sample (PK Analysis Set)
Group 2: Normal Renal Function, (N = 13)

| Subject | $C_{max}$ (ng/mL) | $t_{max}$ (hr) | $AUC_{0-t}$ (hr*ng/mL) | $AUC_{0-inf}$ (hr*ng/mL) | $K_{el}$ (1/hr) | $t_{1/2}$ (hr) | CL/F (L/hr) | CL/F/kg ((L/hr)/kg) | $V_z/F$ (L) |
|---|---|---|---|---|---|---|---|---|---|
| Minimum | 183 | 0.50 | 1700 | 1790 | 0.0336 | 6.29 | 4.50 | 0.0579 | 42.6 |
| Maximum | 429 | 4.10 | 3560 | 4440 | 0.110 | 20.6 | 11.2 | 0.197 | 213 |

*Calculated using log transformed data.
N: Number of subjects,
n: Number of non-missing observations,
GM: Geometric mean,
AM: Arithmetic mean,
SD: Standard deviation,
NR = Not reported;
NC = Not calculated
% CVb = 100 * SQRT [ex[(S^2) − 1]], where S is the standard deviation of the data on a log scale.
The Period 1, 48 hr timepoint for subject 01119 was excluded as an outlier from the analysis.

TABLE 7

Plasma Rivaroxaban Noncompartmental Pharmacokinetic
Parameters and Summary Statistics for Treatment Period III
Separated by Renal Function Group (PK Analysis Set)
Group 1: Mild Renal Impairment, (N = 11)

| Subject | $C_{max}$ (ng/mL) | $t_{max}$ (hr) | $AUC_{0-t}$ (hr*ng/mL) | $AUC_{0-inf}$ (hr*ng/mL) | $K_{el}$ (1/hr) | $t_{1/2}$ (hr) | CL/F (L/hr) | CL/F/kg ((L/hr)/kg) | $V_z/F$ (L) |
|---|---|---|---|---|---|---|---|---|---|
| 01101 | 247 | 4.00 | 2950 | 3070 | 0.0721 | 9.61 | 6.51 | 0.0991 | 90.3 |
| 01103 | 300 | 2.00 | 3920 | 4090 | 0.0664 | 10.4 | 4.89 | 0.0781 | 73.6 |
| 01104 | 278 | 0.50 | 3990 | 4140 | 0.0542 | 12.8 | 4.83 | 0.0949 | 89.1 |
| 01106 | 280 | 4.00 | 3870 | 3980 | 0.0820 | 8.46 | 5.03 | 0.0628 | 61.3 |
| 01108 | 303 | 3.00 | 5630 | 5840 | 0.0503 | 13.8 | 3.42 | 0.0382 | 68.1 |
| 01111 | 327 | 4.00 | 5810 | 6090 | 0.0323 | 21.4 | 3.28 | 0.0497 | 102 |
| 01114 | 279 | 2.00 | 3230 | 3530 | 0.0283 | 24.5 | 5.66 | 0.107 | 200 |
| 01116 | 242 | 4.00 | 2680 | 2820 | 0.0590 | 11.7 | 7.08 | 0.105 | 120 |
| 01118 | 458 | 4.00 | 5990 | 6300 | 0.0418 | 16.6 | 3.17 | 0.0577 | 76.0 |
| 02101 | 202 | 0.50 | 3010 | 3260 | 0.0598 | 11.6 | 6.14 | NR | 103 |
| 02104 | 136 | 0.50 | 3280 | 3480 | 0.0374 | 18.5 | 5.74 | NR | 154 |
| n | 11 | 11 | 11 | 11 | 11 | 11 | 11 | 9 | 11 |
| GM* | 267 | NC | 3880 | 4080 | 0.0504 | 13.7 | 4.90 | 0.0728 | 97.1 |
| CVb % | 28.9 | NC | 30.2 | 29.6 | 32.0 | 35.6 | 26.2 | 33.6 | 40.2 |
| AM | 277 | NC | 4030 | 4240 | 0.0530 | 14.5 | 5.07 | 0.0770 | 103 |
| SD | 80.1 | NC | 1220 | 1260 | 0.0170 | 5.16 | 1.33 | 0.0259 | 41.5 |
| Median | 279 | 3.00 | 3870 | 3980 | 0.0542 | 12.8 | 5.03 | 0.0781 | 90.3 |
| Minimum | 136 | 0.50 | 2680 | 2820 | 0.0283 | 8.46 | 3.17 | 0.0382 | 61.3 |
| Maximum | 458 | 4.00 | 5990 | 6300 | 0.0820 | 24.5 | 7.08 | 0.107 | 200 |

*Calculated using log transformed data.
N: Number of subjects, n: Number of non-missing observations, GM: Geometric mean, AM: Arithmetic mean, SD: Standard deviation.
NR = Not reported;
NC = Not calculated
% CVb = 100 * SQRT [ex[(S^2) − 1]], where S is the standard deviation of the data on a log scale.

TABLE 8

Plasma Rivaroxaban Noncompartmental Pharmacokinetic
Parameters and Summary Statistics for Treatment Period III
Separated by Renal Function Group (PK Analysis Set)
Group 2: Normal Renal Function, (N = 10)

| Subject | $C_{max}$ (ng/mL) | $t_{max}$ (hr) | $AUC_{0-t}$ (hr*ng/mL) | $AUC_{0-inf}$ (hr*ng/mL) | $K_{el}$ (1/hr) | $t_{1/2}$ (hr) | CL/F (L/hr) | CL/F/kg ((L/hr)/kg) | $V_z/F$ (L) |
|---|---|---|---|---|---|---|---|---|---|
| 01105 | 383 | 4.00 | 3780 | 3840 | 0.0884 | 7.84 | 5.21 | 0.0629 | 58.9 |
| 01107 | 331 | 3.00 | 3990 | 4060 | 0.0866 | 8.00 | 4.92 | 0.0573 | 56.9 |
| 01109 | 302 | 2.00 | 3770 | 3930 | 0.0672 | 10.3 | 5.08 | 0.0664 | 75.7 |
| 01112 | 163 | 1.00 | 2690 | 2820 | 0.0656 | 10.6 | 7.08 | 0.0705 | 108 |
| 01119 | 348 | 4.00 | 4260 | 4330 | 0.121 | 5.71 | 4.61 | 0.0594 | 38.0 |
| 01120 | 260 | 3.00 | 2690 | 2800 | 0.0810 | 8.55 | 7.14 | 0.0839 | 88.1 |
| 01121 | 208 | 2.00 | 2260 | 2530 | 0.0456 | 15.2 | 7.90 | 0.128 | 173 |
| 02102 | 225 | 2.00 | 3500 | 3670 | 0.0643 | 10.8 | 5.46 | NR | 84.9 |
| 02103 | 269 | 1.00 | 3780 | 3880 | 0.0614 | 11.3 | 5.15 | NR | 83.9 |

TABLE 8-continued

Plasma Rivaroxaban Noncompartmental Pharmacokinetic
Parameters and Summary Statistics for Treatment Period III
Separated by Renal Function Group (PK Analysis Set)
Group 2: Normal Renal Function, (N = 10)

| Subject | $C_{max}$ (ng/mL) | $t_{max}$ (hr) | $AUC_{0-t}$ (hr*ng/mL) | $AUC_{0-inf}$ (hr*ng/mL) | $K_{el}$ (1/hr) | $t_{1/2}$ (hr) | CL/F (L/hr) | CL/F/kg ((L/hr)/kg) | $V_z/F$ (L) |
|---|---|---|---|---|---|---|---|---|---|
| 02106 | 394 | 4.00 | 4620 | 4800 | 0.0511 | 13.6 | 4.17 | NR | 81.6 |
| n | 10 | 10 | 10 | 10 | 10 | 10 | 10 | 7 | 10 |
| GM* | 278 | NC | 3460 | 3600 | 0.0705 | 9.83 | 5.56 | 0.0727 | 78.8 |
| CVb % | 26.6 | NC | 21.4 | 19.9 | 30.0 | 27.6 | 21.9 | 33.0 | 43.2 |
| AM | 288 | NC | 3530 | 3670 | 0.0732 | 10.2 | 5.67 | 0.0755 | 84.9 |
| SD | 76.8 | NC | 755 | 728 | 0.0220 | 2.82 | 1.24 | 0.0249 | 36.7 |
| Median | 286 | 2.50 | 3780 | 3860 | 0.0664 | 10.4 | 5.18 | 0.0664 | 82.7 |
| Minimum | 163 | 1.00 | 2260 | 2530 | 0.0456 | 5.71 | 4.17 | 0.0573 | 38.0 |
| Maximum | 394 | 4.00 | 4620 | 4800 | 0.121 | 15.2 | 7.90 | 0.128 | 173 |

*Calculated using log transformed data.
N: Number of subjects, n: Number of non-missing observations, GM: Geometric mean, AM: Arithmetic mean, SD: Standard deviation.
NR = Not reported;
NC = Not calculated
% CVb = 100 * SQRT [ex[(S^2) − 1]], where S is the standard deviation of the data on a log scale.

Figure 1:
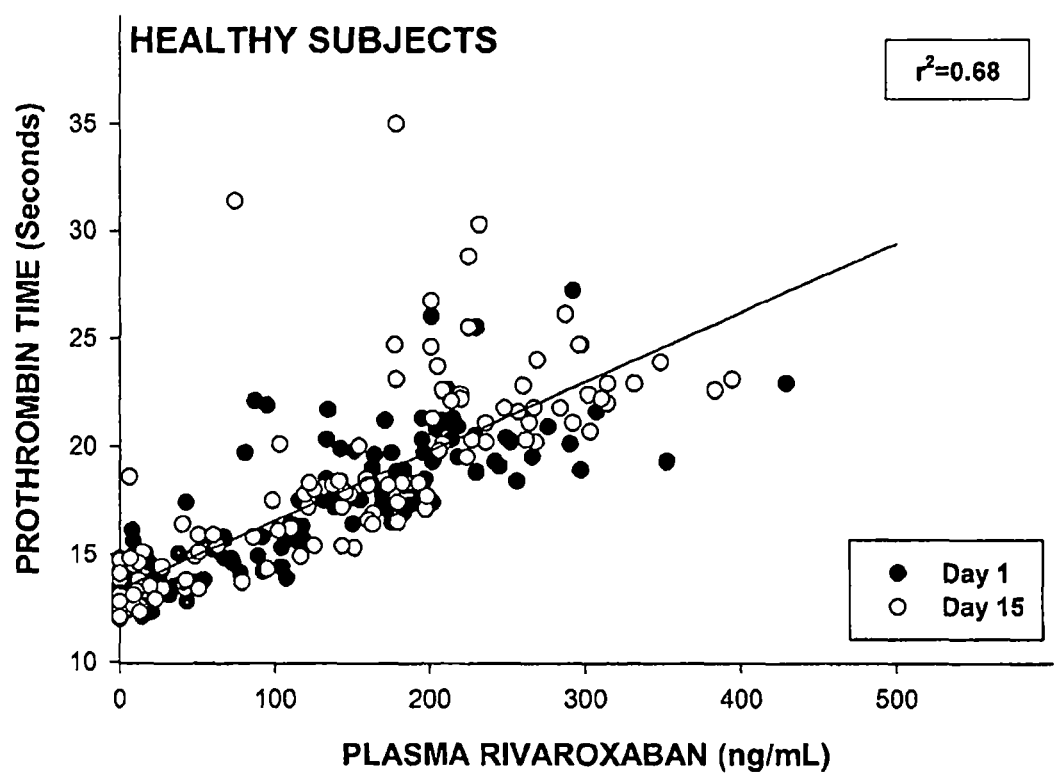
FIG. 1 shows a correlation between plasma concentrations of rivaroxaban and Prothrombin Time ("PT") in subjects with no renal insufficiency. Data were measured on Day 1 and Day 15 of the study.
Figure 2:
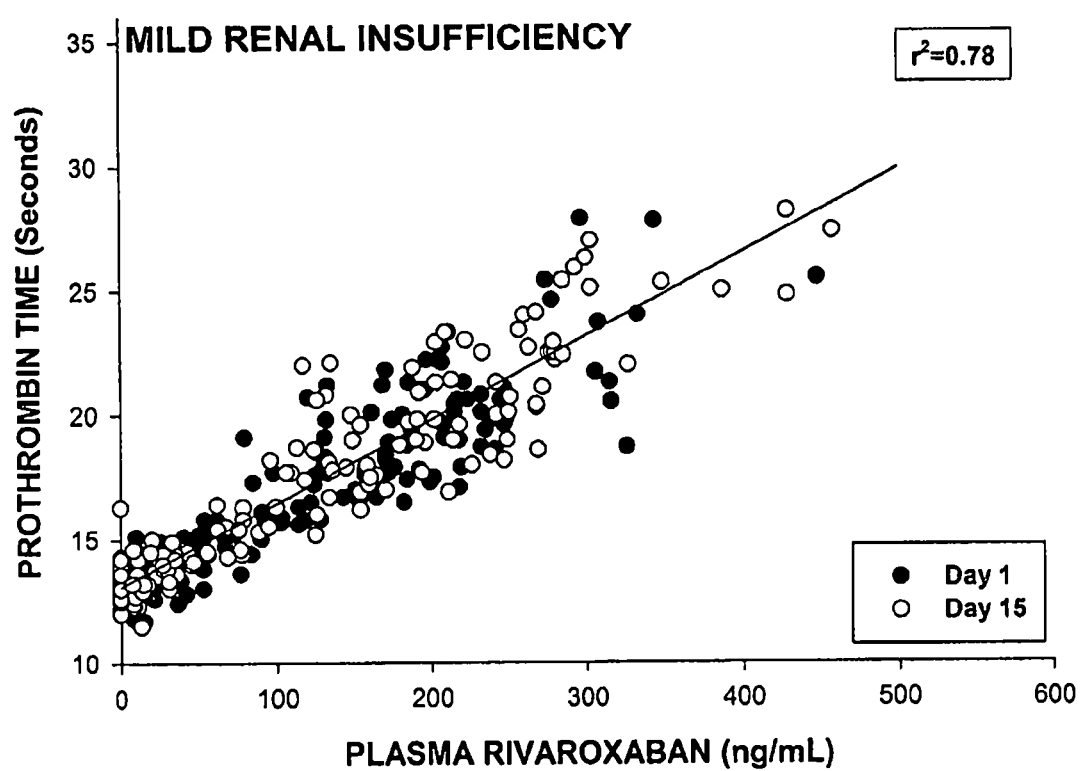
FIG. 2 shows a correlation between plasma concentrations of rivaroxaban and PT in subjects with mild renal insufficiency. Data were measured on Day 1 and Day 15 of the study.

Example 3. Plasma Rivaroxaban Concentrations and the Risk of Major Bleeding in Subjects with Mild Renal Impairment To evaluate the relationship between the plasma levels of rivaroxaban and the risk of major bleeding, the subjects with mild renal insufficiency were given a single 20 mg dose of rivaroxaban on the first day of the study (as described in the study in Example 2). Blood samples were collected and processed according to the standard protocols. Plasma rivaroxaban concentrations were measured on Day 1 and Day 15. As shown in FIGS. 1 and 2, the risk of major bleeding based on PT values, were positively correlated with increased plasma concentrations of rivaroxaban. The results showed a clear linear relationship between the pharmacokinetics and the pharmacodynamics of rivaroxaban in subjects with normal renal function and mild renal insufficiency.

The steady state area under the curve (AUC) of plasma rivaroxaban in subjects with either normal renal function or mild renal impairment under different treatment regimens was also examined. As shown in FIG. 3, the leftmost 6 box plots (study 10842) show the distribution of AUC values for various dosing levels of rivaroxaban (10 mg, 20 mg, 30 mg, 40 mg, 60 mg, and 80 mg, respectively) previously measured in clinical trials supporting FDA approval of Xarelto® (rivaroxaban). The next nine box plots (studies 10993, 10999, 12359, 12680, 11273, 10989, and 11938) in the middle represent subjects treated with a single 20 mg dose of rivaroxaban under normal, fasted, or fed condition. All show the geometric mean plus or minus one standard deviation. The last four box plots show the distribution of AUC values measured in the present study, for subjects with normal renal function (designated "N") and subjects with mild renal impairment (designated "MRI") who were either treated with a single 20 mg dose of rivaroxaban ("P1") or a single 20 mg dose of rivaroxaban and 360 mg verapamil ("P3"). These four show the geometric mean and the full minimum and maximum subject value range.

The results in FIG. 3 show that the geometric mean in the subjects with mild renal impairment treated with both rivaroxaban and verapamil in the present study was about one standard deviation higher than the mean AUC levels in subjects with normal renal function treated with a single 80 mg dose of rivaroxaban. The present study shows that subjects with mild renal impairment who took both rivaroxaban and verapamil had mean AUC levels well above the AUC levels observed in subjects with normal renal function treated with a single 20 mg dose of rivaroxaban; that is, such patients coadministered rivaroxaban and verapamil have AUC values substantially higher than values currently considered acceptable by the FDA.

Another representation of these data are shown in FIG. 4. Label "A" represents the upper bound of the 90% confidence interval of the steady state AUC of patients administered 20 mg of rivaroxaban, about 3,792 μg·hr/L. Label "B" is the estimated steady state AUC, about 3,404 μg·hr/L for patients administered a single 10 mg dose of rivaroxaban in combination with a strong CYP3A4/Pgp inhibitor. Label "C" is the upper boundary of the 90% confidence interval of the steady state AUC level in subjects treated with a single 20 mg dose of rivaroxaban after a meal, about 2,448 μg·hr/L. The remaining 4 box plots are reproduced from FIG. 3. FIG. 4 shows that $AUC_{inf}$ values in subjects with mild renal impairment ("MRI") treated with a single 20 mg dose of rivaroxaban and 360 mg verapamil (P3) are significantly higher than expected from previous studies. For example, the geometric mean of the steady state AUC for such patients was higher than the upper limits of safety identified in the FDA's Clinical Pharmacology review for rivaroxaban, demonstrating that a significant portion of the relevant patient population who have mild renal impairment have AUC values falling outside of the range accepted by the FDA. Further, the present study shows that a significant portion of patients with normal renal function treated with rivaroxaban and verapamil have plasma levels significantly higher than the upper boundary of the 90% confidence interval of the steady state AUC level in subjects from the rivaroxaban approval studies treated with a single 20 mg dose of rivaroxaban (Label "C"), demonstrating a higher bleeding risk than is presently recognized in the art. Additionally, the present study shows that patients with mild renal impairment have plasma levels of rivaroxaban which are significantly higher than the upper boundary of the 90% confidence interval of the steady state AUC level in subjects from the rivaroxaban approval studies treated with a single 20 mg dose of rivaroxaban (Label "C"), demonstrating a higher bleeding risk than is presently recognized in the art.

FIG. 5 shows that the relationship between steady state rivaroxaban AUC and the risk of major bleeding. Group "a" in FIG. 5 represents the average geometric mean of fed subjects across two studies (10989 and 11938) who took a single 20 mg rivaroxaban and had an average of AUC of approximately 2,026 μg·hr/L, which corresponded to about 3% risk of major bleeding. Group "b" in the FIG. 5 represents subjects with mild renal impairment who took a single 20 mg rivaroxaban and 360 mg verapamil and had an estimated of $AUC_{inf}$ of approximately 5,469 μg·hr/L, which shows that the mild renal impairment caused higher accumulation of rivaroxaban in the plasma and led to 2.5 times higher the risk of major bleeding compared to the populations in Group "a". Group "c" represents the average of the three subjects in Group "b" who had the highest $AUC_{inf}$, which was about 8,143 μg·hr/L. The risk of major bleeding of the subjects in Group "c" were at least 5 times higher compared to the populations in Group "a" and not even visible on this scale.

Example 4. Drug-Drug Interaction with Oral Verapamil and 2.5 mg of Rivaroxaban

A control study is performed to determine the presence of DDIs in patients treated with oral verapamil and rivaroxaban (without aspirin). This study is performed through a University, Hospital, Clinic, or other facility with proper approvals and access to subjects and is performed to demonstrate the presence of DDIs. A representative example of a sample study is found in Example 1.

This study compares and assesses the pharmacokinetic and pharmacodynamic consequences of 0.5-2.5 mg of rivaroxaban and various recommended doses of verapamil when concomitantly administered to patients (e.g., healthy and renally impaired) by measuring blood plasma levels at various time intervals after dosing.

The outcomes of such a study shows that verapamil causes higher rivaroxaban plasma concentrations, prolonged PT, and increased Factor Xa inhibition. Patients are administered 0.5-2.5 mg of rivaroxaban concomitantly with verapamil (100-480 mg), and blood plasma levels are measured and compared to similar (e.g., identical) patients who were not administered verapamil. Patents concomitantly treated with rivaroxaban and verapamil have a much higher plasma rivaroxaban level than for a similar (e.g., identical) patient who has not taken verapamil.

In one study, patients are administered a 2.5 mg dose of rivaroxaban and concomitantly administered verapamil. The blood plasma level of rivaroxaban for such a patient is equal to or greater than a similar patient who has taken a 5 mg dose of rivaroxaban and who has not taken verapamil. That is, the average geometric mean of subjects who take a single dose of rivaroxaban (e.g., 2.5 mg), and verapamil (e.g., 360 mg) have an average AUC of approximately 1064.25 μg·hr/L or greater. The geometric mean AUC of rivaroxaban for 5 mg dose of rivaroxaban is 1064.25 μg·h/L. Thus, consistent with Example 1, the blood plasma levels of a patient who is administered 2.5 mg of rivaroxaban and who is concomitantly administered verapamil is approximately equal to those of patient who is administered 5 mg of rivaroxaban.

In another study, patients are administered a 1.75 mg dose of rivaroxaban and concomitantly administered verapamil. The blood plasma level of rivaroxaban for such a patient is approximately equal to a similar patient who has taken a 2.5 mg dose of rivaroxaban and who has not taken verapamil. That is, the average geometric mean of subjects who take a single dose of rivaroxaban (e.g., 1.75 mg) and verapamil (e.g., 360 mg) have an average AUC of approximately about 80% of 165.4 μg·h/L to about 125% of about 551.9 μg·h/L. The geometric mean AUC of rivaroxaban for 2.5 mg dose of rivaroxaban is 165.4 μg·h/L to 551.9 μg·h/L. Thus, consistent with Example 1, the blood plasma levels of a patient who is administered 1.75 mg of rivaroxaban and who is concomitantly administered verapamil is approximately equal to those of patient who is administered 2.5 mg of rivaroxaban.

Example 5. Oral Verapamil, Aspirin, and Rivaroxaban Drug-Drug Interaction

Additional studies are performed to determine the presence of DDIs in patients treated with oral verapamil, aspirin, and rivaroxaban. This study is performed through a University, Hospital, Clinic, or other facility with proper approvals and access to subjects and is performed to demonstrate the presence of DDIs. A representative example of such a study is found in Example 1.

This study assesses the pharmacokinetic and pharmacodynamic consequences of concomitant administration 0.5-2.5 mg of rivaroxaban, 100 mg of aspirin, and recommended doses of verapamil in patients (e.g., healthy and renally impaired) by measuring blood plasma levels at various time intervals after dosing. Patients are administered 0.5-2.5 mg of rivaroxaban concomitantly with verapamil (100-480 mg), and blood plasma levels are measured and compared to similar (e.g., identical) patients who were not administered verapamil. Patents concomitantly treated with rivaroxaban and verapamil have a much higher plasma rivaroxaban level than for a similar (e.g., identical) patient who has not taken verapamil. Additionally, these studies show a linear relationship between the pharmacokinetic and the pharmacodynamics of rivaroxaban in subjects with normal renal function and renal insufficiency.

This study also investigates the plasma levels of rivaroxaban and the risk of major bleeding in patients (e.g., healthy and renally impaired) in accordance with Example 1. This study, for example, examines the steady state area under the curve (AUC) of plasma rivaroxaban in subjects with either normal renal function or renal impairment under different treatment regimens.

This study shows that the concomitant administration of oral verapamil, aspirin, and rivaroxaban leads to a higher accumulation of rivaroxaban in the plasma, resulting in a significantly higher risk of major bleeding compared to subjects not concomitantly administered verapamil. Additional outcomes include a linear relationship between the risk of major bleeding in subjects with normal renal function and renal insufficiency.

In one study, patients are administered a 2.5 mg dose of rivaroxaban and concomitantly administered verapamil and aspirin (100 mg). The blood plasma level of rivaroxaban for such a patient is equal to or greater than a similar patient who has taken a 5 mg dose of rivaroxaban and who has not taken verapamil, and the risk of major bleeding is equal to or greater than that measured for a similar patient who has taken a 5 mg dose of rivaroxaban and who has not taken verapamil. That is, the average geometric mean of subjects who take a single dose of rivaroxaban (e.g., 2.5 mg), and verapamil (e.g., 360 mg) has an average AUC of approximately 1064.25 μg·hr/L or greater and a risk of major bleeding of not more than about 4.5%, e.g., about 3% The geometric mean AUC of rivaroxaban for 5 mg dose of rivaroxaban is 1064.25 μg·h/L. Thus, consistent with Example 1, the blood plasma levels of a patient who is administered 2.5 mg of rivaroxaban and who is concomitantly administered verapamil are approximately equal to those of patient who is administered 5 mg of rivaroxaban.

In another study, patients are administered a 1.75 mg dose of rivaroxaban and concomitantly administered verapamil. The blood plasma level of rivaroxaban for such a patient is approximately equal to a similar patient who has taken a 2.5 mg dose of rivaroxaban and who has not taken verapamil and the risk of major bleeding is less than or equal to that measured for a similar patient who has taken a 5 mg dose of rivaroxaban and who has not taken verapamil. That is, the average geometric mean of subjects who take a single dose of rivaroxaban (e.g., 1.75 mg) and verapamil (e.g., 360 mg) have an average AUC of approximately about 80% of 165.4 µg·h/L to about 125% of about 551.9 µg·h/L, and a risk of major bleeding of not more than about 4.5%, e.g., from about 1.5-2.0%. The geometric mean AUC of rivaroxaban for 2.5 mg dose of rivaroxaban is 165.4 µg·h/L to 551.9 µg·h/L. Thus, consistent with Example 1, the blood plasma levels of a patient who is administered 1.75 mg of rivaroxaban and who is concomitantly administered verapamil is approximately equal to those of a patient who is administered 2.5 mg of rivaroxaban.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

INCORPORATION BY REFERENCE

The following references are herein incorporated by reference in their entireties:
1. Connolly et al., *Lancet*, 391: 205-18 (2018).
2. Anand et al., *Lancet*, 391, 219-229, 20 (2018).
3. Mega et al., *N Engl J Med*, 366:9-19 (2012).
4. Correspondence for Rivaroxaban in Stable Cardiovascular Disease, *N Engl J Med*, 378; 4 (2018).
5. Eikelboom et al., *N Engl J Med*, 377:1319-30 (2017).
6. US Patent Application Publication 2017/0239260 A1

The invention claimed is:

1. A method of treating a patient in need of treatment with rivaroxaban, comprising: (a) administering about 100 to about 480 mg of verapamil daily to the patient; (b) optionally administering about 75 mg to about 325 mg of aspirin to the patient; and (c) administering about 2.5 mg or less of rivaroxaban to the patient, wherein the patient has a CLcr of less than or equal to about 79 mg/mL mL/min.

2. The method of claim 1, wherein the dose of verapamil administered in step (a) is 120, 240, 360, or 480 mg.

3. The method of claim 1, wherein a 100 mg dose of aspirin is administered in step (b).

4. The method of claim 3, wherein the patient is administered 100 mg of aspirin once daily.

5. The method of claim 1, wherein the dose of rivaroxaban administered in step (c) ranges from about 20% to about 95% of 2.5 mg.

6. The method of claim 1, wherein the dose of rivaroxaban administered in step (c) ranges from about 0.5 mg to about 2.0 mg.

7. The method of claim 1, wherein the dose of rivaroxaban administered in step (c) is selected from the group consisting of about 0.5 mg, about 0.75 mg, about 1.0 mg, about 1.25 mg, about 1.5 mg, about 1.75 mg, and about 2.0 mg.

8. The method of claim 1, wherein the dose of rivaroxaban administered in step (c) is about 1.75 mg.

9. The method of claim 1, wherein the dose of rivaroxaban is administered in an immediate release or rapid release formulation.

10. The method of claim 1, wherein the patient is administered the dose rivaroxaban twice daily.

11. The method of claim 1, wherein the total daily dose of rivaroxaban administered to the patient is less than about 5 mg or less.

12. The method of claim 11, wherein the total daily dose of rivaroxaban administered to the patient is about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, or about 4.75 mg.

13. The method of claim 1, wherein the patient is treated for a disease or condition selected from the group consisting of: decreasing the risk of major cardiovascular events selected from the group consisting of death, myocardial infarction, and stroke in patients with chronic coronary and/or peripheral artery disease; reducing the risk of acute limb ischemia in patients with peripheral artery disease; decreasing the risk of major cardiovascular events selected from the group consisting of death, myocardial infarction, and stroke in patients with acute coronary syndrome; reducing the risk of major thrombotic vascular events in subjects with symptomatic peripheral artery disease undergoing peripheral revascularization procedures of the lower extremities; and reducing the risk of death or thromboembolic events after transcatheter aortic valve replacement.

14. The method of claim 1, wherein the patient is mildly to severely renally impaired.

15. The method of claim 1, wherein the patient has a $CL_{Cr}$ of 50-79 mL/min.

16. The method of claim 1, wherein the patient has a $CL_{Cr}$ of 30-49 mL/min.

17. The method of claim 1, wherein the patient has a $CL_{Cr}$ of less than 30 mL/min.

18. The method of claim 1, wherein the daily dose of rivaroxaban is about 2.5 mg.

19. The method of claim 1, wherein about 0.5 mg to less than about 2.5 mg of rivaroxaban is administered in step (c).

* * * * *